(12) United States Patent
Mello et al.

(10) Patent No.: US 11,981,892 B2
(45) Date of Patent: May 14, 2024

(54) COMPOSITIONS AND METHODS FOR IMPROVED GENE EDITING

(71) Applicant: UNIVERSITY OF MASSACHUSETTS, Boston, MA (US)

(72) Inventors: Craig Cameron Mello, Barrington, RI (US); Krishna Sumanth Ghanta, Grafton, MA (US); Gregoriy Dokshin, Belmont, MA (US); Aamir Mir, Worcester, MA (US); Hassan Gneid, Worcester, MA (US); Jonathan Kenneth Watts, Worcester, MA (US); Erik Joseph Sontheimer, Auburndale, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 325 days.

(21) Appl. No.: 16/384,612

(22) Filed: Apr. 15, 2019

(65) Prior Publication Data

US 2019/0345479 A1   Nov. 14, 2019

Related U.S. Application Data

(60) Provisional application No. 62/679,315, filed on Jun. 1, 2018, provisional application No. 62/658,368, filed on Apr. 16, 2018.

(51) Int. Cl.
| | | |
|---|---|---|
| *C12N 15/10* | (2006.01) | |
| *C12N 9/22* | (2006.01) | |
| *C12N 15/113* | (2010.01) | |
| *C12N 15/66* | (2006.01) | |
| *C12N 15/90* | (2006.01) | |

(52) U.S. Cl.
CPC ............ *C12N 15/102* (2013.01); *C12N 9/22* (2013.01); *C12N 15/113* (2013.01); *C12N 15/66* (2013.01); *C12N 15/902* (2013.01)

(58) Field of Classification Search
None
See application file for complete search history.

(56) References Cited

U.S. PATENT DOCUMENTS

| | | |
|---|---|---|
| 5,684,143 A | 11/1997 | Gryaznov et al. |
| 5,858,988 A | 1/1999 | Wang |
| 6,001,650 A | 12/1999 | Colosi |
| 6,156,303 A | 12/2000 | Russell et al. |
| 6,291,438 B1 | 9/2001 | Wang |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,586,363 B2 | 11/2013 | Voytas et al. |
| 8,697,853 B2 | 4/2014 | Voytas et al. |
| 8,771,985 B2 | 7/2014 | Cui et al. |
| 9,187,758 B2 | 11/2015 | Cai et al. |
| 9,206,404 B2 | 12/2015 | Cui et al. |
| 9,393,257 B2 | 7/2016 | Osborn et al. |
| 2003/0138772 A1 | 7/2003 | Gao et al. |
| 2008/0045473 A1 | 2/2008 | Uhlmann et al. |
| 2012/0136039 A1 | 5/2012 | Aronin et al. |
| 2012/0282699 A1 | 11/2012 | Bundock et al. |
| 2012/0329067 A1 | 12/2012 | Barbas, III et al. |
| 2013/0326645 A1 | 12/2013 | Cost et al. |
| 2014/0121115 A1 | 5/2014 | Arnould et al. |
| 2017/0051276 A1* | 2/2017 | May .................... A61P 13/12 |
| 2017/0051286 A1 | 2/2017 | Smith |
| 2017/0058298 A1* | 3/2017 | Kennedy ................ C12N 9/22 |
| 2018/0094263 A1 | 4/2018 | Khvorova et al. |
| 2018/0201926 A1* | 7/2018 | Shriver ............... C07K 16/005 |
| 2018/0230494 A1* | 8/2018 | Joung .................... C12N 15/63 |
| 2019/0119701 A1* | 4/2019 | Liang .................. C07K 14/195 |
| 2022/0348912 A1 | 11/2022 | Mello et al. |
| 2023/0017203 A1 | 4/2023 | Mello et al. |

FOREIGN PATENT DOCUMENTS

| | | |
|---|---|---|
| EP | 3781677 A1 | 2/2021 |
| WO | WO 1998/054311 A1 | 12/1998 |
| WO | WO 2013/126794 A1 | 8/2013 |
| WO | WO 2014/102688 A1 | 7/2014 |
| WO | WO 2014/191525 A1 | 12/2014 |
| WO | WO 2017/019867 A1 | 2/2017 |
| WO | WO 2019/051237 A1 | 3/2017 |
| WO | WO 2017/096041 A1 | 6/2017 |
| WO | WO 2017/205650 A1 | 11/2017 |
| WO | WO 2018/026976 A1 | 2/2018 |
| WO | WO 2019/204226 A1 | 10/2019 |

(Continued)

OTHER PUBLICATIONS

Haurwitz et al., Sequence- and structure-specific RNA processing by a CRISPR endonuclease. Science (2010) 329: 1355-1358 (Year: 2010).*

Alemdaroglu et al., DNA multiblock copolymers. Chem. Commun. (2007), 1358-1359 (Year: 2007).*

Johannes Winkler, Therapeutic oligonucleotides with polyethylene glycol modifications. Future Med. Chem. (2015), 7(13), 1721-1731 (Year: 2015).*

Ugarte-Uribe et al., Synthesis, Cell-Surface Binding, and Cellular Uptake of Fluorescently Labeled Glucose-DNA Conjugates with Different Carbohydrate Presentation. Bioconjugate Chem. (2010), 21: 1280-1287 (Year: 2010).*

Pils and Micura., Flexible non-nucleotide linkers as loop replacements in short double helical RNAs. Nucleic Acids Research (2000), 28(9): 1859-1863 (Year: 2000).*

(Continued)

*Primary Examiner* — Neil P Hammell
*Assistant Examiner* — Catherine Konopka
(74) *Attorney, Agent, or Firm* — LATHROP GPM LLP; James H. Velema, Esq.; Michael J. Spellberg, Esq.

(57) ABSTRACT

The disclosure provides novel methods and compositions for gene editing. In particular, the disclosure relates to compositions and methods of making modified nucleic acid donor templates for highly efficient and precise gene editing.

39 Claims, 28 Drawing Sheets

Specification includes a Sequence Listing.

(56) References Cited

FOREIGN PATENT DOCUMENTS

| WO | WO 2020/086908 A1 | 4/2020 |
|---|---|---|
| WO | WO 2020/257684 A1 | 12/2020 |

OTHER PUBLICATIONS

Dohmen et al., Defined Folate-PEG-siRNA Conjugates for Receptor-specific Gene Silencing. Molecular Therapy-Nucleic Acids (2012) 1, e7 (Year: 2012).*
New England Biolabs, PflFI, https://www.neb.com/products/r0595-pflfi [retrieved Jul. 13, 2023] (Year: 2023).*
SynBioBeta, Building DNA on a chip: a novel approach to gene synthesis, published Jul. 8, 2019, https://www.synbiobeta.com/read/building-dna-on-a-chip-a-novel-approach-to-gene-synthesis [retrieved Jul. 13, 2023] (Year: 2019).*
Integrated DNA technologies, Int Spacer 18, https://www.idtdna.com/site/catalog/modifications/product/1393 [retrieved Jul. 13, 2023] (Year: 2023).*
Basic Local Alignment Search Tool, https://blast.ncbi.nlm.nih.gov/Blast.cgi , [retrieved alignments Jul. 13, 2023] (Year: 2023).*
New England Biolabs, MscI, https://www.neb.com/products/r0534-msci [retrieved Jul. 15, 2023] (Year: 2023).*
Business Wire (https://www.businesswire.com/news/home/20230309005124/en/Ansa-Biotechnologies-Announces-Successful-de-novo-Synthesis-of-World%E2%80%99s-Longest-Oligonucleotide-at-1005-Bases, published Mar. 9, 2023, [retrieved Jul. 15, 2023] (Year: 2023).*
Pozza et al., Three's a crowd—stabilisation, structure, and applications of DNA triplexes. Chem. Sci. (2022), 13: 10193 (Year: 2022).*
Majumdar et al., Targeted Gene Knock In and Sequence Modulation Mediated by a Psoralen-linked Triplex-forming Oligonucleotide. The Journal of Biological Chemistry (2008), 283: 11244-11252 (Year: 2008).*
Chan et al., Chan et al., The Journal of Biological Chemistry, 274(17): 11541-11548. The Journal of Biological Chemistry (1999), 274(17): 11541-11548 (Year: 1999).*
Okamoto et al., Triplex forming ability of oligonucleotides containing 20-O-methyl-2-thiouridine or 2-thiothymidine. Bioorganic and Medicinal Chemistry Letters (2006), 16: 3334-3336 (Year: 2006).*
Maurisse et al., A new method (GOREC) for directed mutagenesis and gene repair by homologous recombination. Gene Therapy (2002), 9: 703-707 (Year: 2002).*
Mali et al., RNA-Guided Human Genome Engineering via Cas9. Science (2013), 339: 823-826 and supplemental materials (Year: 2013).*
Li Min, Master's Thesis: Preparation and Self-assembly of DNA-g-polymer, published in May 2015. Engilsh translation of sections 1.4 and 2.1 provided (Year: 2015).*
Amrani, et al., NmeCas9 is an Intrinsically High-Fidelity Genome-Editing Platform, Genome Biology, vol. 19, No. 214, 1-25 pages, Dec. 5, 2018.
Arribere, et al., Efficient Marker-Free Recovery of Custom Genetic Modifications with CRISPR/Cas9 in Caenorhabditis Elegans, Genetics, vol. 198, No. 3, pp. 837-846, Nov. 1, 2014.
Benoit, et al., Seamless Insert-Plasmid Assembly at High Efficiency and Low Cost, PLoS One, vol. 11, No. 4, pp. 1-13., Apr. 13, 2016.
Bernhofer, et al., NLSDB-Major Update for Database of Nuclear Localization Signals and Nuclear Export Signals, Nucleic Acids Research, vol. 46, pp. D503-D508, Nov. 2, 2017.
Brandén, et al., A peptide nucleic acid-nuclear localization signal fusion that mediates nuclear transport of DNA, Nature Biotechnology, vol. 17, No. 8, pp. 784-787, Aug. 1, 1999.
Briner, et al., Guide RNA Functional Modules Direct Cas9 Activity and Orthogonality, Molecular Cell, vol. 56, No. 2, pp. 333-339., Oct. 23, 2014.
Cermak, et al., Efficient Design and Assembly of Custom TALEN and Other TAL Effector-Based Constructs for DNA Targeting, Nucleic Acids Research, vol. 39, No. 12, e82 page, Jul. 1, 2011.

Eckstein, Fritz, Phosphorothioate Oligodeoxynucleotides: What Is Their Origin and What Is Unique About Them?, Antisense and Nucleic Acid Drug Development, vol. 10, Issue 2, pp. 117-121., 2000.
Extended European Search Report Received for EP Patent Application No. 19788536.1, dated Dec. 20, 2021.
Ghanta, et al., 5'-modifications Improve Potency and Efficacy of Dna Donors for Precision Genome Editing, Elife, vol. 10, pp. 1-20., Jun. 22, 2018.
He, et al., Knock-In of Large Reporter Genes in Human Cells via CRISPR/Cas9-Induced Homology-Dependent and Independent DNA Repair, Nucleic Acids Research, vol. 44, No. 9, pp. 1-14., May 19, 2016.
Herdewijn, Piet, Heterocyclic Modifications of Oligonucleotides and Antisense Technology, Antisense and Nucleic Acid Drug Development, vol. 10, Issue 4, pp. 297-310., Jul. 8, 2004.
Hisano, et al., Precise In-Frame Integration of Exogenous DNA Mediated by CRISPR/Cas9 System in Zebrafish, Scientific Reports, vol. 5, No. 8841, pp. 1-7, Mar. 5, 2015.
International Search Report & Written Opinion Received for PCT Application No. PCT/US2020/038789, dated Nov. 10, 2020.
Jiang, et al., RNA-guided editing of bacterial genomes using CRISPR-Cas systems, Nature biotechnology, vol. 31, No. 3, pp. 233-239., Jan. 29, 2013.
Jinek, et al., A Programmable Dual-RNA-Guided DNA Endonuclease In Adaptive Bacterial Immunity, Science, vol. 337, No. 6096, pp. 816-821., Aug. 17, 2012.
Kosugi, et al., Six Classes of Nuclear Localization Signals Specific to Different Binding Grooves of Importin Alpha., Journal of Biological Chemistry, vol. 284, No. 1, pp. 478-485, Jan. 2, 2009.
Li, et al., Design and Specificity of Long ssDNA Donors for CRISPR-based Kknock-In, BioRxiv, 24 pages, Aug. 21, 2017.
Ludtke, et al., A Nuclear Localization Signal Can Enhance Both the Nuclear Transport and Expression of 1 kb DNA, Journal of Cell Science, vol. 112, Point 12, pp. 2033-2041, Jun. 1, 1999.
Mali, et al., RNA-Guided Human Genome Engineering Via Cas9, Science, vol. 339, No. 6121, pp. 823-826., Feb. 15, 2013.
Nishimasu, et al., Crystal Structure Of Cas9 In Complex With Guide RNA And Target DNA, Cell, vol. 156, No. 5, pp. 935-949., Feb. 27, 2014.
Nishimasu, et al., Crystal Structure of *Staphylococcus aureus* Cas9, Cell, vol. 162, No. 5, pp. 1113-1126., Aug. 27, 2015.
Ran, et al., Genome engineering using the CRISPR-Cas9 system, Nature Protocols, vol. 8, No. 11, pp. 2281-2308., Nov. 1, 2013.
Roberts, et al., Systematic Gene Tagging Using CRISPR/Cas9 in Human Stem Cells to Illuminate Cell Organization, Molecular Biology of the Cell, vol. pp. 2854-2874, Oct. 15, 2017.
Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345., Oct. 2000.
Sosic, et al., Enzymatic Formation of PEGylated Oligonucleotides, Bioconjugate Chemistry, vol. 25, No. 2, pp. 433-441., Feb. 201, 2014.
Stein, et al., Inhibition of Vesivirus Infections in Mammalian Tissue Culture with Antisense Morpholino Oligomers, Antisense and Nucleic Acid Drug Development, vol. 11, Issue 5, pp. 317-325., 2001.
Tsai, et al., Guide-Seq Enables Genome-Wide Profiling of Off-Target Cleavage by CRISPR-Cas Nucleases, Nature Biotechnology, vol. 33, No. 2, pp. 187-197, Feb. 1, 2015.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85., Apr. 2011.
U.S. Appl. No. 16/384,612 2019/0345479, filed Apr. 15, 2019 Nov. 14, 2019, Craig Cameron Mello.
U.S. Appl. No. 17/620,437, filed Dec. 17, 2021, Craig Cameron Mello.
Certo, et al. (Jul. 10, 2011) "Tracking Genome Engineering Outcome at Individual DNA Breakpoints", Nature Methods, vol. 8, No. 8, pp. 671-676.

(56) References Cited

OTHER PUBLICATIONS

Dokshin et al. (Nov. 2018) "Robust Genome Editing with Short Single-Stranded and Long, partially Single-Stranded DNA Donors in Caenorhabditis elegans", Genetics, vol. 210, pp. 781-787.
Glaser, et al. (Jul. 12, 2016) "GFP to BFP Conversion: A Versatile Assay for the Quantification of CRISPR/Cas9-mediated Genome Editing", Molecular Therapy—Nucleic Acids, e334, vol. 5, No. 7, pp. 1-4.
International Search Report and Written Opinion received for PCT Patent Application No. PCT/US2019/027531, dated Jul. 8, 2019, 26 Pages.
International Search Report and Written Opinion received for PCT Patent Application No. PCT/US2019/046013, dated Jan. 9, 2020, 17 Pages.
Lee et al. (2017) "Synthetically Modified Guide RNA and Donor DNA are a Versatile Platform for CRISPR-Cas9 Engineering", eLIFE Genes and Chromosomes Human Biology and Medicine, vol. 6, 17 Pages.
Mello, et al. (Dec. 1991) "Efficient Gene Transfer in C. Elegans: Extrachromosomal Maintenance and Integration of Transforming Sequences", EMBO Journal, vol. 10, No. 12, pp. 3959-3970.
Paix, et al. (Sep. 2015) "High Efficiency, Homology-Directed Genome Editing in Caenorhabditis Elegans Using CRISPR-Cas9 Ribonucleoprotein Complexes", Genetics, vol. 201, No. 1, pp. 47-54.
Prior, et al. (Nov. 6, 2017) "Highly Efficient, Rapid and Co-CRISPR-Independent Genome Editing in Caenorhabditis Elegans", G3 (Bethesda), vol. 7, No. 11, pp. 3693-3698.
Renaud et al. (Mar. 8, 2016) "Improved Genome Editing Efficiency and Flexibility Using Modified Oligonucleotides with TALEN and CRISPR-Cas9 Nucleases", Cell Reports, vol. 14, pp. 2263-2272.
Richardson et al. (Mar. 2016) "Enhancing Homology-Directed Genome Editing by Catalytically Active and Inactive CRISPR-Cas9 Using Asymmetric Donor DNA", Nature Biotechnology, vol. 34, No. 3, pp. 339-345.
Suzuki, et al. (Dec. 1, 2016) "In Vivo Genome Editing Via CRISPR/Cas9 Mediated Homology-Independent Targeted Integration", Nature, vol. 540, No. 7631, pp. 144-149.
Lee et al. (2017) "Synthetically Modified Guide RNA and Donor DNA are a Versatile Platform for CRISPR-Cas9 Engineering", eLIFE Genes and Chromosomes Human Biology and Medicine, vol. 6, pp. 1-17.
Supplementary European Search Report and Search Opinion for European Patent Application No. 19788536.1, dated Dec. 20, 2021.
U.S. Appl. No. 17/818,226, filed Aug. 8, 2022, Craig Mello, Compositions And Methods For Improved Gene Editing.
Bhattacharaya et al., A simple genotyping method to detect small CRISPR-Cas9 induced indels by agarose gel electrophoresis, Scientific Reports, Mar. 14, 2019, 9(1): 1-7.
Extended European Search Report for European Patent Application No. 20826984.5 dated Oct. 2, 2023.
Guttierez-Triana et al., "Efficient single-copy HDR by 5' modified long dsDNA donors", eLIFE, 2018, 7: e39468.
Jasin et al., "Repair of Strand Breaks by Homologous Recombination", Cold Spring Harbor Perspectives in Biology, vol. 5, No. 11, Article No. a012740, pp. 1-18, Nov. 2013.
Partial Supplementary European Search Report for European Patent Application No. 20826984.5 dated Jun. 30, 2023.
U.S. Appl. No. 16/384,612 2019/0345479, filed Apr. 15, 2019 Nov. 14, 2019, Craig Mello, Compositions And Methods For Improved Gene Editing.
U.S. Appl. No. 17/620,437 2022/0348912, filed Dec. 17, 2021 Nov. 3, 2022, Craig Mello, Compositions And Methods For Improved Gene Editing.
U.S. Appl. No. 17/818,226 2023/0017203, filed Aug. 8, 2022 Apr. 20, 2023, Craig Mello, Compositions And Methods For Improved Gene Editing.
U.S. Appl. No. 18/332,029, filed Jun. 9, 2023, Craig Mello, Compositions And Methods For Improved Gene Editing.

* cited by examiner

L.H.A- Left homology arm
R.H.A- Right homology arm

COMPOSITIONS AND METHODS FOR IMPROVED GENE EDITING

RELATED APPLICATIONS

This application claims the benefit of priority of U.S. Provisional Application No. 62/658,368, filed on Apr. 16, 2018, and U.S. Provisional Application No. 62/679,315, filed on Jun. 1, 2018, the contents of which are hereby incorporated by reference in their entirety for all purposes.

STATEMENT OF FEDERALLY SPONSORED RESEARCH

This invention was made with government support under Grant Nos. GM058800 and HD078253 awarded by the National Institutes of Health. The Government has certain rights in this invention.

SEQUENCE LISTING

The instant application contains a Sequence Listing which has been submitted electronically in ASCII format and is hereby incorporated by reference in its entirety. Said ASCII copy, created on Feb. 8, 2022, is named 611753_UM9-229_ST25.txt and is 786 bytes in size.

FIELD OF THE INVENTION

The instant disclosure provides novel methods and compositions for gene editing. In particular, the disclosure relates to compositions and methods of making modified nucleic acid donor templates for highly efficient and precise gene editing.

BACKGROUND

In recent years several approaches have been developed for genome editing in eukaryotic systems including mammalian cells, such as somatic or germline cells, zygotes or embryos, plants, rodents, worms, insects, and many other organisms. In all cases a nuclease (clustered regularly interspaced short palindromic repeats [CRISPR]-associated Cas9, Cas12a/Cpf1, transcription activator like effector nuclease [TALEN], zinc finger nuclease (ZFN), etc.) is used to generate a targeted DNA lesion, which is resolved as a precise or imprecise edit by the cell's DNA repair machinery. Both precise and imprecise editing approaches have found applications in gene therapy, agriculture, development of research tools, and elsewhere. Precise genome editing, in which the targeted sequence is re-written in a user-defined fashion requires the introduction of a donor template that the cell machinery can use in gene editing mechanisms such as homology-directed DNA repair (HDR) or homology independent targeted integration (HITI). Routine use of genome editing methodology is currently hampered by the low frequency of precision gene editing in many model organisms and cell lines. This is particularly true of longer donor templates. Accordingly, there exists a need in the art for nucleic acid donor templates with improved gene editing activity.

SUMMARY

The present invention provides compositions and methods for improved gene editing, e.g., via homology-directed repair (HDR) or homology-independent targeted integration (HITI). For example, the compositions and methods of the invention may improve precision gene editing of a diverse array of donor nucleic acids templates, including single-stranded and double-stranded DNA templates of various sizes and lengths. Further, the compositions and methods of the invention can be used in various host organisms and cells, including, but not limited to, human and other mammalian subjects. The methods and compositions are useful in a variety of gene editing and genome engineering strategies and contexts. For example, in some embodiments, the compositions and methods are useful for repairing mutations (e.g., heterozygous mutations) that are widely found in patients having certain diseases (e.g., monogenic recessive diseases). In other embodiments, the compositions and methods are useful for introducing an exogenous gene of interest (GOI) to the genome of a host cells. It will be appreciated, however, that the compositions and methods of the disclosure are not limited to editing a specific gene or mutation.

In certain aspects, the invention provides an isolated nucleic acid donor sequence comprising one or more terminal adaptors and/or terminal adaptor ligand moieties.

In an embodiment, the nucleic acid donor sequence comprises a region having portions of nucleic acid homology to the target sequence.

In an embodiment, the nucleic acid donor sequence is introduced into the target sequence by a homology-independent integration mechanism. In an embodiment, the homology-independent integration mechanism comprises engineering the agent's cleavage site into the nucleic acid donor as is contained within the target sequence.

In an embodiment, the one or more terminal adaptors and/or terminal adaptor ligand moieties are attached to the 5' end and/or 3' end of the nucleic acid donor sequence.

In an embodiment, the one or more terminal adaptors comprise ethylene glycol, polyethylene glycol (PEG), a polyamine having at least two amino groups, an alkanediol, and/or a single stranded RNA (ssRNA). In an embodiment, the ethylene glycol, PEG, polyamine having at least two amino groups, or alkanediol is attached to the ssRNA. In an embodiment, the PEG is tetraethylene glycol or triethylene glycol linker. In an embodiment, the polyamine is spermine. In an embodiment, the ssRNA further comprises one or more modified nucleotides.

In an embodiment, the one or more modified nucleotides are selected from the group consisting of a 2'-O-alkyl modified nucleotide, a 2'-fluoro modified nucleotide, a nucleotide comprising a 5'-phosphorothioate group, a 2'-deoxy-modified nucleotide, a locked nucleotide, a bridged nucleotide, a constrained nucleotide, a bicyclic nucleotide, an abasic nucleotide, a 2'-amino-modified nucleotide, a 2'-alkyl-modified nucleotide, a morpholino nucleotide, a phosphoramidate, a peptide nucleic acid, and a non-natural base comprising nucleotide. In an embodiment, the one or more modified nucleotides are 2'-O-methyl (2'OMe) modified nucleotides.

In an embodiment, the ssRNA is about 1 base in length to about 50 bases in length. In an embodiment, the ssRNA is about 8 bases in length to about 30 bases in length.

In an embodiment, the terminal adaptors can bind a terminal adaptor ligand. In an embodiment, the terminal adaptors can bind the terminal adaptor ligand through nucleic acid base-pairing interactions.

In an embodiment, the terminal adaptor ligand comprises a peptide nucleic acid (PNA), a ssRNA, or a ssDNA.

In an embodiment, the terminal adaptor ligand is attached to a terminal adaptor ligand moiety that confers one or more functionalities to the nucleic acid donor sequence. In an embodiment, the one or more functionalities is selected from the group consisting of tissue targeting, PK-modification, and/or nuclear localization.

In an embodiment, the terminal adaptor ligand moiety is a peptide, a carbohydrate, a lipid, a steroid, or a small molecule.

In an embodiment, the terminal adaptor ligand moiety is a nuclear localization signal (NLS). In an embodiment, the NLS comprises PKKKRK (SEQ ID NO: 1).

In an embodiment, the terminal adaptor ligand is attached to the terminal adaptor ligand moiety through a linker. In an embodiment, the linker is selected from the group consisting of aminoethoxyethoxyacetate (AEEA), aminohexanoic acid, oligo glycine, PEG, amino C6, and amino C12.

In an embodiment, the nucleic acid donor sequence is double stranded.

In an embodiment, the nucleic acid donor sequence is single stranded.

In an embodiment, the single stranded nucleic acid is a single stranded donor oligonucleotide (ssODN).

In an embodiment, the portions of nucleic acid homology are about 20 bases in length to about 1,000 bases in length.

In an embodiment, the nucleic acid donor sequence enhances gene editing (e.g., homology-directed repair (HDR) or homology independent targeted integration (HITI)) relative to a nucleic acid donor sequence comprising the nucleic acid sequence and lacking the terminal adaptors and/or terminal adaptor ligand moieties. In an embodiment, HDR or HITI is enhanced about 2-fold or greater.

In an embodiment, the terminal adaptors and/or terminal adaptor ligand moieties enhance gene editing (e.g., via HDR or HITI) through polymerase blocking. In an embodiment, the terminal adaptors and/or terminal adaptor ligand moieties enhance gene editing (e.g., via HDR or HITI) by promoting resistance to engagement by enzymes that would metabolize nucleic acid donor ends. In an embodiment, the enzymes are selected from the group consisting of polymerases, nucleases, recombinases, and ligases.

In an embodiment, the terminal adaptors and/or terminal adaptor ligand moieties enhance gene editing (e.g., via HDR or HITI) by promoting increased nuclear localization and/or retention. In an embodiment, the terminal adaptors and/or terminal adaptor ligand moieties enhance gene editing by promoting ligation resistance. In an embodiment, the terminal adaptors and/or terminal adaptor ligand moieties enhance gene editing by improving ability to engage repair machinery.

In certain aspects, the invention provides a method of introducing a nucleic acid donor sequence into a target sequence of a genome in a cell, the method comprising: i) contacting the cell with a nucleic acid donor sequence comprising terminal adaptors and/or terminal adaptor ligand moieties; and ii) contacting the cell with an agent that creates a double-stranded break at or near the target sequence.

In an embodiment, the nucleic acid donor sequence comprises a region having portions of nucleic acid homology to the target sequence.

In an embodiment, the nucleic acid donor sequence is introduced into the target sequence by a homology-independent integration mechanism. In an embodiment, the homology-independent integration mechanism comprises engineering the agent's cleavage site into the nucleic acid donor as is contained within the target sequence.

In an embodiment, the one or more terminal adaptors and/or terminal adaptor ligand moieties are attached to the 5' end and/or 3' end of the nucleic acid donor sequence. In an embodiment, the one or more terminal adaptors comprise ethylene glycol, polyethylene glycol (PEG), a polyamine having at least two amino groups, an alkanediol, and/or a single stranded RNA (ssRNA). In an embodiment, the ethylene glycol, PEG, polyamine having at least two amino groups, or alkanediol is attached to the ssRNA. In an embodiment, the PEG is tetraethylene glycol or triethylene glycol linker. In an embodiment, the ssRNA further comprises one or more modified nucleotides. In an embodiment, the one or more modified nucleotides are selected from the group consisting of a 2'-O-alkyl modified nucleotide, a 2'-fluoro modified nucleotide, a nucleotide comprising a 5'-phosphorothioate group, a 2'-deoxy-modified nucleotide, a locked, bridged, constrained or bicyclic nucleotide, an abasic nucleotide, a 2'-amino-modified nucleotide, a 2'-alkyl-modified nucleotide, a morpholino nucleotide, a phosphoramidate, a peptide nucleic acid, and a non-natural base comprising nucleotide. In an embodiment, the one or more modified nucleotides are 2'-O-methyl (2'OMe) modified nucleotides. In an embodiment, the ssRNA is about 1 base in length to about 50 bases in length. In an embodiment, the ssRNA is about 8 bases in length to about 30 bases in length.

In an embodiment, the terminal adaptors can bind a terminal adaptor ligand. In an embodiment, the terminal adaptors can bind the terminal adaptor ligand through nucleic acid base-pairing interactions. In an embodiment, the terminal adaptor ligand comprises a peptide nucleic acid (PNA), a ssRNA, or a ssDNA. In an embodiment, the terminal adaptor ligand is attached to a terminal adaptor ligand moiety that confers one or more functionalities to the nucleic acid donor sequence. In an embodiment, the one or more functionalities is selected from the group consisting of tissue targeting, PK-modification, and/or nuclear localization. In an embodiment, the terminal adaptor ligand moiety is a peptide, a carbohydrate, a lipid, a steroid, or a small molecule.

In an embodiment, the terminal adaptor ligand moiety is a nuclear localization signal (NLS). In an embodiment, the NLS comprises PKKKRK.

In an embodiment, the terminal adaptor ligand is attached to the terminal adaptor ligand moiety through a linker. In an embodiment, the linker is selected from the group consisting of aminoethoxyethoxyacetate (AEEA), aminohexanoic acid, oligo glycine, PEG, amino C6, and amino C12.

In an embodiment, the nucleic acid donor sequence is double stranded.

In an embodiment, the nucleic acid donor sequence is single stranded.

In an embodiment, the single stranded nucleic acid is a single stranded donor oligonucleotide (ssODN).

In an embodiment, the portions of nucleic acid homology are about 20 bases in length to about 1,000 bases in length. In an embodiment, the nucleic acid donor sequence enhances gene editing (e.g., via a homology-directed repair (HDR) or homology independent targeted integration (HITI) mechanism) relative to a nucleic acid donor sequence comprising the nucleic acid sequence and lacking the terminal adaptors and/or terminal adaptor ligand moieties. In an embodiment, the agent is a polypeptide, or a nucleic acid sequence encoding a polypeptide, selected from the group consisting of a zinc finger nuclease (ZFN), a transcription-activator like effector nuclease (TALEN), and an RNA-guided nuclease. In an embodiment, gene editing (e.g., HDR or HITI) is enhanced about 2-fold or greater.

In certain aspects, the invention provides an isolated modified nucleic acid donor sequence comprising one or more terminal adaptors and/or terminal adaptor ligand moieties, wherein the modified nucleic acid donor sequence possesses enhanced HDR or HITI relative to an unmodified nucleic acid donor sequence. In an embodiment, the one or more terminal adaptors and/or terminal adaptor ligand moieties are attached to the 5' end and/or 3' end of the nucleic acid donor sequence. In an embodiment, the one or more terminal adaptors comprise ethylene glycol, polyethylene glycol (PEG), a polyamine having at least two amino groups, an alkanediol, and/or a single stranded RNA (ssRNA). In an embodiment, the ethylene glycol, PEG, polyamine having at least two amino groups, or alkanediol is attached to the ssRNA. In an embodiment, the ssRNA further comprises one or more modified nucleotides.

In an embodiment, the one or more modified nucleotides are selected from the group consisting of a 2'-O-alkyl modified nucleotide, a 2'-fluoro modified nucleotide, a nucleotide comprising a 5'-phosphorothioate group, a 2'-deoxy-modified nucleotide, a locked, bridged, constrained or bicyclic nucleotide, an abasic nucleotide, a 2'-amino-modified nucleotide, a 2'-alkyl-modified nucleotide, a morpholino nucleotide, a phosphoramidate, a peptide nucleic acid, and a non-natural base comprising nucleotide.

In an embodiment, the terminal adaptors can bind a terminal adaptor ligand. In an embodiment, the terminal adaptors can bind the terminal adaptor ligand through nucleic acid base-pairing interactions. In an embodiment, the terminal adaptor ligand comprises a peptide nucleic acid (PNA), a ssRNA, or a ssDNA. In an embodiment, the terminal adaptor ligand is attached to a terminal adaptor ligand moiety that confers one or more functionalities to the nucleic acid donor sequence. In an embodiment, the one or more functionalities is selected from the group consisting of tissue targeting, PK-modification, and/or nuclear localization. In an embodiment, the terminal adaptor ligand moiety is a peptide, a carbohydrate, a lipid, a steroid, or a small molecule.

In certain aspects, the invention provides a genome-editing system comprising: i) a nucleic acid donor sequence comprising terminal adaptors and/or terminal adaptor ligand moieties; and ii) an agent that creates a double-stranded break at or near the target sequence.

In an embodiment, the one or more terminal adaptors and/or terminal adaptor ligand moieties are attached to the 5' end and/or 3' end of the nucleic acid donor sequence.

In an embodiment, the one or more terminal adaptors comprise ethylene glycol, polyethylene glycol (PEG), a polyamine having at least two amino groups, an alkanediol, and/or a single stranded RNA (ssRNA). In an embodiment, the ethylene glycol, PEG, polyamine having at least two amino groups, or alkanediol is attached to the ssRNA. In an embodiment, the PEG is tetraethylene glycol or triethylene glycol linker.

In an embodiment, the ssRNA further comprises one or more modified nucleotides. In an embodiment, the one or more modified nucleotides are selected from the group consisting of a 2'-O-alkyl modified nucleotide, a 2'-fluoro modified nucleotide, a nucleotide comprising a 5'-phosphorothioate group, a 2'-deoxy-modified nucleotide, a locked, bridged, constrained or bicyclic nucleotide, an abasic nucleotide, a 2'-amino-modified nucleotide, a 2'-alkyl-modified nucleotide, a morpholino nucleotide, a phosphoramidate, a peptide nucleic acid, and a non-natural base comprising nucleotide. In an embodiment, the one or more modified nucleotides are 2'-O-methyl (2'OMe) modified nucleotides. In an embodiment, the ssRNA is about 1 base in length to about 50 bases in length. In an embodiment, the ssRNA is about 8 bases in length to about 30 bases in length.

In an embodiment, the terminal adaptors can bind a terminal adaptor ligand. In an embodiment, the terminal adaptors can bind the terminal adaptor ligand through nucleic acid base-pairing interactions. In an embodiment, the terminal adaptor ligand comprises a peptide nucleic acid (PNA), a ssRNA, or a ssDNA. In an embodiment, the terminal adaptor ligand is attached to a terminal adaptor ligand moiety that confers one or more functionalities to the nucleic acid donor sequence. In an embodiment, the one or more functionalities is selected from the group consisting of tissue targeting, PK-modification, and/or nuclear localization. In an embodiment, the terminal adaptor ligand moiety is a peptide, a carbohydrate, a lipid, a steroid, or a small molecule. In an embodiment, the terminal adaptor ligand moiety is a nuclear localization signal (NLS). In an embodiment, the NLS comprises PKKKRK (SEQ ID NO: 1).

In an embodiment, the terminal adaptor ligand is attached to the terminal adaptor ligand moiety through a linker. In an embodiment, the linker is selected from the group consisting of aminoethoxyethoxyacetate (AEEA), aminohexanoic acid, oligo glycine, PEG, amino C6, and amino C12.

In an embodiment, the nucleic acid donor sequence is double stranded.

In an embodiment, the nucleic acid donor sequence is single stranded.

In an embodiment, the single stranded nucleic acid is a single stranded donor oligonucleotide (ssODN).

In an embodiment, the portions of nucleic acid homology are about 20 bases in length to about 1,000 bases in length.

In an embodiment, the nucleic acid donor sequence enhances gene editing (e.g., via a homology-directed repair (HDR) or homology independent targeted integration (HITI) mechanism) relative to a nucleic acid donor sequence comprising the nucleic acid sequence and lacking the terminal adaptors and/or terminal adaptor ligand moieties. In an embodiment, the agent is a polypeptide, or a nucleic acid sequence encoding a polypeptide, selected from the group consisting of a zinc finger nuclease (ZFN), a transcription-activator like effector nuclease (TALEN), and an RNA-guided nuclease. In an embodiment, the gene editing mechanism (e.g., HDR or HITI) is enhanced about 2-fold or greater.

In certain aspects, the invention provides an isolated nucleic acid donor sequence comprising one or more terminal adaptors and/or terminal adaptor ligand moieties attached to the 5' end of the nucleic acid donor sequence.

In one embodiment, the nucleic acid donor sequence comprises a region having portions of nucleic acid homology to the target sequence. in another embodiment, the nucleic acid donor sequence of claim 105, where the nucleic acid donor sequence is introduced into the target sequence by a homology-independent integration mechanism (e.g., the homology-independent integration mechanism comprises engineering the agent's cleavage site into the nucleic acid donor as is contained within the target sequence).

In one embodiment, the one or more terminal adaptors comprise ethylene glycol, polyethylene glycol (PEG), a polyamine having at least two amino groups, an alkanediol, and/or a single stranded RNA (ssRNA). In one embodiment, the ethylene glycol, PEG, polyamine having at least two amino groups, or alkanediol is attached to the ssRNA. In another embodiment, the PEG is tetraethylene glycol or triethylene glycol linker. In another embodiment, the ssRNA further comprises one or more modified nucleotides.

In one embodiment, the one or more modified nucleotides are selected from the group consisting of a 2'-O-alkyl modified nucleotide, a 2'-fluoro modified nucleotide, a nucleotide comprising a 5'-phosphorothioate group, a 2'-deoxy-modified nucleotide, a locked nucleic acid (LNA), a bridged nucleotide, a constrained nucleotide, a bicyclic nucleotide, an abasic nucleotide, a 2'-amino-modified nucleotide, a 2'-alkyl-modified nucleotide, a morpholino nucleotide, a phosphoramidate, a peptide nucleic acid, and a non-natural base comprising nucleotide.

In one embodiment, the one or more modified nucleotides are 2'-O-methyl (2'OMe) modified nucleotides.

In none embodiment, the ssRNA is about 1 base in length to about 50 bases in length or is about 8 bases in length to about 30 bases in length.

In one embodiment, the terminal adaptors can bind a terminal adaptor ligand, e.g., through nucleic acid base-pairing interactions.

In one embodiment, the terminal adaptor ligand comprises a peptide nucleic acid (PNA), a ssRNA, or a ssDNA.

In one embodiment, the terminal adaptor ligand is attached to a terminal adaptor ligand moiety that confers one or more functionalities to the nucleic acid donor sequence. In another embodiment, the one or more functionalities is selected from the group consisting of tissue targeting, PK-modification, and/or nuclear localization. In another embodiment, the terminal adaptor ligand moiety is a peptide, a carbohydrate, a lipid, a steroid, or a small molecule. In another embodiment, the terminal adaptor ligand moiety is a nuclear localization signal (NLS), e.g., PKKKRK (SEQ ID NO: 1).

In one embodiment, the terminal adaptor ligand is attached to the terminal adaptor ligand moiety through a linker. In another embodiment, the linker is selected from the group consisting of aminoethoxyethoxyacetate (AEEA), aminohexanoic acid, oligo glycine, PEG, amino C6, and amino C12.

In certain embodiments, the nucleic acid donor sequence is double stranded or the nucleic acid donor sequence is single stranded, e.g., a single stranded donor oligonucleotide (ssODN).

In certain embodiments, the portions of nucleic acid homology are about 20 bases in length to about 1,000 bases in length.

In certain embodiments, the nucleic acid donor sequence enhances gene editing relative to a nucleic acid donor sequence comprising the nucleic acid sequence and lacking the terminal adaptors and/or terminal adaptor ligand moieties, e.g., gene editing is enhanced about 2-fold or greater.

In certain embodiments, the terminal adaptors and/or terminal adaptor ligand moieties enhance gene editing through polymerase blocking.

In certain embodiments, the terminal adaptors and/or terminal adaptor ligand moieties enhance gene editing by promoting resistance to engagement by enzymes that would metabolize nucleic acid donor ends. In one embodiment, the enzymes are selected from the group consisting of polymerases, nucleases, recombinases, and ligases.

In certain embodiments, the terminal adaptors and/or terminal adaptor ligand moieties enhance gene editing by promoting increased nuclear localization and/or retention.

In certain embodiments, the terminal adaptors and/or terminal adaptor ligand moieties enhance gene editing by promoting ligation resistance.

In certain embodiments, the terminal adaptors and/or terminal adaptor ligand moieties enhance gene editing by improving ability to engage repair machinery.

In certain aspects, the invention provides a molecule comprising the following formula:

R:NN-[DNA]-3D wherein R is optionally present and comprises a terminal ligand joined covalently or by base pairing to a ligand adapter (NN); wherein the NN comprises a non-DNA linker; wherein the DNA is a donor for precision gene editing; and wherein 3D is a 3'-terminal nucleotide comprising an unmodified 3'-OH group, wherein the molecule enhances precision gene editing relative to gene editing mediated by unmodified DNA.

In one embodiment, the non-DNA linker comprises one or more of a non-nucleotide group (e.g., oligoethylene glycol), a native RNA and a modified RNA, and wherein the non-DNA linker is covalently attached to a 5'-terminus of the DNA.

In one embodiment, the DNA comprises a region of homology to DNA sequences in a target cell. In another embodiment, the DNA is chemically modified to maintain or enhance efficient gene editing, e.g., comprising one or more internal phosphate modifications.

In one embodiment, a double-stranded nucleic acid sequence comprising the molecule described above in one or both strands, wherein the double-stranded nucleic acid sequence enhances precision gene editing relative to gene editing mediated by unmodified DNA.

In certain aspects, the invention provides an isolated asymmetric double-stranded nucleic acid donor sequence comprising i) a first region having portions of nucleic acid homology to a target sequence; and ii) a second region having portions of nucleic acid homology to a target sequence, wherein one or both of the first region and second region comprise single-stranded nucleotide portions.

In one embodiment, the portions of nucleic acid homology are about 20 bases in length to about 1,000 bases in length.

In one embodiment, the first region is 0-150 nucleotides in length and the second region is 0-150 nucleotides in length.

In one embodiment, the first region is 120 nucleotides in length and the second region is 35 nucleotides in length.

In one embodiment, the first region is 120 nucleotides in length and the second region is 0 nucleotides in length.

In one embodiment, the single-stranded nucleotide portions are about 1 to 150 nucleotides in length.

In one embodiment, the asymmetric double-stranded nucleic acid donor sequence does not comprise a modified nucleotide, a terminal adaptor, or a terminal adaptor ligand moiety.

In certain aspects, the invention provides a method of synthesizing an asymmetric double-stranded nucleic acid donor sequence as recited above, the method comprising the steps of: a) generating a first double-stranded nucleic acid donor sequence comprising a first region having portions of nucleic acid homology to a target sequence of a first nucleotide length and a second region having portions of nucleic acid homology to a target sequence of a second nucleotide length; b) generating a second double-stranded nucleic acid donor sequence comprising a first region having portions of nucleic acid homology to a target sequence of the second nucleotide length and a second region having portions of nucleic acid homology to a target sequence of the first nucleotide length; c) mixing the first double-stranded nucleic acid donor sequence of step a) and the second double-stranded nucleic acid donor sequence of step b) under conditions in which the double-stranded nucleic acids unwind and reanneal; and d) isolating the asymmetric double-stranded nucleic acid donor sequence.

In one embodiment, the conditions in which the double-stranded nucleic acids unwind and reanneal comprise heating a mixture of the first double-stranded nucleic acid donor sequence and the second double-stranded nucleic acid donor sequence to about 95° C. for a time sufficient to unwind the double-stranded nucleic acids, followed by cooling the mixture for a time sufficient to allow the double-stranded nucleic acids to reanneal.

In certain aspects, the invention provides a method of reducing off-target integration of a nucleic acid donor sequence into a target sequence of a genome in a cell, the method comprising: i) contacting the cell with a nucleic acid donor sequence comprising terminal adaptors and/or terminal adaptor ligand moieties; and ii) contacting the cell with an agent that creates a double-stranded break at or near the target sequence.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 11C depicts editing efficiency in *C. elegans* with a modified DNA donor containing a 2'-OMe-modified RNA and a 12-subunit PEG moiety.

FIG. 24A depicts a schematic of the GuideSeq protocol.

FIG. 24B depicts the total number of unique reads from the GuideSeq analysis with three different types of 34 bp double-stranded DNA donors without homology arms.

DETAILED DESCRIPTION

Figure 1A:
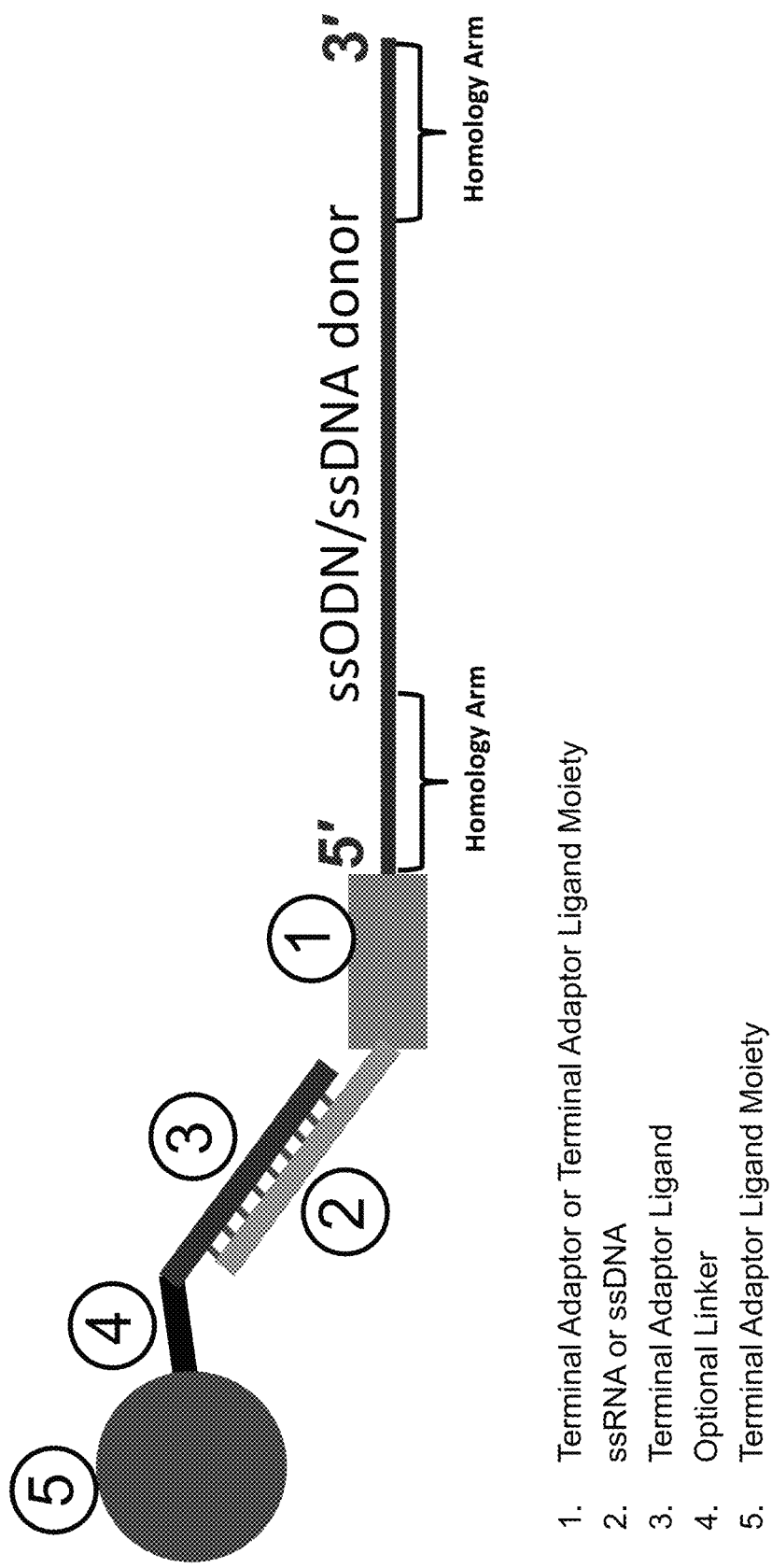
FIG. 1A-FIG. 1B depict a schematic of an exemplary single stranded (single stranded donor oligonucleotide (ssODN) or ssDNA) chimeric DNA donor template (FIG. 1A) and a double stranded chimeric DNA donor template (FIG. 1B).

Gene editing technology holds much promise for personalized medicine, for example, to repair particular mutations or introduce exogenous genes that "rescue" the deleterious effects of a mutation. In essence, gene editing takes place in two steps: inducing a double-stranded break (DSBs) or other genetic lesion, e.g., using nucleases such as Cas9, and repairing the SSBs or DSBs by a repair mechanism. The current pre-clinical development of gene editing technology for therapeutic use can be generally categorized into two strategies: gene disruption that is protective (e.g., CCR4 disruption for HIV protection) and precise repairing of a known mutation. However, the efficacy of current methods for gene editing is hampered by the low frequency or efficiency of the repair mechanism.

"Homology-directed repair" or "HDR" is a mechanism to repair double stranded DNA breaks in cells. HDR generally relies on the process of homologous recombination, whereby stretches of nucleic acid sequence homology are used to repair the double stranded DNA break. During HDR, a strand of the homologous sequence of a nucleic acid donor invades, or hybridizes, with a resected portion of the cut DNA. A DNA polymerase, using the resected DNA as a primer, elongates the cut DNA, using the invaded donor sequence as a template. After elongation and break repair, the new sequence at the site of the cut possesses whatever sequence was present in the nucleic acid donor used in the repair process. The process of HDR is further described in Jasin et al. (Cold Spring Harb. Perspect. Biol. 2013 November; 5(11): a012740), incorporated herein by reference.

"Homology-independent targeted integration" or "HITI" is a mechanism to integrate a nucleic acid donor sequence into the site of a double stranded break in cells. HITI utilizes the endogenous non-homologous end joining (NHEJ) mechanism to achieve the integration. A double stranded break is produced by a nuclease (e.g., CRISPR gene editing system comprising a CRISPR nuclease and guide RNA). The nucleic acid donor sequence is designed such that integration only occurs in the proper, forward direction. Integration events in the reverse direction will be cut again the nuclease. Non-integration events will also be cut again by the nuclease. The process of HITI is further described in Suzuki et al. (Nature 2016 December; 540(7631): 144-149), incorporated herein by reference.

The methods and compositions of the invention address the limitations of current gene editing mechanisms (e.g., HDR or HITI) by providing novel modified nucleic acid donor templates which improve, for example, the efficiency, efficacy and/or precision of gene editing in vitro, ex vivo or in vivo. Without wishing to be bound by theory, the modified nucleic acid donor templates of the invention possess enhanced precision gene editing due to increased potency of the donor. Increased potency may be achieved through one or a combination of the following mechanisms: 1) resistance to engagement by enzymes that would metabolize nucleic acid donor ends, including, but not limited to, polymerases, nucleases, recombinases, and ligases; 2) increased nuclear localization and/or retention; 3) ligation resistance, which would leave more free ends of the nucleic acid donor available to serve as a template; 4) polymerase blocking, which may promote template switching; and/or 5) improved ability to engage repair machinery by making nucleic acid donor homology arms more accessible for strand invasion.

The compositions and methods may be used to repair mutations (e.g., compound heterozygous mutations) that are associated with certain diseases (e.g., monogenic recessive diseases). In some aspects, the modified nucleic acid donor templated may be employed with gene editing complexes (e.g., CRISPR/Cas system) to enable genome engineering at specific nucleotide positions in a homologous target nucleic acid of a host cell (e.g., homologous chromosomes that are compound heterozygous at a particular allele). In some aspects, the disclosure provides a method for targeted gene editing, the method comprising delivering to a cell (e.g., a cell of a disease subject) at least one component of a recombinant gene-editing complex together with the modified nucleic acid donor template, under conditions such that the recombinant gene editing complex induces a genetic lesion (e.g., nick or double stranded break) in a target site in the chromosome, and the donor template of the invention mediates a repair mechanism (e.g., HDR or HITI), thereby repairing the disease mutation.

Generally, nomenclature used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

As used herein, the terms "nucleic acid donor" or "nucleic acid donor template" or "donor template" or "donor sequence" or "donor" or "nucleic acid insert" or "insert" refer to any nucleic acid sequence, e.g., deoxyribonucleic acid, that may be used as a repair template in the repair mechanism (e.g., homology-directed repair (HDR) or homology independent targeted integration (HITI)). The nucleic acid donor may be double stranded or single stranded, e.g., double stranded DNA (dsDNA) or single stranded DNA (ssDNA). The nucleic acid donors of the disclosure may comprise varying polynucleotide lengths. In certain embodiments, the nucleic acid donor may be less than about 100 nucleotides in length, about 100 nucleotides in length, about 200 nucleotides in length, about 300 nucleotides in length, about 400 nucleotides in length, about 500 nucleotides in length, about 600 nucleotides in length, about 700 nucleotides in length, about 800 nucleotides in length, about 900 nucleotides in length, about 1000 nucleotides in length, or greater than about 1000 nucleotides in length. A nucleic acid donor of less than or equal to 200 nucleotides in length may also be referred to as a "short" nucleic acid donor. In certain embodiments, the nucleic acid donor is a single stranded donor oligonucleotide (ssODN). The nucleic acid donors to be inserted into the genome of a cell may be of any nucleotide length as needed by the skilled practitioner. For example, but in no way limiting, the nucleotide portion may be as short as a single nucleotide or greater than ten kilobases.

In an embodiment, the nucleic acid donors of the disclosure comprise a nucleotide sequence to be inserted into the genome of a cell, for example, an exogenous sequence to be inserted into the genome of a cell. The exogenous sequence may comprise a gene. The gene may encode for a protein, such as a therapeutic protein or a selectable marker protein. In certain embodiments, the selectable marker may encode for a selectable marker protein that confers resistance to an agent that reduces cell growth or causes cell death. Examples of such agents, included, but not limited to, ampicillin, blasticidin, bleomycin, chloramphenicol, gentamycin, hygromycin, kanamycin, lincomycin, methotrexate, neomycin, phosphinothricin, puromycin, tetracyclin, and zeocin. In other embodiments, the selectable marker may encode a fluorescent or luminescent protein (e.g., luciferase or GFP). The gene may be derived from the same species organism of the cell in which the gene is to be inserted. The gene may be derived from a different species organism of the cell in which the gene is to be inserted. The gene may be a chimeric sequence comprising sequences of multiple species. The nucleic acid donor may comprise a sequence that encodes for a non-coding RNA. Examples of non-coding RNAs include, but are not limited to, transfer RNAs (tRNAs), ribosomal RNAs (rRNAs), small RNAs such as siRNA, miRNA, piRNA, snoRNA, snRNA, exosomal RNA (exRNA). The nucleic acid donor may comprise a sequence that is not expressed. The nucleic acid donor may comprise a sequence that reduces or eliminates the expression of an endogenous gene in the cell.

In the case of HDR-mediated gene editing, the nucleic acid donors of the disclosure further comprise homology arms at the 5' end and 3' end, for example, a first and second homology arm. The homology arms are nucleic acid sequences that share sufficient homology with a target site in the genome of a cell to mediate HDR. Each homology arm may comprise varying polynucleotide lengths. It will be understood to those of skill in the art that homology arm nucleic acid sequences are an extension of the existing nucleic acid donor sequence as described above.

In certain embodiments the first homology arm may be about 20 nucleotides in length to about 1000 nucleotides in length. In certain embodiments the first homology arm may be less than about 20 nucleotides in length, about 20 nucleotides in length, about 30 nucleotides in length, about 40 nucleotides in length, about 50 nucleotides in length, about 60 nucleotides in length, about 70 nucleotides in length, about 80 nucleotides in length, about 90 nucleotides in length, about 100 nucleotides in length, about 200 nucleotides in length, about 300 nucleotides in length, about 400 nucleotides in length, about 500 nucleotides in length, about 600 nucleotides in length, about 700 nucleotides in length, about 800 nucleotides in length, about 900 nucleotides in length, about 1000 nucleotides in length, or greater than about 1000 nucleotides in length.

In certain embodiments the second homology arm may be about 20 nucleotides in length to about 1000 nucleotides in length. In certain embodiments the second homology arm may be less than about 20 nucleotides in length, about 20 nucleotides in length, about 30 nucleotides in length, about 40 nucleotides in length, about 50 nucleotides in length, about 60 nucleotides in length, about 70 nucleotides in length, about 80 nucleotides in length, about 90 nucleotides in length, about 100 nucleotides in length, about 200 nucleotides in length, about 300 nucleotides in length, about 400 nucleotides in length, about 500 nucleotides in length, about 600 nucleotides in length, about 700 nucleotides in length, about 800 nucleotides in length, about 900 nucleotides in length, about 1000 nucleotides in length, or greater than about 1000 nucleotides in length.

In certain embodiments, the first and second homology arm of the nucleic acid donor may comprise different nucleotide lengths. As an example for illustrative purposes, but in no way limiting, the homology arm at the 5' end of the nucleic acid donor (the first homology arm) may be 100 nucleotides in length and the homology arm at the 3' end of the nucleic acid donor (the second homology arm) may be 150 nucleotides in length.

Terminal Adaptors

As used herein, the term "terminal adaptor" refers to a heterologous 5' end and/or 3' end modification to the nucleic acid donor. In certain embodiments, the terminal adaptor enhances HDR efficiency in an HDR assay as compared to a nucleic acid donor lacking a 5' end and/or 3'end modification. In certain embodiments, the terminal adaptor blocks or inhibits DNA polymerase extension, elongation and/or initiation (e.g., in a PCR assay). In certain embodiments, the terminal adaptor is a non-nucleotide moiety (e.g., a non-nucleotide polymeric moiety). In other embodiments, the terminal adaptor is a single stranded oligonucleotide (e.g., a single stranded oligonucleotide lacking complementarity to the nucleic acid donor). In certain embodiments, the terminal adaptor may comprise a polyethylene glycol (PEG) chain containing multiple ethylene glycol units. In an embodiment, the PEG chain comprises 3 or 4 ethylene glycol units, also referred to as triethylene glycol or tetraethylene glycol, both of which may be abbreviated as TEG. In an embodiment, the PEG chain comprises 2-100 or more ethylene glycol units. In an embodiment, the PEG chain comprises 2-20, 20-40, 40-60, 60-80, 80-100, or 100 or more ethylene glycol units. In an embodiment, the PEG chain comprises 2, 3, 4, 5, 6, 7, 8, 9, 10, 11, 12, 13, 14, 15, 16, 17, 18, 19, or 20 ethylene glycol units. In an embodiment, the terminal adaptor may comprise a single ethylene glycol unit.

The terminal adaptor may comprise a polyamine having at least two amino groups, such as putrescine, spermidine, spermine, diamino ethylene, 1,4,8 triamino octane, and the like.

The terminal adaptor may comprise an alkanediol, where the diols may be germinal, vicinal, 1,3 diols, 1,4 diols, 2,4, diols and the like.

The terminal adaptor may be up to 18 atoms in length comprising moieties selected from alky, aryl, hydroxyl, alkoxy, ether, heteroaryl, phosphorous, alkylamino, guanidinyl, amidinyl, amide, ester, carbonyl, sulfide, disulfide, carbonyl, carbamate, phosphordiamidate, phosphorothioate, piperazine, phosphodiester, and heterocyclyl.

The terminal adaptor may comprise a single stranded RNA (ssRNA) sequence. In an embodiment, the ssRNA adaptor may comprise one or more modified nucleotides, including, but not limited to, 2'-O-alkyl modified nucleotide, such as a 2'-O-methyl modified nucleotide, a 2'-fluoro modified nucleotide, a nucleotide comprising a 5'-phosphorothioate group, a 2'-deoxy-modified nucleotide, a locked nucleic acid (LNA), a bridged nucleotide, a constrained nucleotide, a bicyclic nucleotide, an abasic nucleotide, a 2'-amino-modified nucleotide, a 2'-alkyl-modified nucleotide, a morpholino nucleotide, a phosphoramidate, a peptide nucleic acid (PNA), and a non-natural base comprising nucleotide. In a particular embodiment, the ssRNA adaptor comprises 2'-O-methyl (2'OMe) modified nucleotides.

Figure 17:
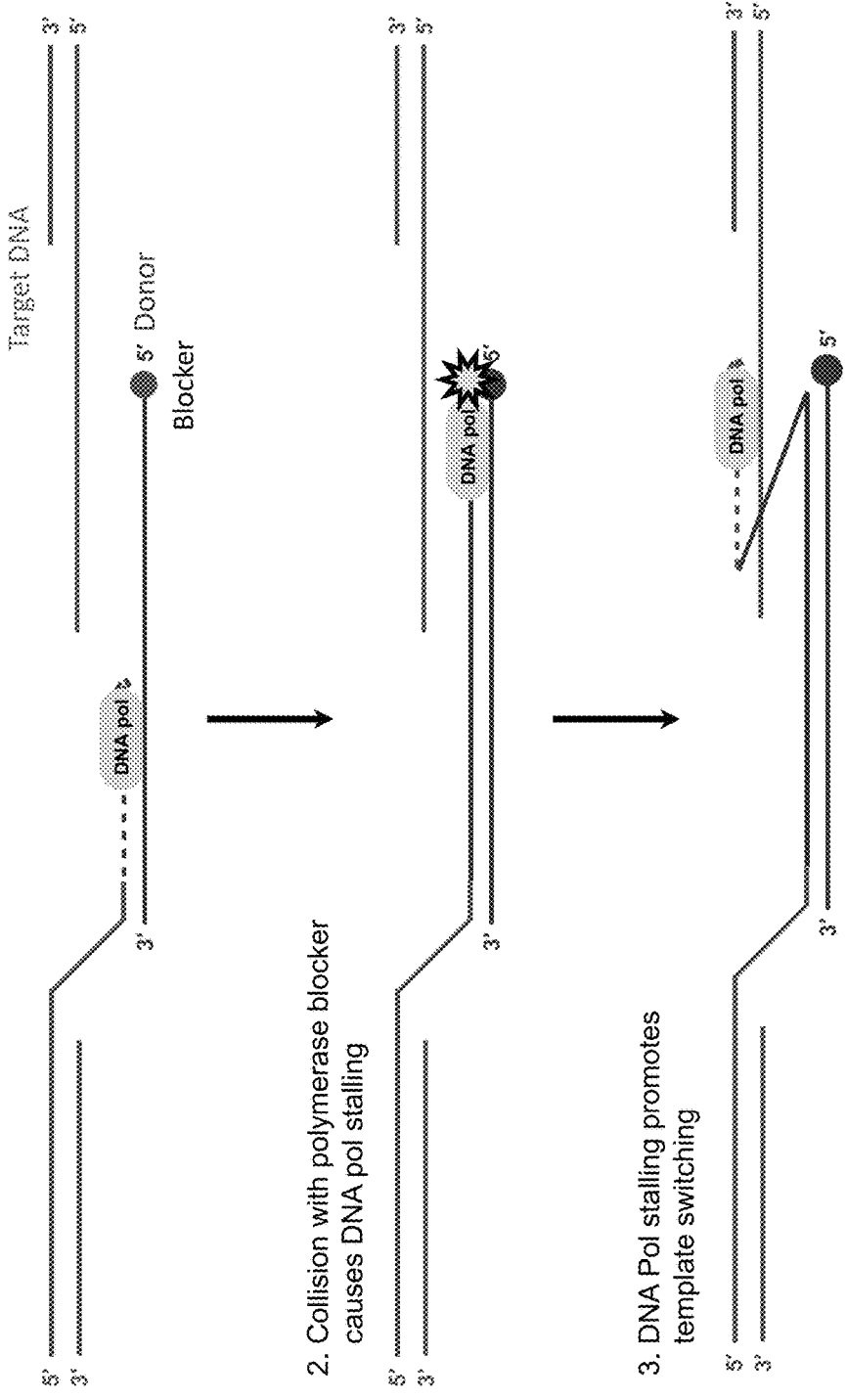
FIG. 17 depicts a schematic outlining one or several mechanisms for enhancing HDR, wherein a DNA donor template is modified such that a DNA polymerase is blocked and template switching occurs.

The ssRNA adaptor may comprise varying nucleotide lengths. Any length of ssRNA necessary to enhance gene editing may be used. For example, a single RNA nucleotide may be sufficient as a terminal adaptor to enhance precision gene editing. Without being bound by theory, a single RNA nucleotide may act as a polymerase blocker, thus contributing to enhanced precision gene editing (see FIG. 17). In certain embodiments, the ssRNA adaptor may be about 1-100 nucleotides in length. In certain embodiments, the ssRNA adaptor may be about 1-50 nucleotides in length. In certain embodiments, the ssRNA adaptor may be about 8-30 nucleotides in length. In certain embodiments, the ssRNA adaptor may be about 10-20 nucleotides in length. In certain embodiments, the ssRNA adaptor may be less than about 10 nucleotides in length, about 10 nucleotides in length, about 15 nucleotides in length, about 20 nucleotides in length, about 25 nucleotides in length, about 30 nucleotides in length, about 35 nucleotides in length, about 40 nucleotides in length, about 45 nucleotides in length, about 50 nucleotides in length, or greater than about 50 nucleotides in length.

The terminal adaptors may comprise any one or more of the above recited terminal adaptors. The terminal adaptors may be "multivalent" or "multivalent terminal adaptors". The multivalent terminal adaptor may comprise two or more terminal adaptor units, linked together in tandem, and further linked to the homology arms of the nucleic acid donor. For example, but in no way limiting, the multivalent terminal adaptors may comprise, from 5' to 3', a ssRNA terminal adaptor linked to a PEG terminal adaptor, further linked to the homology arm of the nucleic acid donor. By way of further example, the multivalent terminal adaptors may comprise, from 5' to 3', a ssRNA terminal adaptor linked to a spermine terminal adaptor linked to a PEG terminal adaptor, further linked to the homology arm of the nucleic acid donor. In a particular embodiment, the terminal adaptor comprises a 2'-OMethyl-modified ssRNA linked to a TEG (2'-OMe-RNA::TEG). In a particular embodiment, the terminal adaptor comprises a 2'OMethyl-modified ssRNA linked to a spermine (2'-OMe-RNA::spermine).

Figure 1B:
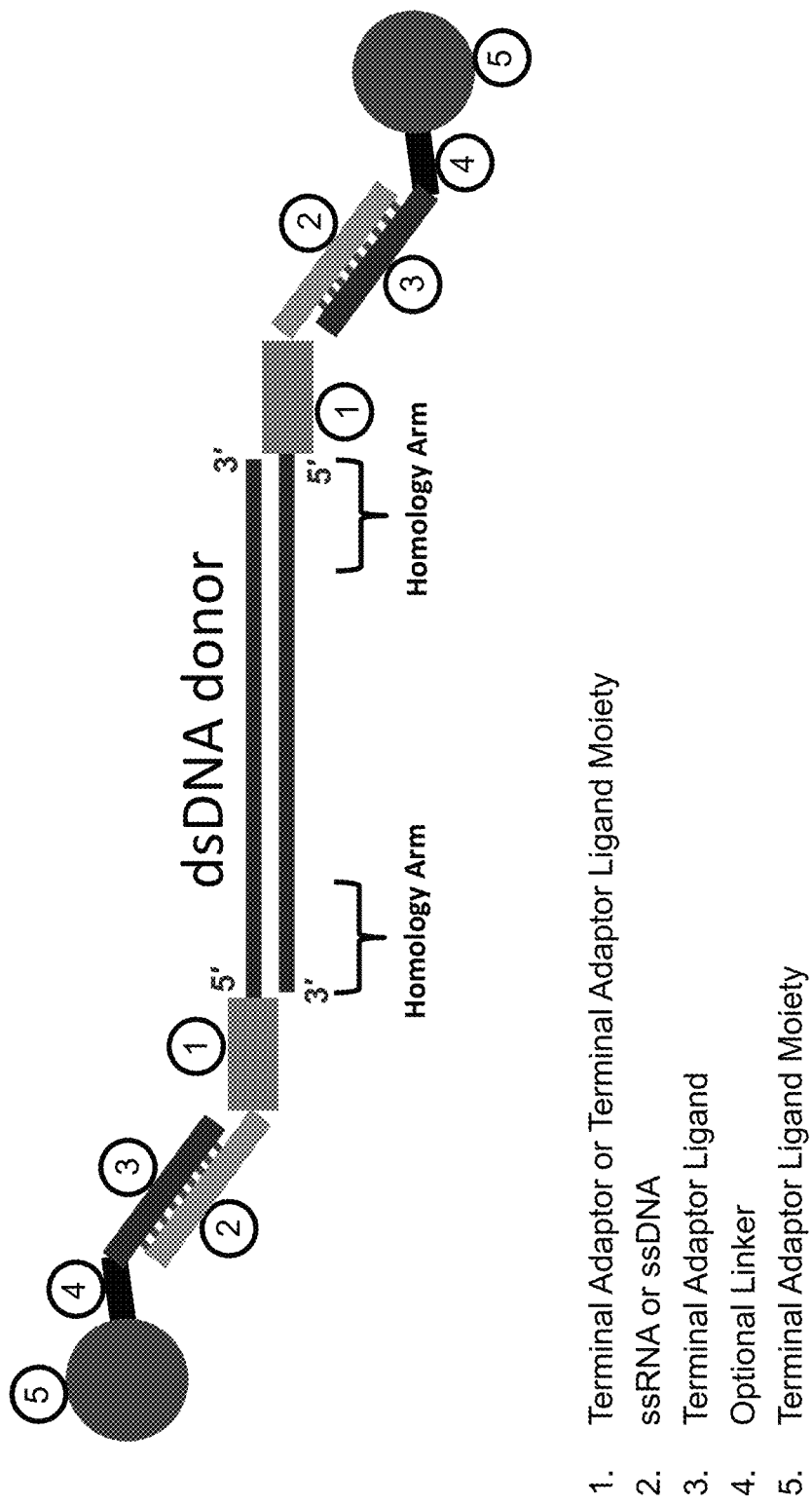

In the case of a double stranded nucleic acid donor, e.g., a dsDNA donor template, terminal adaptors may be linked to the 5' end of the top, or the sense strand, and the 5' end of the bottom, or antisense strand (See, for example, FIG. 1B). Alternatively, the terminal adaptor may be linked to only one of the two strands, for example the 5' end of the top strand or the 5' end of the bottom strand. In certain embodiments, only the 5' end of the nucleic acid donor contains a terminal adaptor. The terminal adaptors may be further linked to the 3' end of the dsDNA template. For example, the 3' end of the top and/or bottom strand may be linked to the terminal adaptors. In certain embodiments, only the 3' end of the nucleic acid donor contains a terminal adaptor.

In the case of a single stranded nucleic acid donor, e.g., a ssDNA donor template, terminal adaptors may be linked to the 5' end and/or the 3' end.

The terminal adaptors of the disclosure are operably linked, or attached, to the nucleic acid donor sequences, i.e., the first and/or second homology arm of the nucleic acid donor sequences. In certain embodiments, the terminal adaptors are covalently linked to the nucleic acid donor. In certain embodiments, the terminal adaptors are non-covalently linked to the nucleic acid donor. In certain embodiments, the terminal adaptors are linked to a modified 5' terminal nucleotide of the nucleic acid donor. In certain embodiments, the terminal adaptors are linked to the 5' phosphate of the terminal nucleotide of the nucleic acid donor. In certain embodiments, the terminal adaptors are linked to the 2' ribose of the terminal nucleotide of the nucleic acid donor. In certain embodiments, the terminal adaptors are linked to the nucleotide base of the terminal nucleotide of the nucleic acid donor.

HDR Assays

The terminal adaptors of the disclosure serve to enhance HDR of the nucleic acid donors. The terminal adaptors may enhance HDR of the nucleic acid donors through one or a combination of the following ways: 1) resistance to engagement by enzymes that would metabolize nucleic acid donor ends, including, but not limited to, polymerases, nucleases, recombinases, and ligases; 2) increased nuclear localization and/or retention; 3) ligation resistance, which would leave more free ends of the nucleic acid donor available to serve as a template; 4) polymerase blocking, which may promote template switching; and/or 5) improved ability to engage repair machinery by making nucleic acid donor homology arms more accessible for strand invasion.

Terminal adaptors that enhance HDR of a nucleic acid donor may be screened by several assays known in the art. Panels of different terminal adaptors may be synthesized and attached to a nucleic acid donor sequence. The nucleic acid donor, encoding for a fluorescent protein, may be inserted into the genome of a cell through HDR. The fluorescence may then be monitored by microscopy to identify successful integration of the nucleic acid donor.

Terminal adaptors that enhance HDR of a nucleic acid donor may be screened with a modified version of the "traffic light" reporter (TLR) assay, as described in Certo et al. Nature Methods. 8: 671-676 (2011). In this assay, a double strand break is introduced into a non-functional GFP coding sequence followed by a frameshifted mCherry reporter. Imprecise repair via non-homologous end-joining (NHEJ) restores frame in a subset of indels, resulting in mCherry (red) fluorescence. Conversely, precisely templated repair via HDR of the same lesion results in GFP (green) fluorescence. Using flow cytometry, the percentage of cells expressing either GFP (HDR) or mCherry (NHEJ) among the total number of cells can be easily quantified. In this manner, panels of different terminal adaptors may be tested for their ability to enhance HDR by monitoring GFP positive cells in the above recited TLR assay. The HDR assays may be conducted in vivo, ex vivo, or in vitro.

In certain embodiments, the modified donor templates of the invention exhibit enhanced HDR efficiency in a HDR assay as compare to a suitable control (e.g., a donor template lacking the terminal adaptor ligands of the invention). In certain embodiments, the modified donor templates exhibit an improvement in HDR efficiency of at least 10% (e.g., 10%, 15%, 20%, 25%, 30%, 35%, 40%, 45%, 50%, 60%, 70%, 80%, 90%, 95% or more) as compared to the suitable control.

Terminal Adaptor Ligands

As used herein, the term "terminal adaptor ligand" refers to an agent which binds to the terminal adaptor. In an embodiment, the terminal adaptor ligand binds to the terminal adaptor through nucleic acid base-pairing interactions between a single stranded oligonucleotide (e.g., ssRNA) terminal adaptor and the terminal adaptor ligand. The terminal adaptor ligand may comprise a polynucleotide sequence. The terminal adaptor ligand may comprise a polynucleotide sequence with one or more modified nucleotides. In an embodiment, the terminal adaptor ligand is a peptide nucleic acid (PNA) that is sufficiently complementary to the ssRNA terminal adaptor to bind. In an embodiment, the terminal adaptor ligand is also a ssRNA that is sufficiently complementary to the ssRNA terminal adaptor to bind. In an embodiment, the terminal adaptor ligand is a ssDNA that is sufficiently complementary to the ssRNA terminal adaptor to bind.

The terminal adaptor ligand may further comprise an additional moiety attached to the terminal adaptor ligand. The terminal adaptor ligand may be attached to the moiety via a linker. In certain embodiments, the linker is selected from the group consisting of aminoethoxyethoxyacetate (AEEA), aminohexanoic acid, oligo glycine, PEG, amino C6, and amino C12. In certain embodiments, the terminal adaptor ligand may be attached to the moiety without a linker.

Terminal Adaptor Ligand Moieties

As used herein, the term "moiety" or "terminal adaptor ligand moiety" refers to a functional group either 1) attached to the terminal adaptor ligand or 2) directly attached to the nucleic acid donor sequence, that may be useful for conferring one or more additional functionalities to the nucleic acid donor template. Functionalities include, but are not limited to, tissue targeting, PK-modification, and/or nuclear localization. The moiety may be a peptide, a carbohydrate, a lipid, a steroid, or a small molecule. In addition to one or more of the functionalities listed above, when the terminal adaptor ligand moiety is attached directly to the nucleic acid donor without the terminal adaptor ligand, the terminal adaptor ligand moiety may also enhance HDR of the nucleic acid donor.

In one embodiment, the moiety has an affinity for low density lipoprotein and/or intermediate density lipoprotein. In a related embodiment, the moiety is a saturated or unsaturated moiety having fewer than three double bonds.

In another embodiment, the moiety has an affinity for high density lipoprotein. In a related embodiment, the moiety is a polyunsaturated moiety having at three or more double bonds (e.g., having three, four, five, six, seven, eight, nine or ten double bonds). In a particular embodiment, the moiety is a polyunsaturated moiety having three double bonds. In a particular embodiment, the moiety is a polyunsaturated moiety having four double bonds. In a particular embodiment, the moiety is a polyunsaturated moiety having five double bonds. In a particular embodiment, the moiety is a polyunsaturated moiety having six double bonds.

In another embodiment, the moiety is selected from the group consisting of fatty acids, steroids, secosteroids, lipids, gangliosides and nucleoside analogs, and endocannabinoids.

In another embodiment, the moiety is a neuromodulatory lipid, e.g., an endocannabinoid. Non-limiting examples of endocannabinoids include: anandamide, arachidonoylethanolamine, 2-Arachidonyl glyceryl ether (noladin ether), 2-Arachidonyl glyceryl ether (noladin ether), 2-Arachidonoylglycerol, and N-Arachidonoyl dopamine.

In another embodiment, the moiety is an omega-3 fatty acid. Non-limiting examples of omega-3 fatty acids include: hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, timnodonic acid), heneicosapentaenoic acid (HPA), docosapentaenoic acid (DPA, clupanodonic acid), docosahexaenoic acid (DHA, cervonic acid), tetracosapentaenoic acid, and tetracosahexaenoic acid (nisinic acid).

In another embodiment, the moiety is an omega-6 fatty acid. Non-limiting examples of omega-6 fatty acids include: linoleic acid, gamma-linolenic acid (GLA), eicosadienoic acid, dihomo-gamma-linolenic acid (DGLA), arachidonic acid (AA), docosadienoic acid, adrenic acid, docosapentaenoic acid (osbond acid), tetracosatetraenoic acid, and tetracosapentaenoic acid.

In another embodiment, the moiety is an omega-9 fatty acid. Non-limiting examples of omega-9 fatty acids include: oleic acid, eicosenoic acid, mead acid, erucic acid, and nervonic acid.

In another embodiment, the moiety is a conjugated linolenic acid. Non-limiting examples of conjugated linolenic acids include: α-calendic acid, β-calendic acid, jacaric acid, α-eleostearic acid, β-eleostearic acid, catalpic acid, and punicic acid.

In another embodiment, the moiety is a saturated fatty acid. Non-limiting examples of saturated fatty acids include: caprylic acid, capric acid, docosanoic acid, lauric acid, myristic acid, palmitic acid, stearic acid, arachidic acid, behenic acid, lignoceric acid, and cerotic acid.

In another embodiment, the moiety is an acid selected from the group consisting of: rumelenic acid, α-parinaric acid, β-parinaric acid, bosseopentaenoic acid, pinolenic acid, and podocarpic acid.

In another embodiment, the moiety is selected from the group consisting of: docosanoic acid (DCA), docosahexaenoic acid (DHA), and eicosapentaenoic acid (EPA).

In another embodiment, the moiety is a secosteroid. In a particular embodiment, the moiety is calciferol.

In another embodiment, the moiety is an alkyl chain, a vitamin, a peptide, or a bioactive conjugate (including but not limited to: glycosphingolipids, polyunsaturated fatty acids, secosteroids, steroid hormones, sterol lipids and the like).

In another embodiment, the moiety is a lipophilic moiety selected from the group consisting of cholesterol, vitamin E, vitamin K, vitamin A, folic acid, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine.

The moiety attached to the terminal adaptor ligand may be useful for cell or tissue targeting. Moieties useful for targeting include, but are not limited to, a thyrotropin, melanotropin, lectin, glycoprotein, surfactant protein A, mucin carbohydrate, multivalent lactose, multivalent galactose, N-acetyl-galactosamine (GalNAc), N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g., cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG, MPEG, $[MPEG]_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP or AP.

In certain embodiments, the moiety is a nuclear localization signal (NLS). Any NLS known in the art may be used as a moiety linked to the terminal adaptor ligand. In certain embodiments, the NLS comprises the peptide sequence of PKKKRK (SEQ ID NO: 1). Additional examples of NLSs may be found in Kosugi et al. J. Biol. Chem. 284: 478-485 (2009) and Bernhofer et al. Nucleic Acids Research 46: D503-D508 (2017).

Modified Nucleotides

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example, the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

In certain embodiments, the above recited modified nucleotides may be incorporated into the nucleic acid donor sequences of the disclosure. In certain embodiments, the above recited modified nucleotides may be incorporated into the terminal adaptors and/or terminal adaptor ligands of the disclosure.

Gene Editing Complexes

As used herein, "gene editing complex" refers to a biologically active molecule (e.g., a protein, one or more proteins, a nucleic acid, one or more nucleic acids, or any combination of the foregoing) configured for adding, disrupting or changing genomic sequences (e.g., a gene sequence) by causing a genetic lesion (e.g., double stranded break (DSB)) in a target DNA or other target nucleic acid. In certain embodiments, the gene editing complex may further comprise the modified DNA donor templates of the disclosure, e.g., to enhance the efficacy of gene editing at the site of the genetic lesion in the genome of a cell. The genetic lesion (e.g., DSB) may be introduced in a number of ways known in the art. Examples of gene editing complexes include but are not limited nucleases such as transcription activator-like effector nucleases (TALENs), zinc finger nucleases (ZFNs), engineered meganuclease re-engineered homing endonucleases, the CRISPR/Cas system, and meganucleases (e.g., Meganuclease I-SceI). In some embodiments, a gene editing complex comprises proteins or molecules (e.g., components) related to the CRISPR/Cas system, including but not limited to Cas9, Cas6, dCas9, CRISPR RNA (crRNA), trans-activating crRNA (tracrRNA), and variants thereof. In some embodiments, the Cas protein is a Cpf1 protein, or a variant thereof.

In certain embodiments, the gene editing complex comprises a nuclease that introduces a double-stranded break (DSB) to facilitate gene editing. However, it will be appreciated that the gene editing complex may be configured to introduce single stranded nicks or single stranded breaks (SSBs) at the target site in the genome of a cell. For example, two nucleases may be used to introduce two SSBs at two adjacent target sites in the genome of a cell. By introducing two adjacent SSBs, a double stranded break is created.

As used herein, the terms "endonuclease" and "nuclease" refer to an enzyme that cleaves a phosphodiester bond or bonds within a polynucleotide chain. Nucleases may be naturally occurring or genetically engineered. Genetically engineered nucleases are particularly useful for genome editing and are generally classified into four families: zinc finger nucleases (ZFNs), transcription activator-like effector nucleases (TALENs), meganucleases (e.g., engineered meganucleases) and RNA guides nucleases such as the CRISPR-associated proteins (Cas nucleases).

Meganucleases

A meganuclease, such as a homing endonuclease, refers to a double-stranded endonuclease having a polynucleotide recognition site of 14-40 base pairs, which can be either monomeric or dimeric. Meganucleases can be designed and predicted according to the procedures in US 2014/0121115 can be used in the present methods. A "custom-made meganuclease" refers to a meganuclease derived from a parental meganuclease that possesses recognition and/or cleavage that is altered from the parental meganuclease. Exemplary meganucleases include, but are not limited to, I-Sce I, I-Chu I, I-Dmo I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, and PI-Tsp I; I-Sce I, I-Chu I, I-Dmo I, I-Cre I, I-Csm I, PI-Sce I, PI-Pfu I, PI-Tli I, PI-Mtu I, and I-Ceu I; I-Dmo I, I-Cre I, PI-See I, and PI-Pfu I Homing endonucleases generally cleave their DNA substrates as dimers, and do not have distinct binding and cleavage domains.

Zinc Finger Nucleases

Zinc finger nucleases (ZFNs) are enzymes having a DNA cleavage domain and a DNA binding zinc finger domain. ZFNs may be made by fusing the nonspecific DNA cleavage domain of an endonuclease with site-specific DNA binding zinc finger domains. Such nucleases are powerful tools for gene editing and can be assembled to induce double strand breaks (DSBs) site-specifically into genomic DNA. ZFNs allow specific gene disruption as during DNA repair, the targeted genes can be disrupted via mutagenic non-homologous end joint (NHEJ) or modified via homologous recombination (HR).

Zinc finger proteins can be designed and predicted according to the procedures in WO 98/54311, U.S. Pat. Nos. 9,187,758, 9,206,404 and 8,771,985 can be used in the present methods. WO 98/54311 discloses technology which allows the design of zinc finger protein domains that bind specific nucleotide sequences that are unique to a target gene. It has been calculated that a sequence comprising 18 nucleotides is sufficient to specify a unique location in the genome of higher organisms. Typically, therefore, the zinc finger protein domains are hexadactyl, i.e., contain 6 zinc fingers, each with its specifically designed alpha helix for interaction with a particular triplet. However, in some instances, a shorter or longer nucleotide target sequence may be desirable. Thus, the zinc finger domains in the proteins may contain at least 3 fingers, or from 2-12 fingers, or 3-8 fingers, or 3-4 fingers, or 5-7 fingers, or even 6 fingers. In one aspect, the ZFP contains 3 zinc fingers; in another aspect, the ZFP contains 4 zinc fingers. Additional description on ZFNs and their design for genome editing may be found in US 20120329067A1, incorporated herein by reference.

Transcription Activator Like Effector Nucleases (TALENs)

Transcription Activator-Like Effector Nucleases (TAL-ENs) are artificial restriction enzymes generated by fusing the TAL effector DNA binding domain to a DNA cleavage domain. These reagents enable efficient, programmable, and specific DNA cleavage and represent powerful tools for genome editing in situ. Transcription activator-like effectors (TALEs) can be quickly engineered to bind practically any DNA sequence. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA. See U.S. Ser. No. 12/965,590; U.S. Ser. No. 13/426,991 (U.S. Pat. No. 8,450,471); U.S. Ser. No. 13/427,040 (U.S. Pat. No. 8,440,431); U.S. Ser. No. 13/427,137 (U.S. Pat. No. 8,440,432); and U.S. Ser. No. 13/738,381, and U.S. Pat. No. 9,393,257, all of which are incorporated by reference herein in their entireties.

TAL effectors are proteins secreted by *Xanthomonas* bacteria. The DNA binding domain contains a highly conserved 33-34 amino acid sequence with hypervariable 12th and 13th amino acids. These two locations are highly variable (repeat variable di-residue (RVD)) and show a strong correlation with specific nucleotide recognition. This simple relationship between amino acid sequence and DNA recognition has allowed for the engineering of specific DNA binding domains by selecting a combination of repeat segments containing the appropriate RVDs.

The non-specific DNA cleavage domain from the end of the Fok1 endonuclease can be used to construct hybrid nucleases that are active in a yeast assay. These reagents are also active in plant cells and in animal cells. Initial TALEN studies used the wild-type Fok1 cleavage domain, but some subsequent TALEN studies also used Fok1 cleavage domain variants with mutations designed to improve cleavage specificity and cleavage activity. The Fok1 domain functions as a dimer, requiring two constructs with unique DNA binding domains for sites in the target genome with proper orientation and spacing. Both the number of amino acid residues between the TALEN DNA binding domain and the Fok1 cleavage domain and the number of bases between the two individual TALEN binding sites are parameters for achieving high levels of activity. The number of amino acid residues between the TALEN DNA binding domain and the Fok1 cleavage domain may be modified by introduction of a spacer (distinct from the spacer sequence) between the plurality of TAL effector repeat sequences and the Fok1 endonuclease domain. The spacer sequence may be 12 to 30 nucleotides.

The relationship between amino acid sequence and DNA recognition of the TALEN binding domain allows for designable proteins. In this case artificial gene synthesis is problematic because of improper annealing of the repetitive sequence found in the TALE binding domain. One solution to this is to use a publicly available software program (DNAWorks) to calculate oligonucleotides suitable for assembly in a two-step PCR; oligonucleotide assembly followed by whole gene amplification. A number of modular assembly schemes for generating engineered TALE constructs have also been reported. Both methods offer a systematic approach to engineering DNA binding domains that is conceptually similar to the modular assembly method for generating zinc finger DNA recognition domains.

Once the TALEN genes have been assembled they are inserted into plasmids; the plasmids are then used to transfect the target cell where the gene products are expressed and enter the nucleus to access the genome. TALENs can be used to edit genomes by inducing double-strand breaks (DSB), which cells respond to with repair mechanisms. In this manner, they can be used to correct mutations in the genome which, for example, cause disease.

In certain embodiments, the TALEN is a MegTALEN or MegaTAL. MegaTALs are fusion proteins that combine homing endonucleases with modular DNA binding domains of TALENs, resulting in improved DNA sequence targeting and increased gene editing efficiencies. N-terminal fusions of TAL anchors can be employed to increase the specificity and activity of a gene-targeted endonuclease, including one or more homing endonucleases such as one or more of the I-HjeMI, I-CpaMI, and I-OnuI homing endonucleases. MegaTALs can be constructed using the Golden Gate assembly strategy described by Cermak et al, Nucl. Acids Res. 39:e82-e82 (2011), using, e.g., an RVD plasmid library and destination vector. MegaTALs can be designed and predicted according to the procedures in WO 2013/126794 and WO 2014/191525 can be used in the present methods.

RNA-Guide Nucleases

RNA-guided nucleases according to the present disclosure include, without limitation, naturally-occurring Class II CRISPR nucleases such as Cas9 (Type II) or Cas12a/Cpf1 (Type V), as well as other nucleases derived or obtained therefrom. Exemplary Cas9 nucleases that may be used in the present invention include, but are not limited to, *S. pyogenes* Cas9 (SpCas9), *S. aureus* Cas9 (SaCas9), *N. meningitidis* Cas9 (NmCas9), *C. jejuni* Cas9 (CjCas9), and *Geobacillus* Cas9 (GeoCas9). In functional terms, RNA-guided nucleases are defined as those nucleases that: (a) interact with (e.g., complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., *S. pyogenes* vs. *S. aureus*) or variation (e.g., full-length vs. truncated or split; naturally-occurring PAM specificity vs. engineered PAM specificity).

Various RNA-guided nucleases may require different sequential relationships between PAMs and protospacers. In general, Cas9s recognize PAM sequences that are 5' of the protospacer as visualized relative to the top or complementary strand. In addition to recognizing specific sequential orientations of PAMs and protospacers, RNA-guided nucleases generally recognize specific PAM sequences. *S. aureus* Cas9, for example, recognizes a PAM sequence of NNGRRT, wherein the N sequences are immediately 3' of the region recognized by the gRNA targeting domain. *S. pyogenes* Cas9 recognizes NGG PAM sequences. It should also be noted that engineered RNA-guided nucleases can have PAM specificities that differ from the PAM specificities of similar nucleases (such as the naturally occurring variant from which an RNA-guided nuclease is derived, or the naturally occurring variant having the greatest amino acid sequence homology to an engineered RNA-guided nuclease). Modified Cas9s that recognize alternate PAM sequences are described below.

RNA-guided nucleases are also characterized by their DNA cleavage activity: naturally-occurring RNA-guided nucleases typically form DSBs in target nucleic acids, but engineered variants have been produced that generate only SSBs (discussed above; see also Ran et al. Nature Protocols, 8(11): 2281-2308 (2013), incorporated by reference herein), or that do not cut at all.

RNA-guided nucleases include nickase variants, such as a Cas9 nickase. Various RNA-guided nickases or CRISPR nickases are known in the art, such as an *S. pyogenes* Cas9 with a D10A mutation. A dual-nickase approach may be employed, wherein two nicks on opposite strands of a sequence of interest that are offset by one or more nucleotides are introduced. When the two nicks are introduced, a double stranded break is created.

Accordingly, one of skill in the art would be able to select the appropriate nuclease for the present invention.

Guide RNA

As used herein, the term "guide RNA" or "gRNA" refer to any nucleic acid that promotes the specific association (or "targeting") of an RNA-guided nuclease such as a Cas9 to a target sequence (e.g., a genomic or episomal sequence) in a cell.

As used herein, a "modular" or "dual RNA" guide comprises more than one, and typically two, separate RNA molecules, such as a CRISPR RNA (crRNA) and a trans-activating crRNA (tracrRNA), which are usually associated with one another, for example by duplexing. gRNAs and their component parts are described throughout the literature (see, e.g., Briner et al. Mol. Cell, 56(2), 333-339 (2014), which is incorporated by reference).

As used herein, a "unimolecular gRNA," "chimeric gRNA," or "single guide RNA (sgRNA)" comprises a single RNA molecule. The sgRNA may be a crRNA and tracrRNA linked together. For example, the 3' end of the crRNA may be linked to the 5' end of the tracrRNA. A crRNA and a tracrRNA may be joined into a single unimolecular or chimeric gRNA, for example, by means of a four nucleotide (e.g., GAAA) "tetraloop" or "linker" sequence bridging complementary regions of the crRNA (at its 3' end) and the tracrRNA (at its 5' end).

As used herein, a "repeat" sequence or region is a nucleotide sequence at or near the 3' end of the crRNA which is complementary to an anti-repeat sequence of a tracrRNA.

As used herein, an "anti-repeat" sequence or region is a nucleotide sequence at or near the 5' end of the tracrRNA which is complementary to the repeat sequence of a crRNA.

Additional details regarding guide RNA structure and function, including the gRNA/Cas9 complex for genome editing may be found in, at least, Mali et al. Science, 339(6121), 823-826 (2013); Jiang et al. Nat. Biotechnol. 31(3). 233-239 (2013); and Jinek et al. Science, 337(6096), 816-821 (2012); which are incorporated by reference herein.

As used herein, a "guide sequence" or "targeting sequence" refers to the nucleotide sequence of a gRNA, whether unimolecular or modular, that is fully or partially complementary to a target domain or target polynucleotide within a DNA sequence in the genome of a cell where editing is desired. Guide sequences are typically 10-30 nucleotides in length, e.g., 16-24 nucleotides in length (for example, 16, 17, 18, 19, 20, 21, 22, 23 or 24 nucleotides in length), and are at or near the 5' terminus of a Cas9 gRNA.

As used herein, a "target domain" or target polynucleotide sequence" is the DNA sequence in a genome of a cell that is complementary to the guide sequence of the gRNA.

In addition to the targeting domains, gRNAs typically include a plurality of domains that influence the formation or activity of gRNA/Cas9 complexes. For example, as mentioned above, the duplexed structure formed by first and secondary complementarity domains of a gRNA (also referred to as a repeat: anti-repeat duplex) interacts with the recognition (REC) lobe of Cas9 and may mediate the formation of Cas9/gRNA complexes (Nishimasu et al. Cell 156: 935-949 (2014); Nishimasu et al. Cell 162(2), 1113-1126 (2015), both incorporated by reference herein). It should be noted that the first and/or second complementarity domains can contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for example through the use of A-G swaps as described in Briner 2014, or A-U swaps. These and other similar modifications to the first and second complementarity domains are within the scope of the present disclosure.

Along with the first and second complementarity domains, Cas9 gRNAs typically include two or more additional duplexed regions that are necessary for nuclease activity in vivo but not necessarily in vitro (Nishimasu 2015, supra). A first stem-loop near the 3' portion of the second complementarity domain is referred to variously as the "proximal domain," "stem loop 1" (Nishimasu 2014, supra; Nishimasu 2015, supra) and the "nexus" (Briner 2014, supra). One or more additional stem loop structures are generally present near the 3' end of the gRNA, with the number varying by species: *S. pyogenes* gRNAs typically include two 3' stem loops (for a total of four stem loop structures including the repeat: anti-repeat duplex), while *S. aureus* and other species have only one (for a total of three). A description of conserved stem loop structures (and gRNA structures more generally) organized by species is provided in Briner 2014, which is incorporated herein by reference. Additional details regarding guide RNAs generally may be found in WO2018026976A1, which is incorporated herein by reference.

The RNA-guided nucleases may be combined with guide RNAs to form a genome-editing system. The RNA-guided nucleases may be combined with the guide RNAs to form a ribonucleoprotein (RNP) complex that may be delivered to a cell where genome-editing is desired. The RNA-guided nucleases and guide RNAs may be expressed in a cell where genome-editing is desired. For example, the RNA-guided nucleases and guide RNAs may be expressed from one or more polynucleotides such as a vector. The vector may be a viral vector, including, be not limited to, an adeno-associated virus (AAV) vector or a lentivirus (LV) vector. The RNA-guided nuclease may alternatively be expressed from a synthetic mRNA.

Viral Delivery

The nucleic acid donors of the disclosure may be packaged in viral vector for delivery to a cell. Packaging of the nucleic acid donors may be achieved by annealing a ssRNA terminal adaptor to the viral genome for internal packaging inside the viral capsid. In a certain additional or alternative embodiments, the viral genome may encode for the components of the gene editing complex (e.g., RNA-guided nuclease and/or a guide RNA).

In some embodiments, the viral vector is an isolated recombinant adeno-associated virus (rAAV). As used herein with respect to AAVs, the term "isolated" refers to an AAV that has been artificially produced or obtained. Isolated AAVs may be produced using recombinant methods. Such AAVs are referred to herein as "recombinant AAVs." In exemplary embodiments, recombinant AAVs (rAAVs) have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected. Methods for obtaining recombinant AAVs having a desired capsid protein are well known in the art. (See, for example, US 2003/0138772, the contents of which are incorporated herein by reference in their entirety). Typically, the methods involve culturing a host cell which contains a nucleic acid sequence encoding an AAV capsid protein; a functional rep gene; a recombinant AAV vector composed of AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner. In some embodiments, a terminally grafted nuclease (e.g., at least one component of a gene editing complex) is present on all three capsid proteins (e.g., VP1, VP2, VP3) of a rAAV. In some embodiments, the terminally grafted nuclease is present on two of the capsid proteins (e.g., VP2 and VP3) of a rAAV. In some embodiments, the terminally grafted nuclease is present on a single capsid protein of a rAAV. In some embodiments, the terminally grafted nuclease is present on the VP2 capsid protein of the rAAV.

In some aspects, the instant disclosure relates to the location within an AAV capsid protein where a component of the invention (e.g., the nucleic acid donor template and/or at least one component of a gene editing complex) is grafted. In some embodiments, the component is N-terminally grafted to the capsid protein. In some embodiments, the component is C-terminally grafted to a capsid protein. In some embodiments, the component resides within the viral particle, and the viral particle does not contain a genome, e.g., a nucleic acid harboring a transgene.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art.

Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art. The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein.

In some embodiments, recombinant AAVs may be produced using the triple transfection method (described in detail in U.S. Pat. No. 6,001,650). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. In exemplary embodiments, the AAV helper function vector supports efficient AAV vector production without generating any detectable wild-type AAV virions (e.g., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both of which are incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

The foregoing methods for packaging recombinant vectors in desired AAV capsids to produce the rAAVs of the disclosure are not meant to be limiting and other suitable methods will be apparent to the skilled artisan.

Synthesis of Modified Nucleic Acid Donor Templates

The nucleic acid donors of the disclosure may be synthesized using standard molecular biology techniques known in the art. Double-stranded DNA donors may be synthesized by PCR. The donor sequence with homolog arms may be present in a vector. Oligonucleotide primers, synthesized to contain the terminal adaptors, are then used in a PCR reaction to generate the modified dsDNA donors. As an example, but in no way limiting, the oligonucleotide primers may be PEGylated, have a ssRNA at the 5' end, or both.

Single strand DNA donors may be synthesized through reverse transcription. An RNA template may be used in combination with a reverse transcription oligonucleotide primer, synthesized to contain the terminal adaptors.

Single stranded donor oligonucleotides (ssODN), which may be shorter in length than a long ssDNA donor, may be synthesized directly to contain the terminal adaptors.

As an alternative mechanism to PCR or reverse transcription, modified nucleic acid donors of the disclosure may be synthesized by ligating the terminal adaptors to the unmodified nucleic acid donor. As an example, but in no way limiting, a vector containing the nucleic acid donor and homology arms may be cut by one or more restriction enzymes to linearize the vector. The terminal adaptors may then be ligated to the ends of the linearized vector.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1—Generation of Donor Nucleic Acid Templates

The methods recited herein were employed to generate the donor DNA templates used in the below recited Examples and Figures.

Synthesis of PNA-NLS Peptide

PNA oligomers were synthesized at 2 µmol scale on Fmoc-PAL-PEG-PS solid support (Applied Biosystems) using an Expedite 8909 synthesizer. Fmoc/Bhoc-protected PNA monomers (Link Technologies) were dissolved to 0.2 M in anhydrous N-methylpyrrolidinone. amino acid monomers (Sigma Aldrich) and aminoethoxyethoxyacetate (AEEA) linker (Link Technologies) were dissolved to 0.2 M in anhydrous dimethylformamide. Coupling time was 8.5 minutes using hexafluorophosphate azabenzotriazole tetramethyl uronium (HATU) (Alfa Aesar) as activator; double-coupling was performed on all PNA monomers and amino acids. PNAs were cleaved and deprotected by treating the resin with 400 µL of 19:1 TFA:m-Cresol for 90 minutes at room temperature. The resin was then removed with a PTFE centrifugal filter and PNAs were precipitated from cold diethyl ether and resuspended in deionized water. PNAs were purified by HPLC on a Waters XSelect CSH C18 5 µm column at 60° C., using gradients of acetonitrile in water containing 0.1% TFA and were characterized on an Agilent 6530 Q-TOF LC/MS system with electrospray ionization.

Synthesis of PEGylated Oligonucleotides

PEG-modified oligonucleotides were synthesized using standard phosphoramidite methods on an ABI 394 synthesizer. Phosphoramidites were purchased from ChemGenes. Coupling times for 2'OMe-RNA and spacer phosphoramidites were extended to 5 minutes. Oligonucleotides were deprotected in concentrated aqueous ammonia at 55° C. for 16 hours. Oligonucleotides were desalted using either Nap-10 (Sephadex) columns or Amicon ultrafiltration. All the PEG-modified oligonucleotides were characterized on an Agilent 6530 Q-TOF LC/MS system with electrospray ionization.

PCR dsDNA Donor Generation

Donor template sequences with the homology arms and the desired insert for knock-in (e.g., GFP), were generated by PCR. PCR products were cloned into ZeroBlunt TOPO vector (Invitrogen, #450245) and plasmids were purified using Macherey-Nagel midi-prep kits (cat #740412.50). Using the purified plasmids as templates and PEGylated oligonucleotides as primers, donor sequences were PCR amplified with iProof (Bio-Rad, 1725302, *C. elegans*) or Phusion polymerase (NEB, #M0530S, mammalian). The resulting PEGylated PCR products were excised from 0.8-1% TAE agarose gel and purified using spin-columns (Omega, #D2501-02, *C. elegans* and Qiagen, #28104, mammalian (not gel excised). PCR conditions were optimized for each primer set with a gradient for the annealing temperature [1) 98° C. for 1:00 minute, 2) 98° C. for 15 seconds, 3) 50° C. to 64° C. for 30 seconds (choose optimal), 4) 72° C. for 1:00 minute (34 cycles), 5) 72° C. for 5:00 minutes, 6) 4° C. forever].

Single-Stranded DNA Donor Generation

Single-stranded DNA donors were prepared using the protocol described previously (Li et al. "Design and specificity of long ssDNA donors for CRISPR-based knock-in" bioRxiv, (2017)). Briefly, the donor template containing the T7 promoter was amplified using standard PCR and purified using SPRI magnetic beads (Core Genomics). T7 in vitro transcription was performed using the HiScribe T7 High Yield RNA Synthesis kit (NEB) and the RNA was purified using the SPRI magnetic field. Finally, the ssDNA donor was synthesized by TGIRT™-III (InGex) based reverse transcription using the synthesized RNA as a template. The donor was again purified using SPRI beads.

Example 2—HDR Efficiency in *C. elegans*

The modified DNA donor templates were tested in *C. elegans* to determine their efficacy in homology-directed repair (HDR) relative to unmodified DNA donor templates. The following methods were employed in the Examples and Figures recited below.

*C. elegans* Microinjection and HDR Screening

Microinjections were performed using Cas9 ribonucleoproteins Cas9-RNPs) at final concentrations of: 0.25 µg/µl of SpCas9 protein (IDT, #1074181), 0.04 µg/µl of crRNA (against the target sequence), 0.016 µg/µl of crRNA (dpy-10) (IDT, Alt-R® CRISPR-Cas9 crRNA) and 0.1 µg/µl of tracrRNA (IDT, #1072533) along with a series of modified or unmodified DNA donors (10 µg/ul or 100 µg/µl). Donors conjugated to single stranded RNA-tetraethylene glycol (ssRNA-TEG) adaptors were mixed with either peptide nucleic acid-nuclear localization signal (PNA-NLS) ligands or with water. The mixture was heated to 95° C. and cooled to 4° C. using the thermal cycler (95° C.—2:00 min; 85° C.—10 sec, 75° C.—10 sec, 65° C.—10 sec, 55° C.—1:00 min, 45° C.—30 sec, 35° C.—10 sec, 25° C.—10 sec, 4° C.—forever). As a control, microinjections were performed with the DNA donor that lacks chemical modifications. After the microinjections, injected animals (P0) were singly picked onto Normal Growth Media (NGM) plates and cultured at 20°-22° C. for about 3.5 days. F1 animals exhibiting evidence of CRISPR induced lesions at a marker locus (dpy-10) (Arribere et al., Genetics. 198(3): 837-846 (2014)) were screened under a fluorescent dissection microscope for the presence or absence of GFP expression in the gonad. The percentage of GFP positive animals were plotted among the total number of dumpys/rollers produced by each P0 animal. Only those POs that produced at least 15 F1 dumpy and roller animals were considered.

*C. elegans* GFP Tagging Strategy

In *C. elegans*, the aim was to insert the entire coding sequence of green fluorescent protein (GFP) immediately after the ATG start codon of csr-1, prg-1 and glh-1 genes. For this, a two-step CRISPR protocol was developed to fuse any gene to a large DNA sequence (such as GFP or mCherry, approximately 900 bp). By modifying the previously published CRISPR protocol (Paix et al. Genetics. 201: 47-54 (2015)) high frequency of HDR efficiencies for short inserts such as 3×FLAG was achieved (data not shown). Cas9-RNP complexes and single stranded donor oligonucleotides (ssODN) were employed to knock-in the FLAG (×3):: Glycine(×3) linker::TEV tag using 35 bp homology arms for HDR. Strains with homozygous FLAG-tagged alleles were used to knock-in the GFP sequence between FLAG and the glycine-linker. A crRNA (CTATAAAGACGATGACGATA NGG (SEQ ID NO: 2)) with a PAM site in the glycine-linker and donor DNA with arms homologous to 35 bp of FLAG×3 and 30 bp of glycine-linker::TEV flanking the GFP sequence was used.

HDR Efficiency in *C. elegans*—Results

In the worm germline, high rates of HDR are readily achieved using short (under approximately 200 nucleotides) single-stranded oligodeoxynucleotide (ssODN) donor templates that permit edits of up to approximately 150 nucleotides in length (Paix et al. Genetics 201:47-54 (2015); Prior et al. G3 Bethesda 7:3693-3698 (2017)). However, HDR is less efficient by 1-2 orders of magnitude when longer, double-stranded DNA (dsDNA) templates are used as donors (unpublished results).

Availability of donor molecules at the site of repair is a critical requirement for efficient HDR. Longer repair templates are likely at a disadvantage in this regard for several reasons. First, toxicity associated with high concentrations of DNA limits the safe injectable concentration of a 1 kb dsDNA donor to roughly approximately 10-fold lower than what is commonly used for a 200 nucleotide ssODN donor (Paix, supra; Prior, supra; Mello et al. EMBO 10: 3959-3970 (1991)). Second, in post-mitotic germ-nuclei, long dsDNA donor molecules may not be able to readily diffuse from the cytoplasm into the nucleus, further reducing the effective concentration at the site of repair. It was therefore hypothesized that the order-of-magnitude disparity in relative availability of ssODN and dsDNA donor molecules inside germ nuclei could account for the differences in observed HDR rates. In an effort to increase the nuclear uptake of long dsDNA, an SV40 peptide containing the core nuclear localization signal (NLS) was chemically attached. Using mammalian cell cultures, previous studies demonstrated that the addition of an NLS can greatly enhance nuclear uptake of plasmids following transfection (Branden et al. Nature Biotechnology. 17: 784-787 (1999); Ludtke et al. J. Cell Sci. 112: 2033-2041 (1999)). An exemplary design of the disclosure relied on chemically modifying the 5' ends of the PCR primers used to generate the dsDNA donor molecules. To do this a 15-nucleotide 2'-OMe-RNA was synthesized and attached to the DNA primers with a tri/tetraethylene glycol (TEG) linker (FIG. 1). In addition, the NLS peptide linked to a peptide nucleic acid (PNA) complementary to the 2'-OMe-RNA was synthesized. Attaching the NLS to the donor is then achieved by simply annealing the NLS::PNA molecules to the 2'-OMe-RNA adapters on the ends of the PCR product.

Figure 2A:
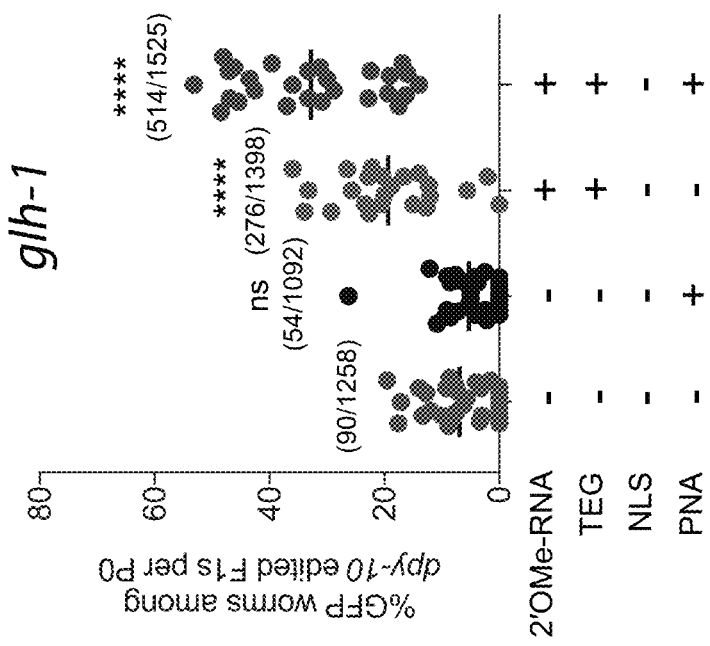
FIG. 2A-FIG. 2B depict percent GFP positive worms from the insertion of a GFP-encoding template at the *C. elegans* csr-1 locus (FIG. 2A) and glh-1 locus (FIG. 2B) by homology-directed repair. Donor templates were either unmodified or had a 2'-OMe-RNA::TEG adaptor with or without a PNA annealed to the ends.
Figure 2B:
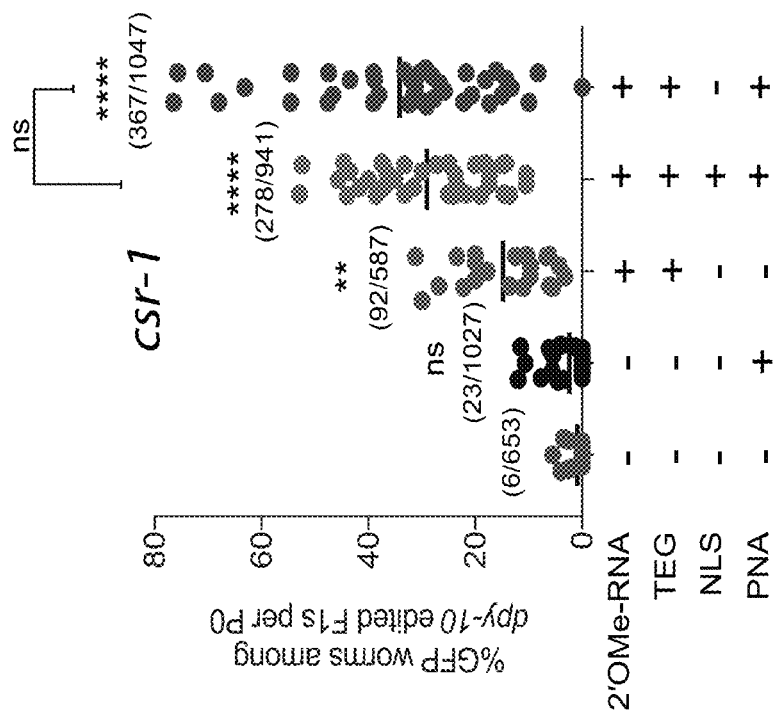
Figure 3:
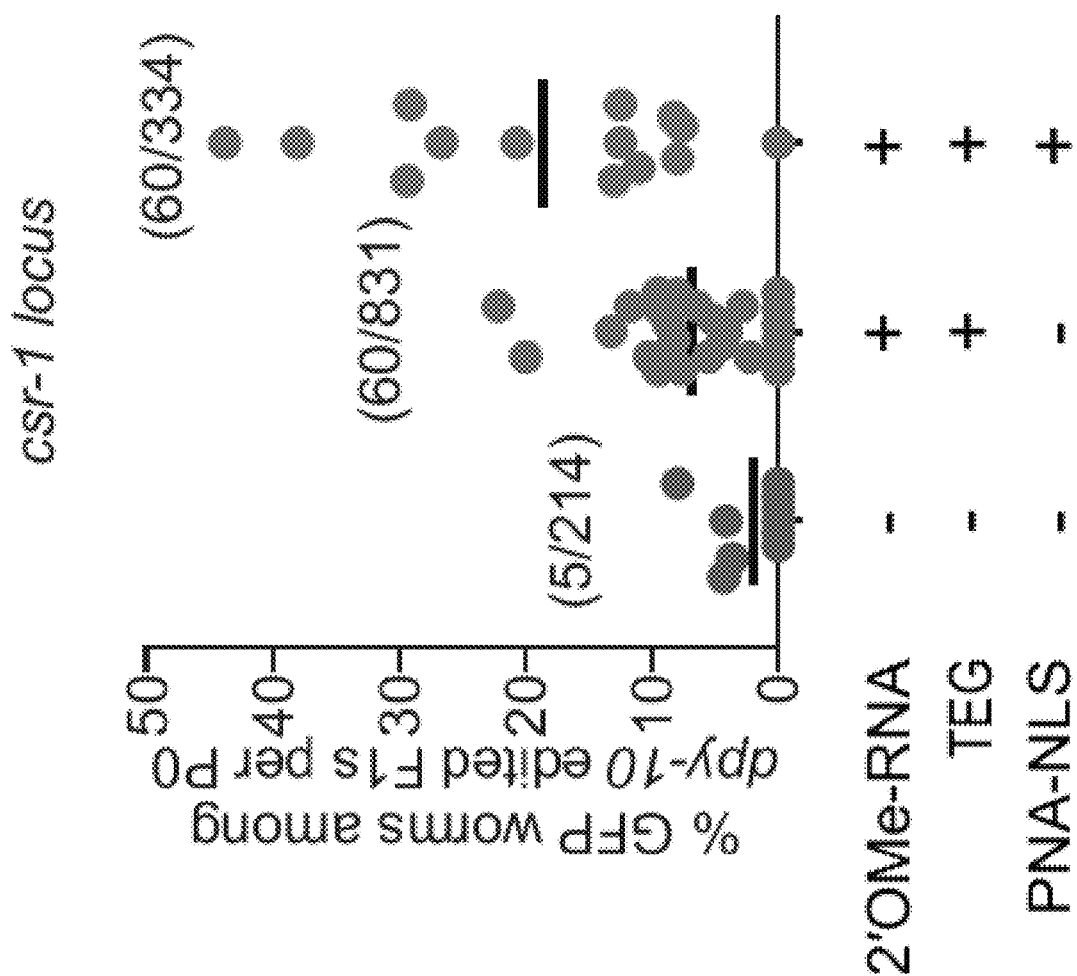
FIG. 3 depicts percent GFP positive worms from the insertion of a GFP-encoding template at the *C. elegans* csr-1 locus by homology-directed repair. 100 ng/μl of donor template was used.

The modified donors were tested by inserting green fluorescent protein (GFP) in-frame with the *C. elegans* csr-1 gene (FIG. 2A). GFP::CSR-1 was readily detectable under a fluorescence dissection microscope as a bright perinuclear signal within the germline. To measure HDR efficiency a second CRISPR RNA(crRNA) designed to generate indels in an independent locus (dpy-10) was co-injected. Lesions in this marker gene cause easily scored morphological phenotypes (dumpy and roller phenotypes). HDR efficiency was then scored as a fraction of F1 dumpy or roller animals (among progeny of injected animals) that properly express GFP::CSR-1. To increase the sensitivity of the assay, a donor DNA concentration of 10 ng/μl (approximately 35-fold less than previously recommended) (Paix et al., supra) was chosen. At these very low concentrations the insertion rate of GFP using unmodified dsDNA donor was just 0.58%. Strikingly, the same dsDNA donor modified at both 5' ends with 2'OMe-RNA::TEG annealed to PNA yielded a significant increase in HDR efficiency (FIG. 2A). Interestingly, donors prepared with 2'-OMe-RNA::TEG end-modification only, without the addition of the PNA, also substantially improved HDR efficiency to 9.86% (FIG. 2A). Increasing the donor concentration ten-fold to 100 ng/μl boosted the rate of accurate GFP insertions with unmodified dsDNA donor almost five-fold to approximately 2.34% but failed to provide an additional boost to the efficiency of the modified donors (FIG. 3). Thus, while the unmodified donors were clearly limiting for HDR at the concentration of 10 ng/μl, the end-modified donors were not. To demonstrate the generality of these findings, GFP insertions were targeted into two additional loci—prg-1 and glh-1—and comparable increases in HDR efficiencies were found at both targets (FIG. 2B).

Example 3—HDR Efficiency in Mammalian Cells

Cell Culture and Transfections

HEK293 cells were obtained from ATCC and were cultured in standard DMEM medium (Gibco, #11995) supplemented with 10% fetal bovine serum (FBS) (Sigma, #F0392). Human foreskin fibroblasts (HFF) were maintained in DMEM medium supplemented with 15% FBS. Chinese hamster ovary (CHO) cells (obtained from ATCC) were cultured in F-12K medium (Gibco 21127022) supplemented with 10% FBS. Electroporations were performed using the Neon transfection system (ThermoFisher). SpCas9 was delivered either as a plasmid or as protein. For plasmid delivery of Cas9 and sgRNA, appropriate amounts of plasmids were mixed in approximately 10 μL Neon buffer R (ThermoFisher) followed by the addition of 100,000 cells. For RNP delivery of Cas9, 20 pmoles of 3NLS-SpCas9 and 25 pmoles of crRNA:tracrRNA were mixed in 10 μL of buffer R. This mixture was incubated at room temperature of 30 minutes followed by the addition of 100,000 cells which were already resuspended in buffer R. This mixture was then electroporated using the 10 μL Neon tips. Electroporation parameters (pulse voltage, pulse width, number of pulses) were 1150 v, 20 ms, 2 pulses for HEK293T cells, 1650 v, 10 ms, 3 pulses for CHO cells and 1400 v, 30 ms, 1 pulse for HFF cells. Electroporated cells were harvested for FACS analysis 48-72 hours post electroporation unless mentioned otherwise in results.

K562 GFP Positive Stable Cell Line Generation & the GFP-to-BFP Assay

A Lentiviral vector expressing EGFP was cloned using the Addgene plasmid #31482. The EGFP sequence was cloned downstream of the SFFV promoter using Gibson assembly. For lentivirus production, the lentiviral vector was co-transfected into HEK293T cells along with the packaging plasmids (Addgene 12260 & 12259) in 6-well plates using TransIT-LT1 transfection reagent (Mirus Bio) as recommended by the manufacturer. After 24 hours, the medium was aspirated from the transfected cells and replaced with fresh 1 mL of fresh DMEM media. The next day, the supernatant containing the virus from the transfected cells was collected and filtered through 0.45 μm filter. 10 μL of the undiluted supernatant along with 2.5 μg of Polybrene was used to transduce approximately 1 million K562 cells in 6-well plates. The transduced cells were selected using 2.5 μg/mL of Puromycin containing media. Less than 20% of the transduced cells survived which were then diluted on the 96-well plates to select single clones. One of the K562 GFP+ clones was used to perform the GFP-to-BFP assays. Cas9 was nucleofected into the K562 GFP+ cells as RNP (20 pmol) with a crRNA against the GFP sequence. ssODN (66 nucleotides) with or without end modifications were provided as donor templates to convert the GFP coding sequence to BFP coding sequence. % BFP+ (HDR) and % GFP (−); BFP(−) (NHEJ) cells was quantified using flow cytometry.

Flow Cytometry

The electroporated cells were analyzed on MACSQuant VYB from Miltenyi Biotec. Cells were gated first based on forward and side scattering to select "live" cells and then for single cells. GFP positive cells were identified using the blue laser (488 nm) and 525/50 nm filter whereas for the detection of mCherry positive cells, yellow laser (561 nm) and 615/20 nm filter was used.

Traffic Light Reporter (TLR) Targeting

Figures 5A, 5B:
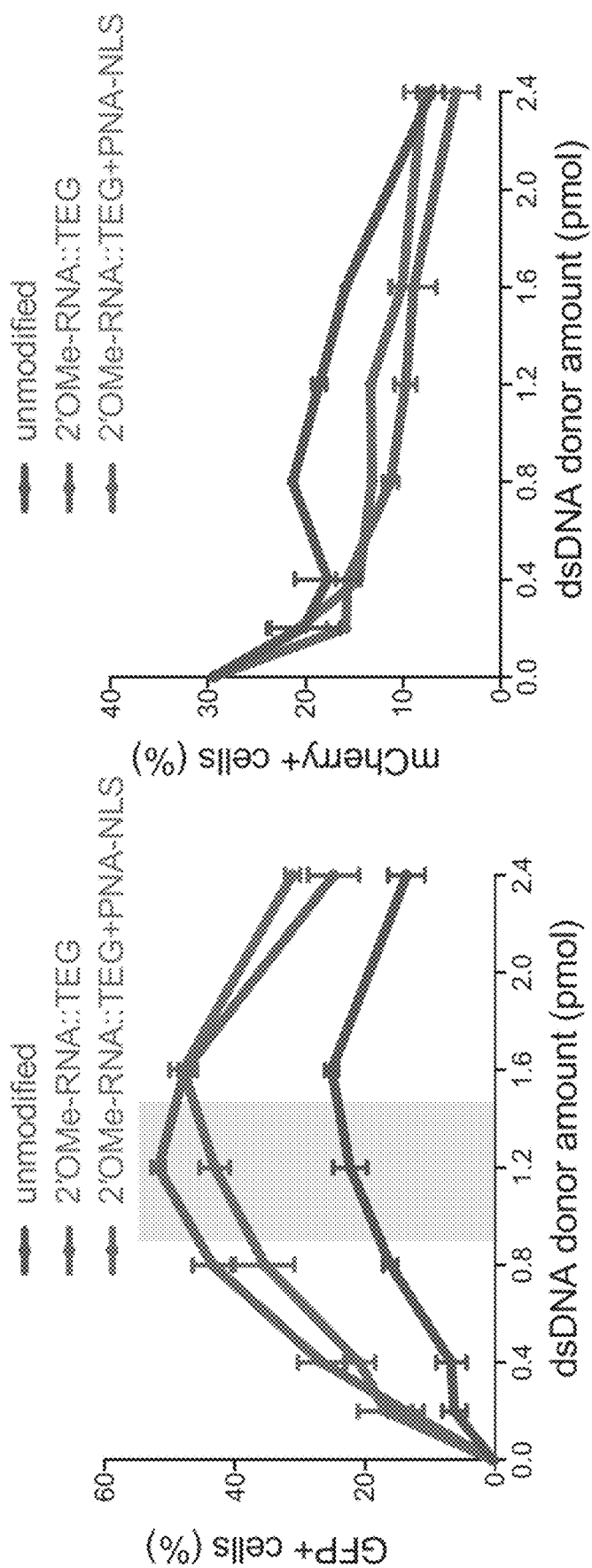
FIG. 5A-FIG. 5B depict genome editing using the TLR system in HEK293T cells. SpyCas9, a sgRNA targeting EGFP in the reporter, and a GFP-encoding donor template were delivered and percent GFP positive cells (FIG. 5A) and percent mCherry positive cells (FIG. 5B) were determined by flow cytometry.

The modified DNA donor templates of the disclosure were next tested in mammalian cell culture systems. HEK293T cells carrying a modified version of the "traffic light" reporter (TLR) were used (Certo et al. Nature Methods. 8: 671-676 (2011)). Briefly, in this system Cas9 targets a "broken" GFP followed by a frameshifted mCherry reporter. Imprecise repair via non-homologous end-joining (NHEJ) restores frame in a subset of indels, resulting in mCherry (red) fluorescence. Conversely, precisely templated repair of the same lesion results in GFP (green) fluorescence. Using flow cytometry, the percentage of cells expressing either GFP (HDR) or mCherry (NHEJ) among the total number of cells can be easily quantified. To perform the TLR assay, reporter cells were nucleofected with Cas9- and single guide RNA (sgRNA)-encoding plasmids, along with either an unmodified dsDNA donor, a 2'-OMe-RNA::TEG end-modified donor, or the end-modified donor annealed to PNA::NLS. Strikingly, across a range of donor concentrations, a consistent and significant increase in HDR efficiency with the end-modified donors was observed a (FIG. 5A). The efficiency peaked at 51.8% GFP-positive cells with 1.2 pmol of 2'-OMe-RNA::TEG modified donor, compared to a frequency of 22% obtained at this concentration with unmodified donor (FIG. 5A). This gain of GFP+ cells was accompanied by a corresponding loss of mCherry+ cells (FIG. 5B). After peaking, the fraction of GFP+ cells declined for all donor types and was not accompanied by corresponding increase in mCherry+ cells, indicating overall increase in the fraction of unedited cells, likely due to loss of edited cells due to donor toxicity. Notably, 2'-OMe-RNA::TEG donor peaked before the unmodified DNA, indicating it is significantly more potent. Indeed, the maximum 25% GFP+ cell achieved at 1.6 pmol of unmodified DNA could be achieved with less than 0.4 pmol of 2'-OMe-RNA::TEG modified donor (FIG. 5A). With reduced donor concentration, the HDR efficiency declined for all donor types while the total editing efficiency remained constant (FIG. 5A and FIG. 5B). Thus, although less dramatic than the 30-fold increase observed in worms (which appear to have a much lower basal HDR efficiency), more than two-fold increases in HDR was observed using this mammalian cell culture system. Interestingly, unlike in worms, the addition of PNA::NLS to the 2'-OMe-RNA::TEG end-modified donor provided no additional increase in HDR efficiency (FIG. 5A), perhaps because cell-cycle related nuclear envelope breakdown in these actively dividing HEK293 Ts cells obviates the need for active nuclear transport.

Figure 4A:
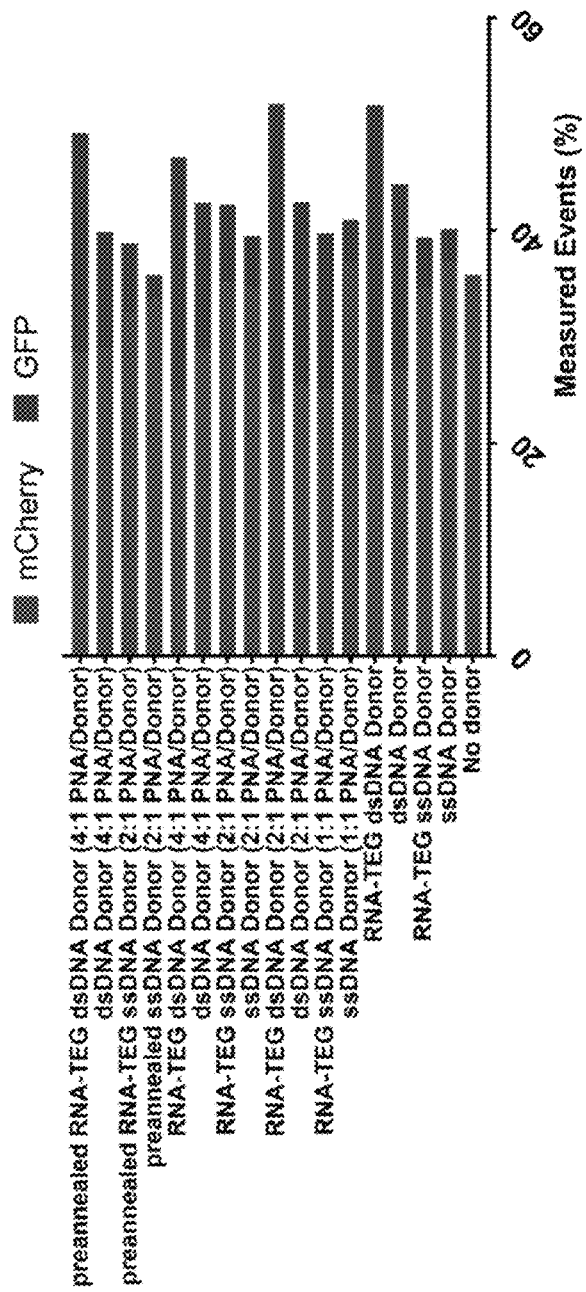
FIG. 4A-FIG. 4B depict genome editing using the traffic light reporter (TLR) system in HEK293T cells. SpyCas9 and sgRNA targeting EGFP in the reporter were delivered as RNPs (FIG. 4A) or as plasmids (FIG. 4B). A GFP-encoding donor template with various modifications was also transfected into the cells.
Figure 4B:
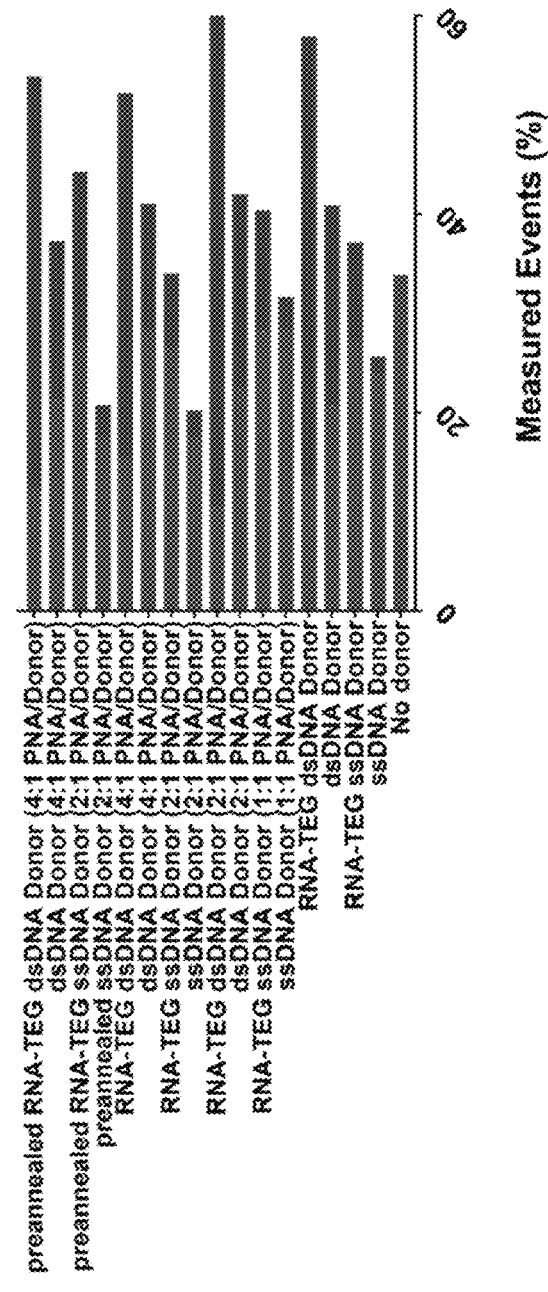

A similar experiment was performed as recited above using the TLR system in HEK293T cells. Cas9 and sgRNA targeting EGFP in the reporter were delivered as RNPs (FIG. 4A) or as plasmids (FIG. 4B). A GFP-encoding donor template with various modifications was also transfected into the cells. As described above, similar HDR enhancement was achieved whether Cas9 and the sgRNA were introduced by electroporating into the cells a Cas9/sgRNA RNP or plasmids encoding Cas9 and the sgRNA.

Figures 6A, 6B:
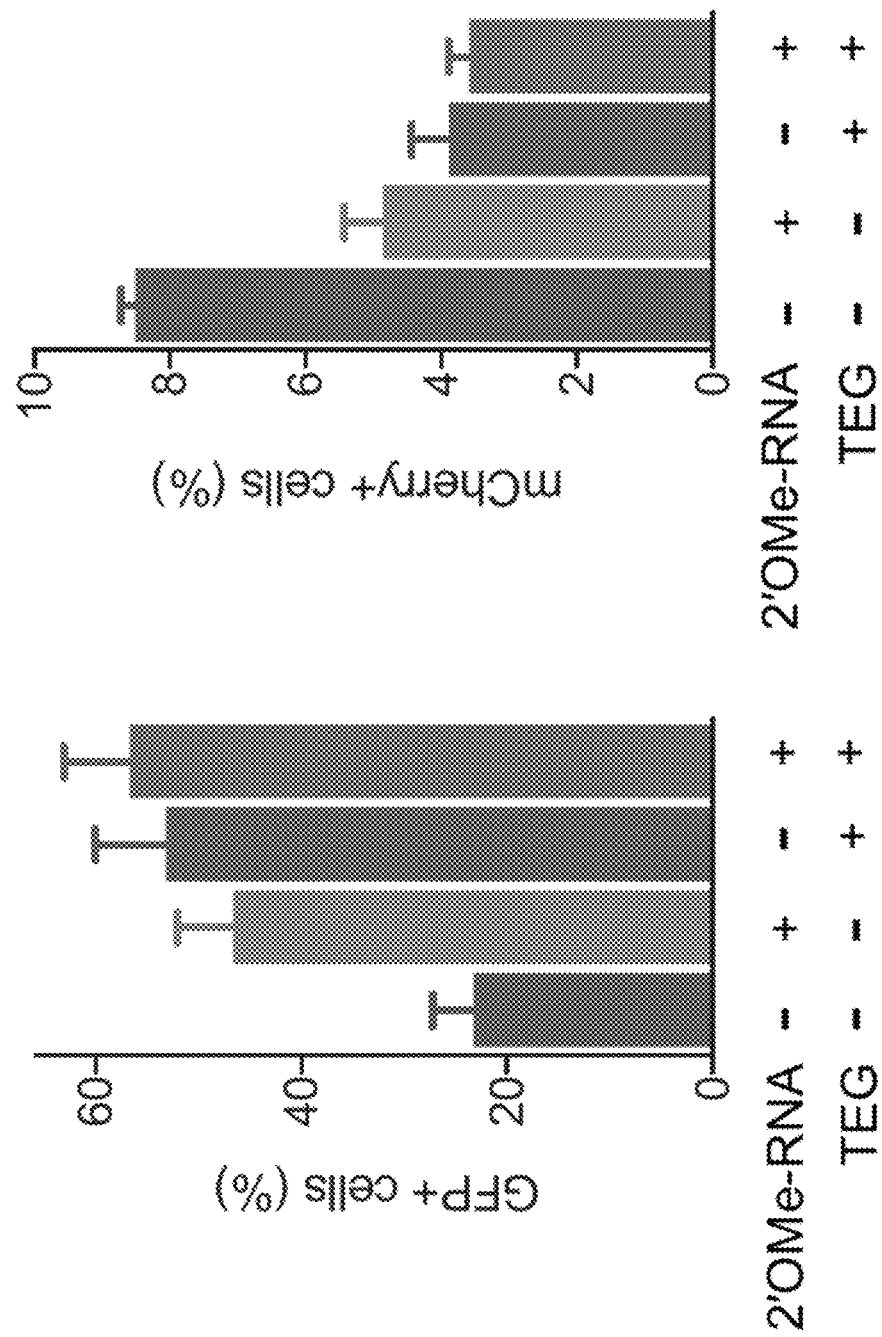
FIG. 6A-FIG. 6B depict genome editing using the TLR system in HEK293T cells. SpyCas9, a sgRNA targeting EGFP in the reporter, and a GFP-encoding donor template were delivered and percent GFP positive cells (FIG. 6A) and percent mCherry positive cells (FIG. 6B) were determined by flow cytometry. Donor templates were modified with a 2'-OMe RNA adaptor, a TEG adaptor, or a 2'-OMe-RNA::TEG adaptor.
Figures 7A, 7B:
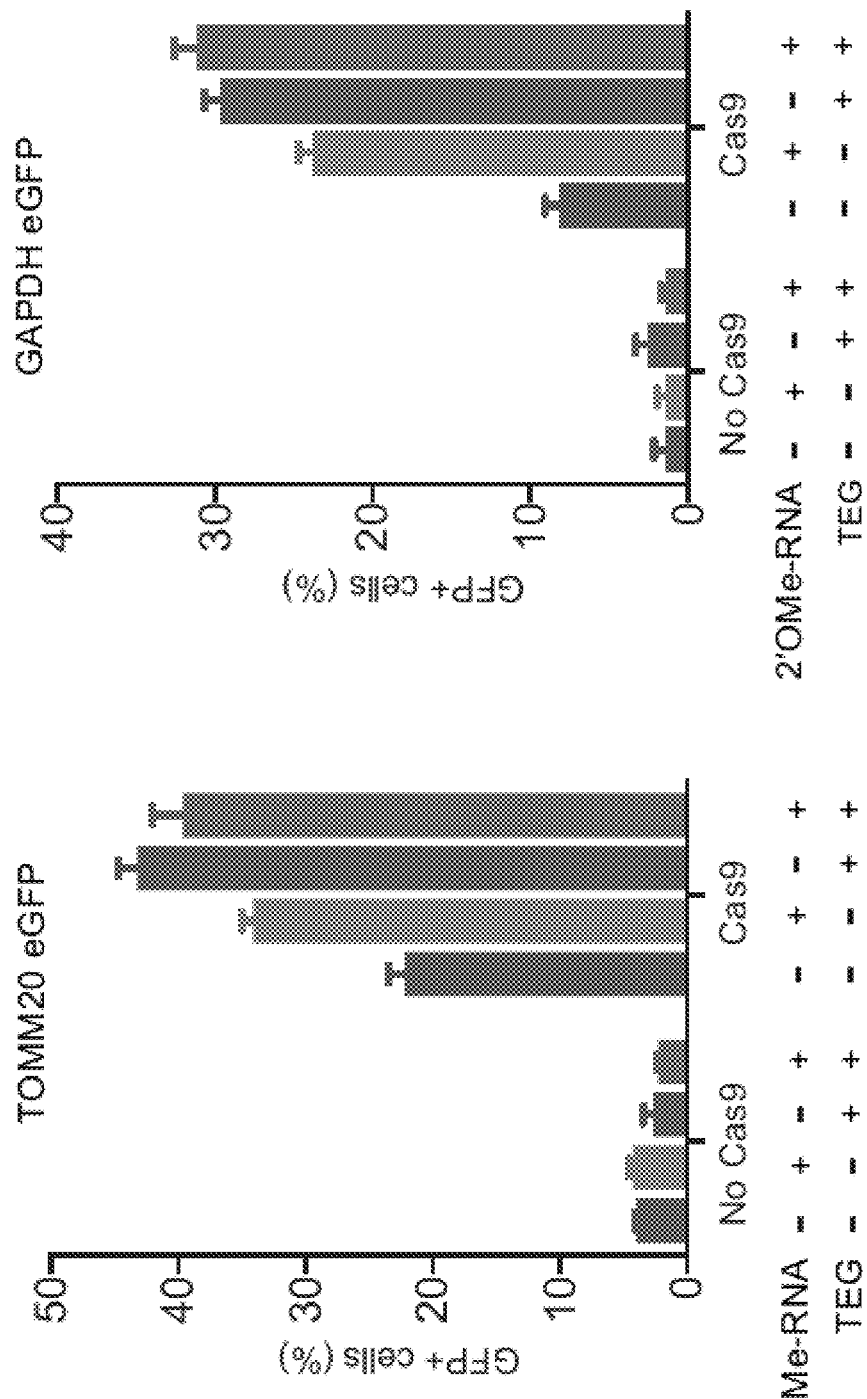
FIG. 7A-FIG. 7B depict genome editing at the TOMM20 (FIG. 7A) and GAPDH (FIG. 7B) loci in HEK293T cells. SpyCas9, a sgRNA targeting TOMM20 or GAPDH, and a GFP-encoding donor template were delivered and percent GFP positive cells were determined by flow cytometry.
Figure 10B:
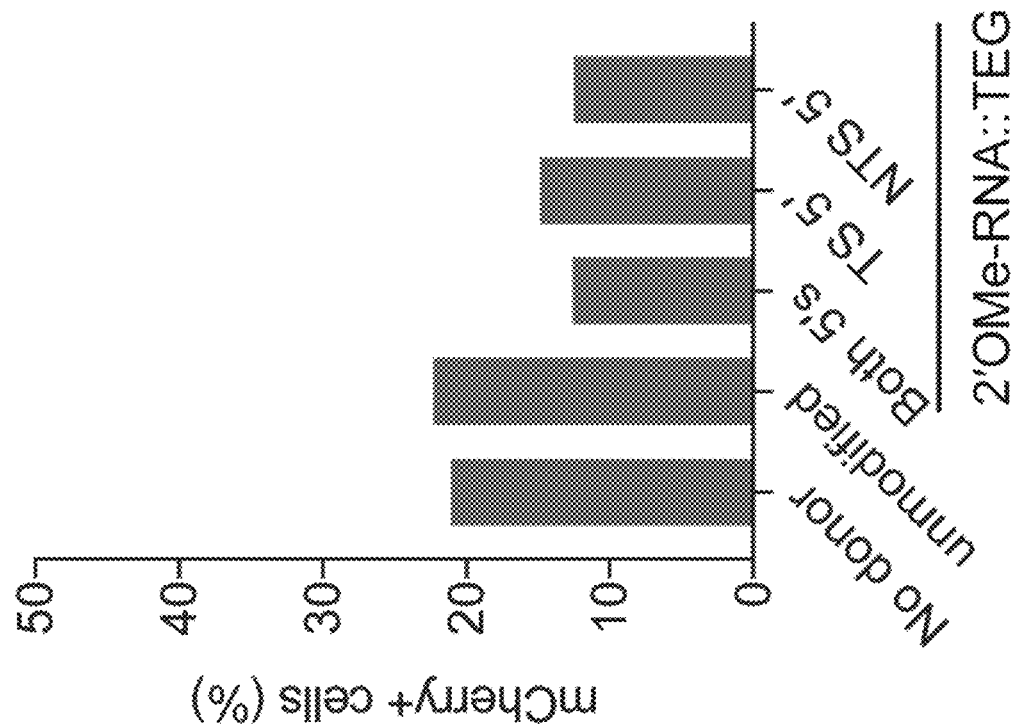
FIG. 10A-FIG. 10B depict genome editing using the TLR system in HEK293T cells. SpyCas9, a sgRNA targeting EGFP in the reporter, and a GFP-encoding donor template were delivered and percent GFP positive cells (FIG. 10A) and percent mCherry positive cells (FIG. 10B) were determined by flow cytometry. Donor templates were modified with a 2'OMe-RNA::TEG adaptor at both 5' ends of the donor template or only one of the two 5' ends of the donor template. TS—Target Strand; NTS—Non-Target Strand.
Figure 10A:
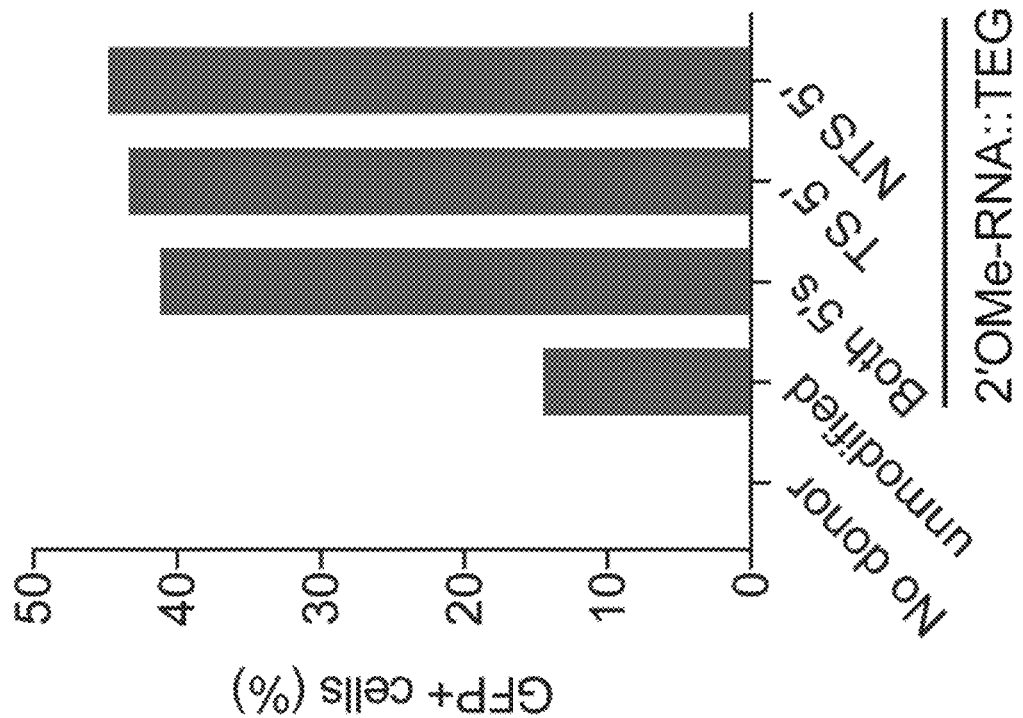
Figure 11A:
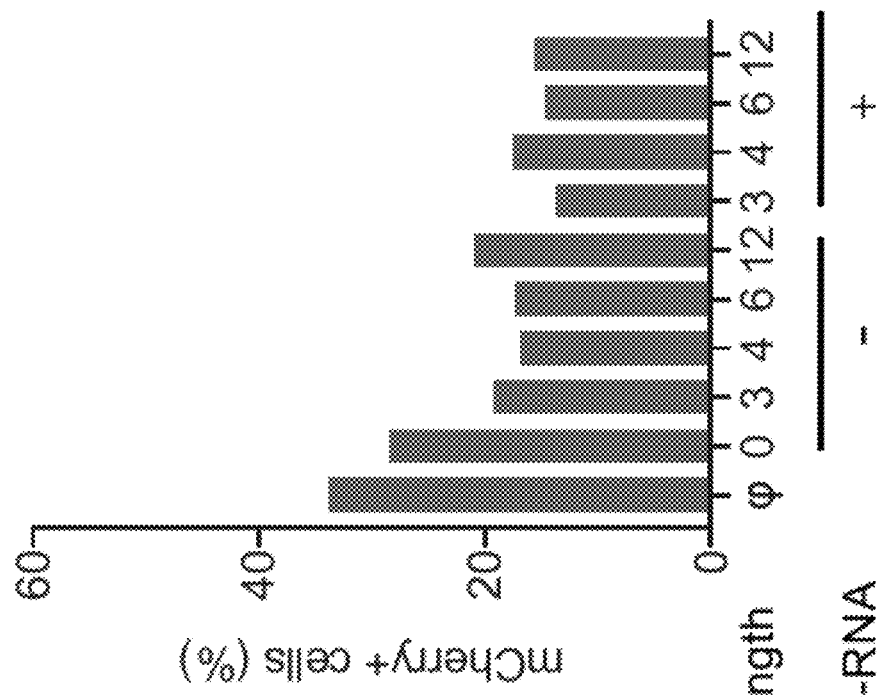
FIG. 11A-FIG. 11C depict genome editing using the TLR system in HEK293T cells. SpyCas9, a sgRNA targeting EGFP in the reporter, and a GFP-encoding donor template were delivered and percent GFP positive cells (FIG. 11A) and percent mCherry positive cells (FIG. 11B) were determined by flow cytometry. Donor templates were modified with an ethylene glycol (EG)-2'-OMe-RNA adaptor wherein a different number of EG repeats was used (0, 3, 4, 6, or 12 EG repeats).
Figure 11B:
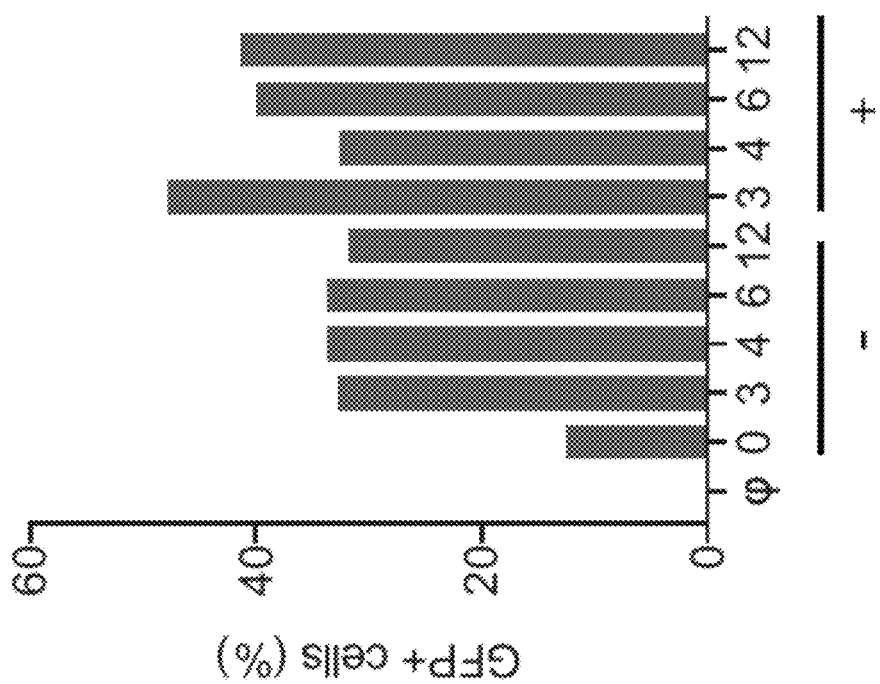
Figure 11C:
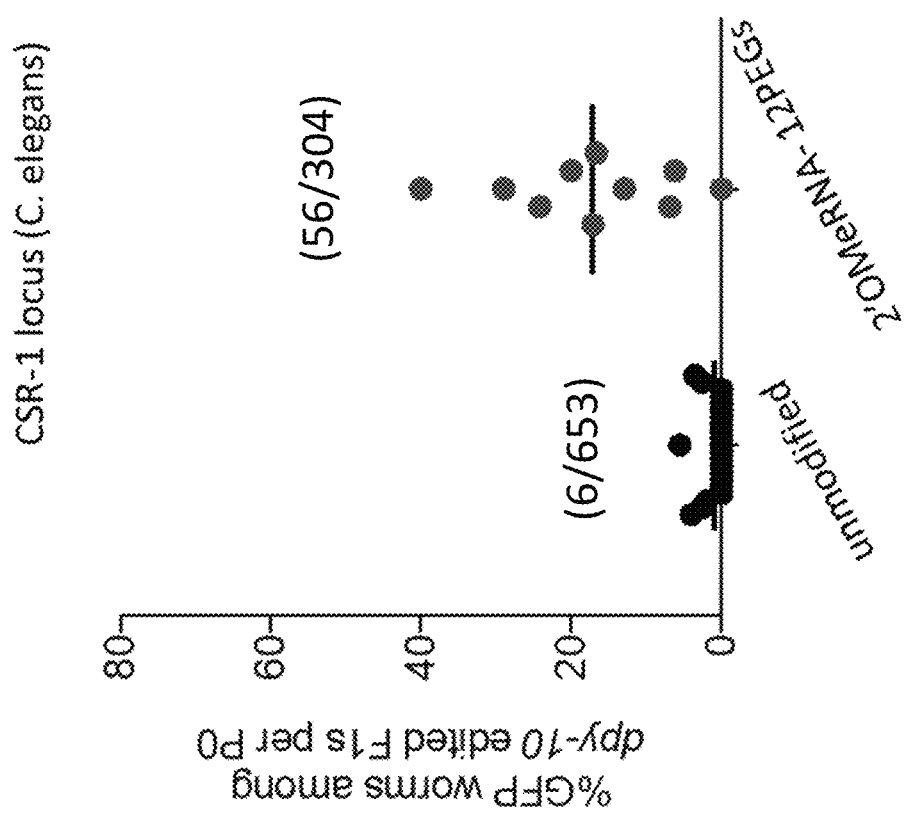

The TLR assay was next used to define the features of the 2'-OMe-RNA::TEG adapter that promote HDR (FIG. 6A and FIG. 6B). Interestingly, it was found that donors modified with either the 2'OMe-RNA alone or with TEG alone consistently boosted HDR efficiencies (FIG. 6A). Moreover, even adding the 2'-OMe-RNA::TEG adapter to only one end of the donor caused a significant boost in HDR efficiency (FIG. 10A and FIG. 10B). Finally, different lengths of PEGs (4, 6, 9 or 12 ethylene glycol repeats) also promoted HDR efficiency, although they did not improve efficiency any further. In all cases a corresponding decline in mCherry-positive cells was observed (FIG. 11A and FIG. 11B). A PEG-modified DNA donor with 12 ethylene glycol repeats was used in C. elegans as well. The results show an increase in HDR efficiency compare to an unmodified DNA donor (FIG. 11C).

Endogenous Gene Targets

Figure 8:
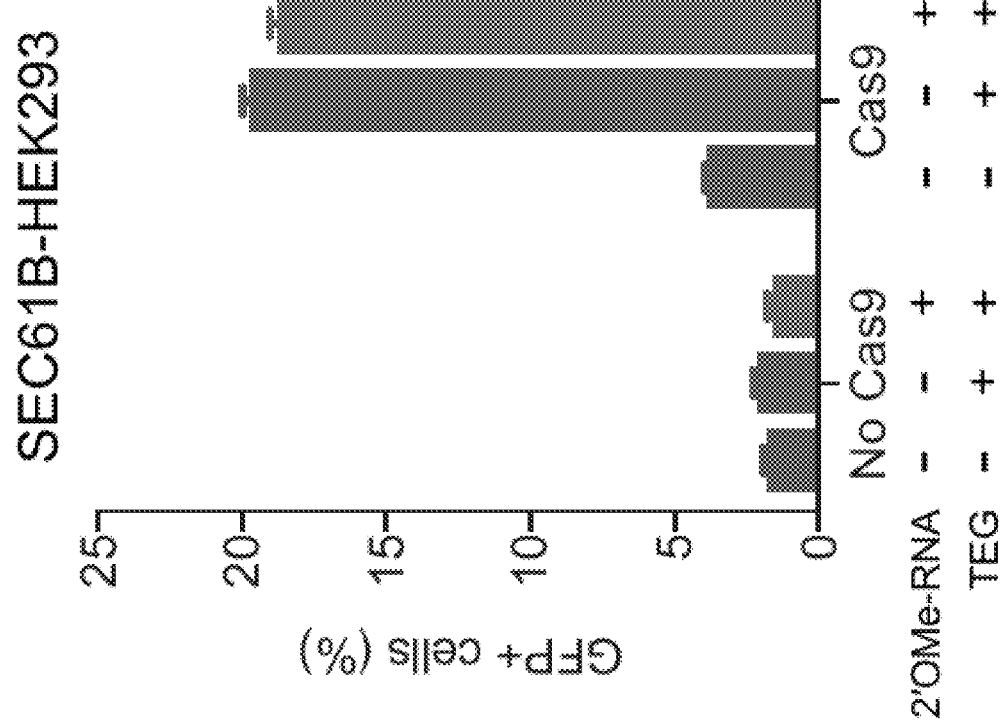
FIG. 8 depicts genome editing at the SEC61B locus in HEK293T cells. SpyCas9, a sgRNA targeting SEC61B, and a GFP-encoding donor template were delivered and percent GFP positive cells were determined by flow cytometry.

To explore the utility of end-modified donors for repair at other genomic locations, donors and guides were designed to integrate full-length eGFP at the endogenous GAPDH and TOMM20 loci in HEK293T cells. The GAPDH donor was designed to integrate IRES-eGFP in the 3-UTR of the GAPDH locus, whereas the TOMM20 donor was designed to tag the C-terminus of the mitochondrial protein TOMM20 (He et al. Nucleic Acids Research 44: e85 (2016); Roberts et al. Mol. Biol. Cell 28: 2854-2874 (2017)). By measuring the fraction of cells expressing eGFP by flow cytometry, it was found that the TEG, 2'-OMe-RNA or 2'-OMe-RNA::TEG modifications consistently increased the fraction of eGFP cells (by up to four-fold) over unmodified dsDNA donor (FIG. 8A and FIG. 8B). Again, in these loci, as in the TLR reporter, it was noted that the presence of TEG was necessary for maximal HDR and that TEG alone performed better than 2'OMe-RNA alone. Similar results were obtained at SEC61B locus in HEK-293 cells (FIG. 8). As expected, in all cases precise insertion of eGFP was Cas9 dependent.

Figures 9A, 9B:
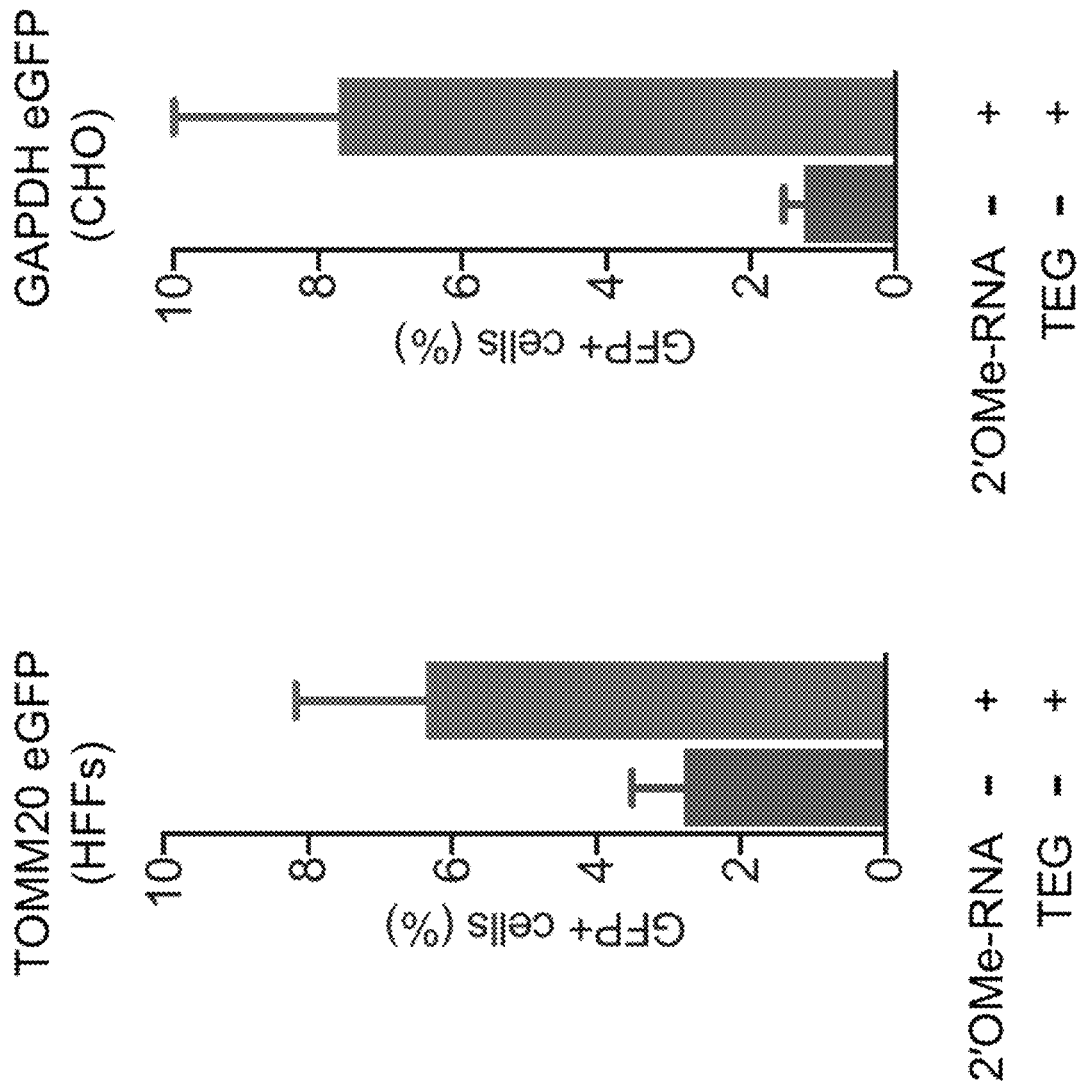
FIG. 9A-FIG. 9B depict genome editing at the TOMM20 (FIG. 9A) and GAPDH (FIG. 9B) locus in hTERT-immortalized human foreskin fibroblast (HFF) cells (FIG. 9A) or Chinese hamster ovary (CHO) cells (FIG. 9B). SpyCas9, a sgRNA targeting TOMM20 or GAPDH, and a GFP-encoding donor template were delivered and percent GFP positive cells were determined by flow cytometry.

HEK293T cells are relatively amenable to HDR. Modified donors in cell types that are typically more resistant to HDR were teste next. 2'-OMe-RNA::TEG donors and Cas9 RNPs designed to target the insertion of eGFP at the Gapdh locus in Chinese hamster ovary (CHO) cells and at the TOMM20 locus in hTERT-immortalized human foreskin fibroblasts (HFFs) were generated. Although the overall rates of HDR (as measured by the fraction of eGFP-expressing cells) were significantly lower than those observed in HEK293 Ts, a 2.3-fold and 6-fold increase in HDR in HFF and CHO cells respectively was obtained (FIG. 9A and FIG. 9B).

Single Strand DNA Templates

Figure 12B:
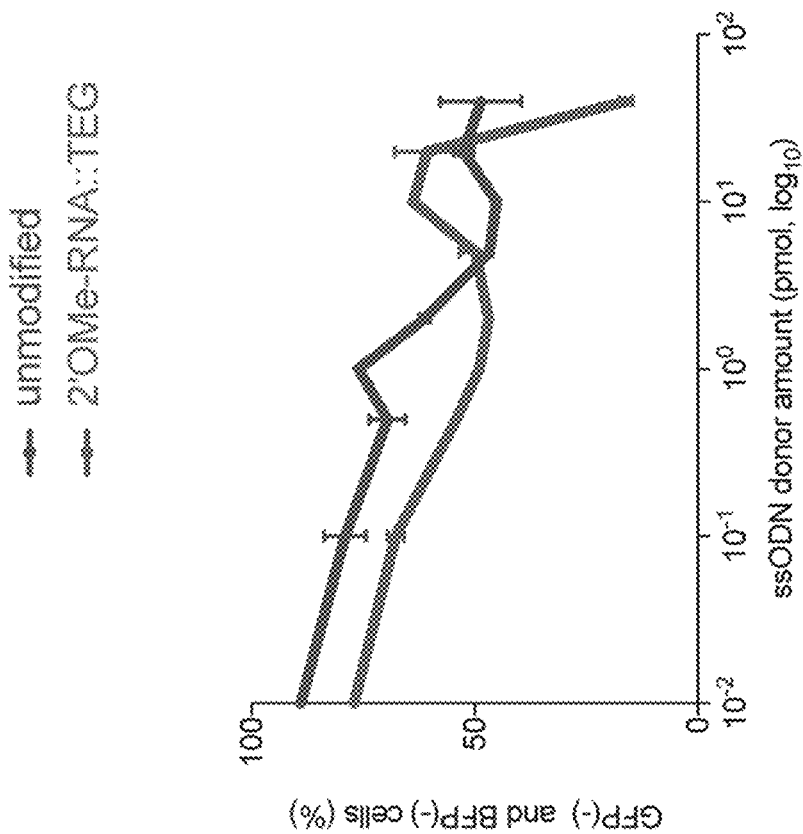
FIG. 12A-FIG. 12B depict genome editing using the GFP-to-BFP assay in K562 cells. SpyCas9, a sgRNA targeting GFP, and a donor template that will convert the GFP coding sequence to the BFP coding sequence were delivered and % BFP positive cells (FIG. 12A) and percent GFP and BFP negative cells (FIG. 12B) were determined by flow cytometry. Single stranded donor oligonucleotide (ssODN) templates were used at various amounts (pmol).
Figure 12A:
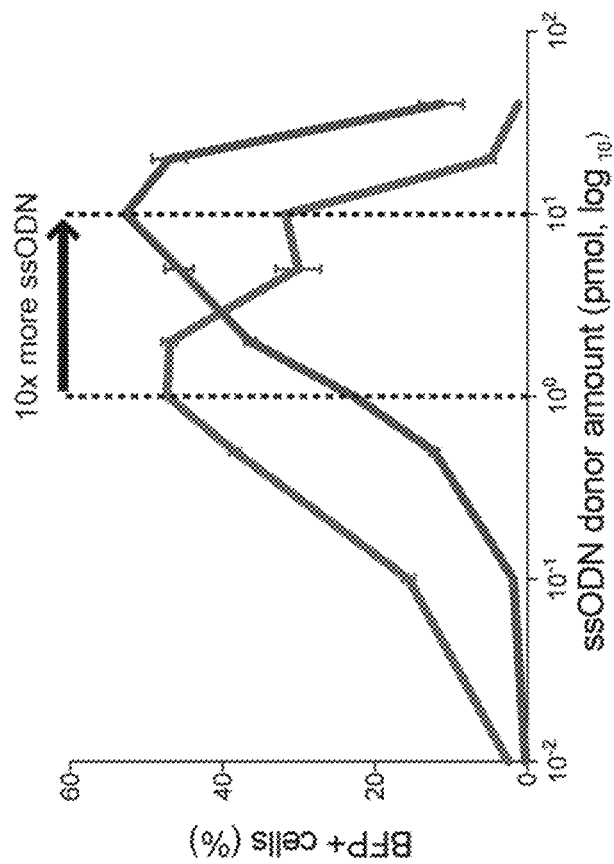
Figure 13B:
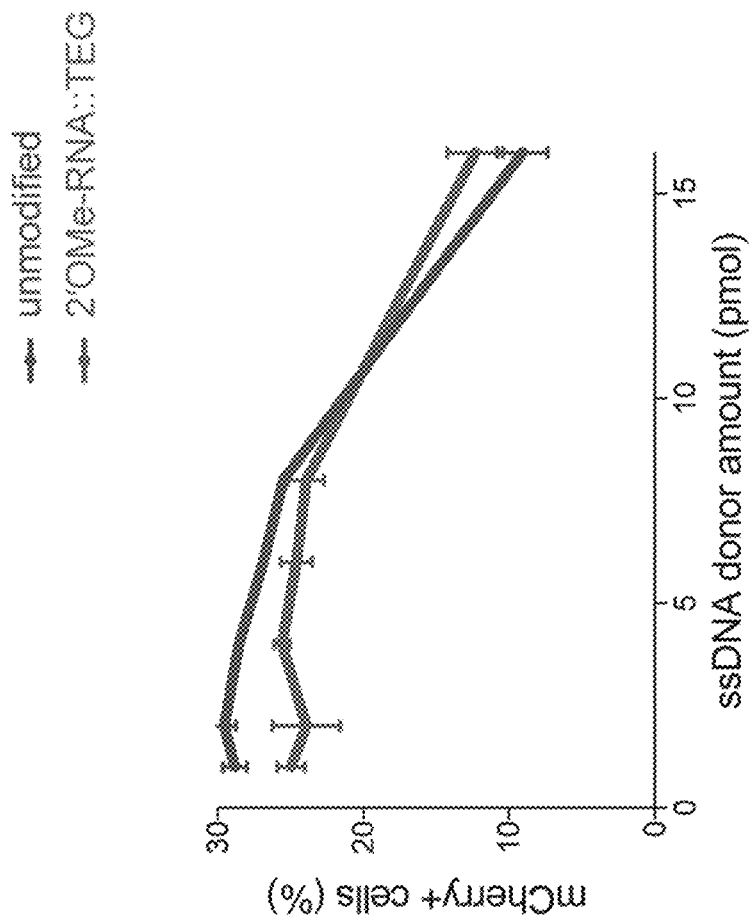
FIG. 13A-FIG. 13B depict genome editing using the TLR assay in HEK293T cells. SpyCas9, a sgRNA targeting GFP, and a donor template that has the GFP coding sequence were delivered and percent GFP positive cells (FIG. 13A) and percent mCherry positive cells (FIG. 13B) were determined by flow cytometry. Long, single stranded DNA (ssDNA) donor templates were used at various amounts (pmol).
Figure 13A:
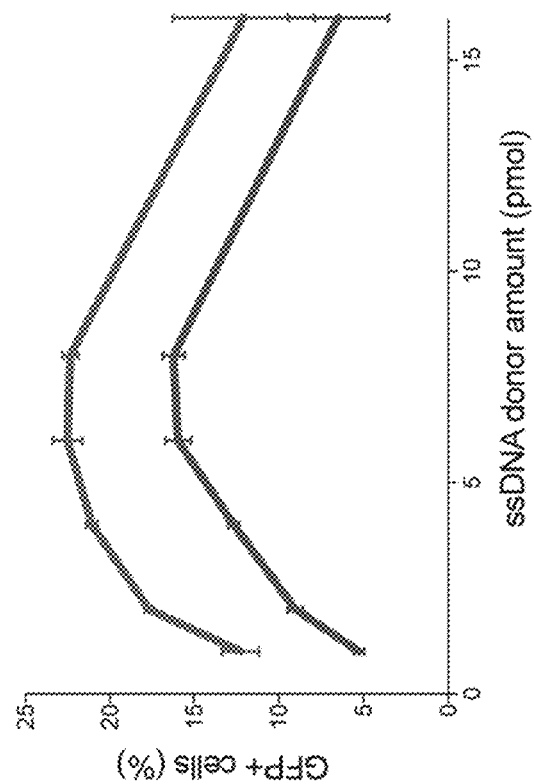

The experiments described thus far have employed dsDNA donors that are easy to generate by PCR; however, single stranded DNA (both short, ssODN, and long, ssDNA) donors have become widely used in many HDR editing protocols. To test whether TEG modifications of short ssODN donors improve HDR efficiency, a GFP-to-BFP assay in K562 cells was performed (see methods; see also Glaser et al. Mol. Therapy—Nucleic Acids. 5: e334 (2016)). With donor amounts less than 2 pmol, TEG modification consistently increased the percentage of BFP+ cells (HDR) by over two-fold compared to the unmodified donor (FIG. 12A) with concurrent decline in GFP− and BFP− cells (NHEJ) (FIG. 12B). Interestingly, however, donor amounts over 2 pmol yielded lower percentage of BFP+ cells for TEG-modified donors compared to unmodified ssODNs. These titrations indicate that TEG-modified donors are more potent and yield maximum HDR at amounts at least 10-fold lower than ssODN donors without end-modifications. Furthermore, the addition of a 2'OMe-RNA::TEG tail to a long ssDNA donor elicited a consistent and significant boost of up to two-fold over unmodified ssDNA donors in HDR efficiency (with corresponding reductions in NHEJ) across a range of concentrations in the TLR assay (FIG. 13A and FIG. 13B). For unknown reasons, optimal editing with ssDNA required several-fold higher donor amounts than dsDNA, and peak efficiencies plateaued at 22%, well below the maximum levels achieved with TEG-modified dsDNA donors.

Example 4—DNA Donor Toxicity and HDR Enhancement in Zebrafish

EGFP Integration in Danio rerio Embryos

In D. rerio, the EGFP sequence was inserted in-frame with keratin type 1 c19e (krtt1c19e) coding sequences to obtain C-terminus fusion protein. Donor templates were generated by PCR (100 bp homology arms) with or without the terminal adaptors (as described above). Linker and polyadenylation (PolyA) sequences were introduced into the donor template (see, Hisano et al. Scientific Reports. 5. (2015)). One to two cell embryos were injected with a Cas9 RNP mixture (Cas9 RNP—0.8 fmol per embryo) and different amounts of the dsDNA donor (6.25 to 50 pg per embryo) with or without the terminal adaptors. Injected embryos were maintained at 28.5° C. 48 hours post fertilization, embryos were scored as dead, abnormal or normal depending on the morphology. 'Normal' embryos were then screened under the fluorescent dissection microscope for GFP expression in the epidermis as described previously (Hisano, supra). Embryos with visible GFP expression were grouped into a broad, intermediate, or narrow category based on the GFP expression pattern. To confirm the on-target integration of GFP, embryos were randomly selected, lysed, and genomic DNA was extracted using the DNeasy Blood and Tissue kit (Qiagen #69506) according to the manufacturer's protocol. Using the purified genomic DNA as a template, PCR was performed with primer pairs that amplify junctions of the genomic DNA and the homology sequence in the donor molecules as described before (Hisano, supra) and precise integrations were confirmed by sequencing the PCR DNA.

Figure 14:
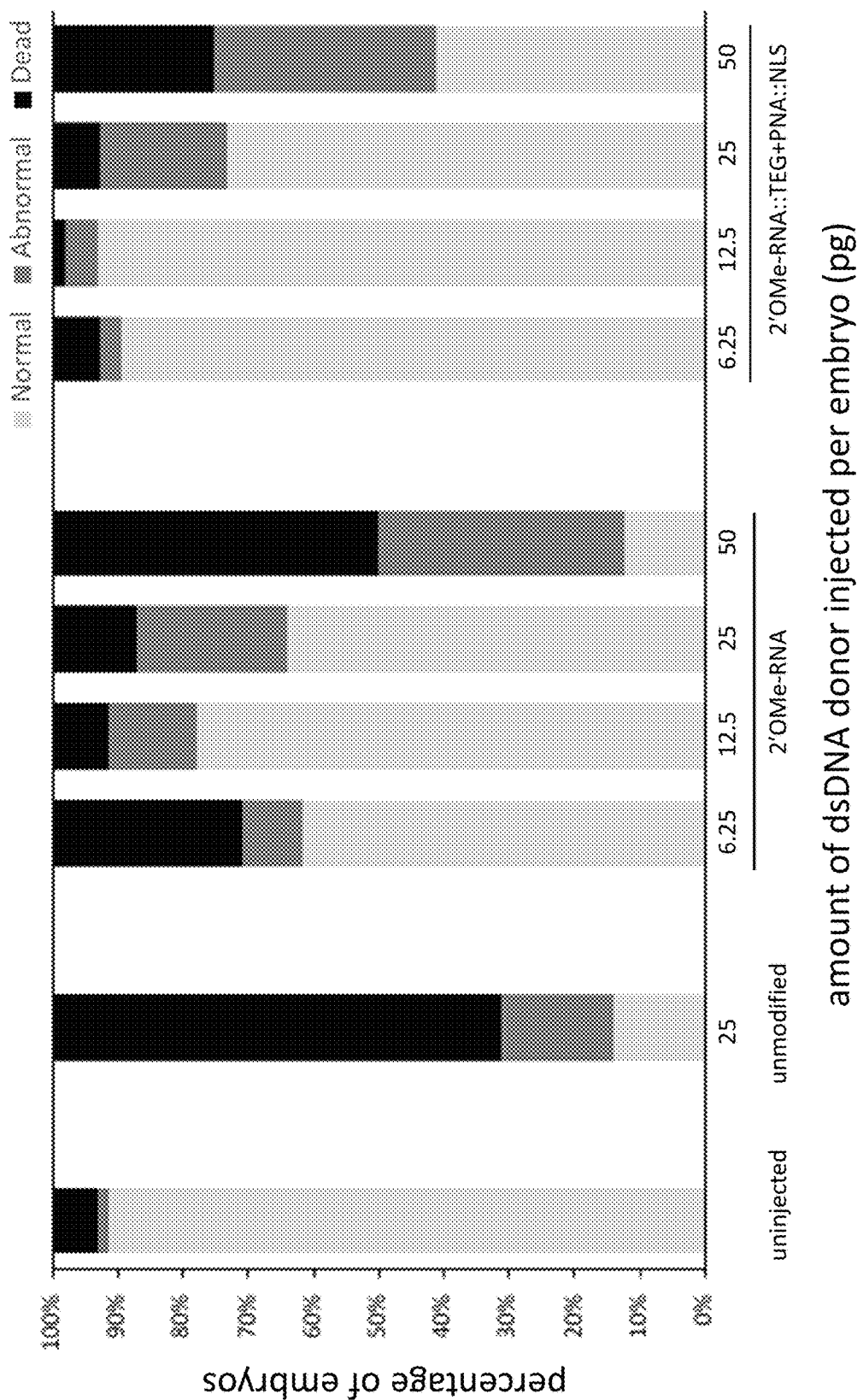
FIG. 14 depicts dsDNA donor toxicity in zebra fish after injection of a donor template with a 2'OMe-RNA adaptor or a 2'OMe-RNA::TEG adaptor and PNA::NLS adaptor ligand. Donor templates were injected in zebra fish embryos at 6.25 pg, 12.5 pg, 25 pg, and 50 pg per embryo.
Figure 15:
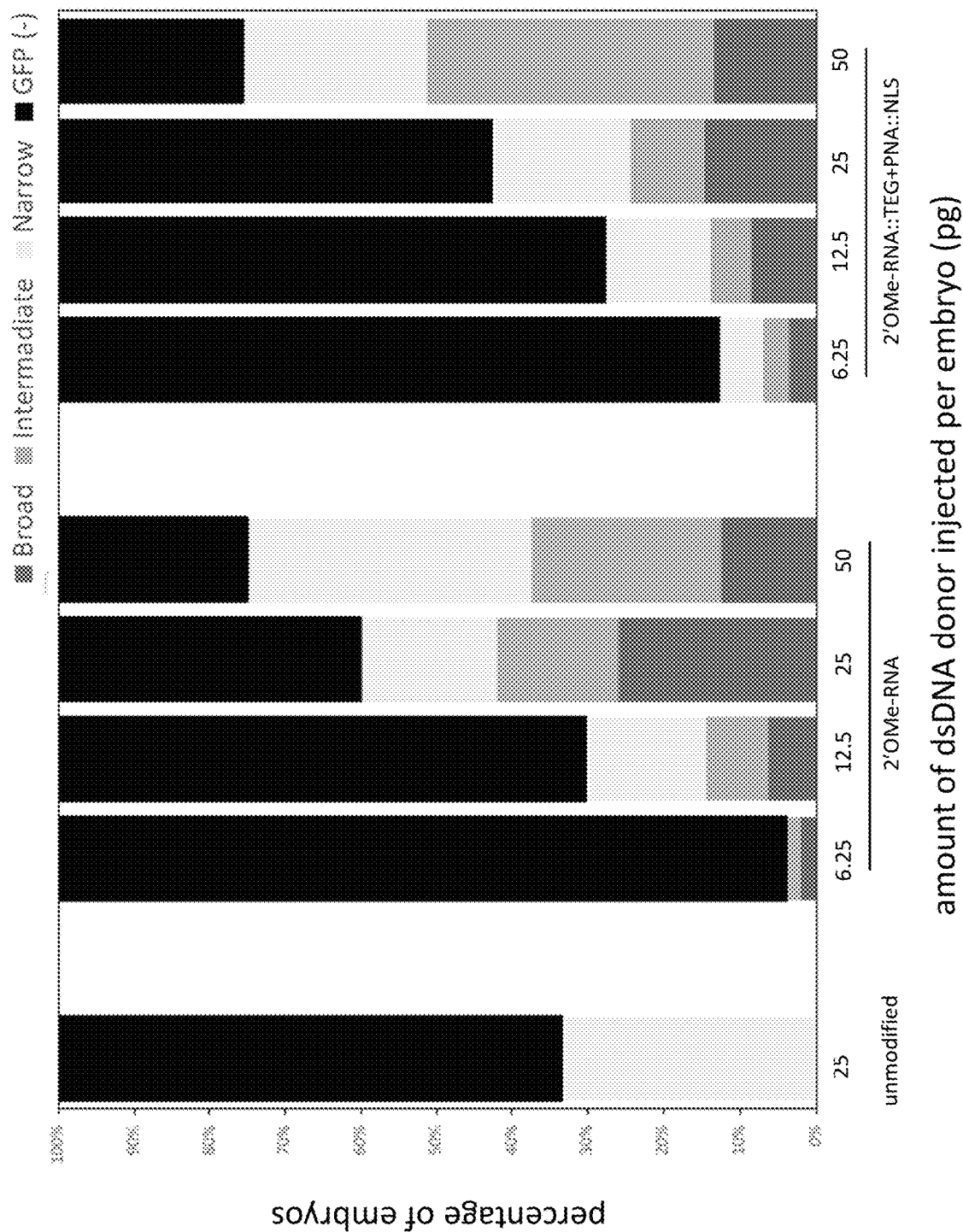
FIG. 15 depicts HDR efficiency in zebra fish embryos injected with a donor template with a 2'OMe-RNA adaptor or a 2'OMe-RNA::TEG adaptor and PNA::NLS adaptor ligand. Donor templates were injected in zebra fish embryos at 6.25 pg, 12.5 pg, 25 pg, and 50 pg per embryo.
Figure 16:
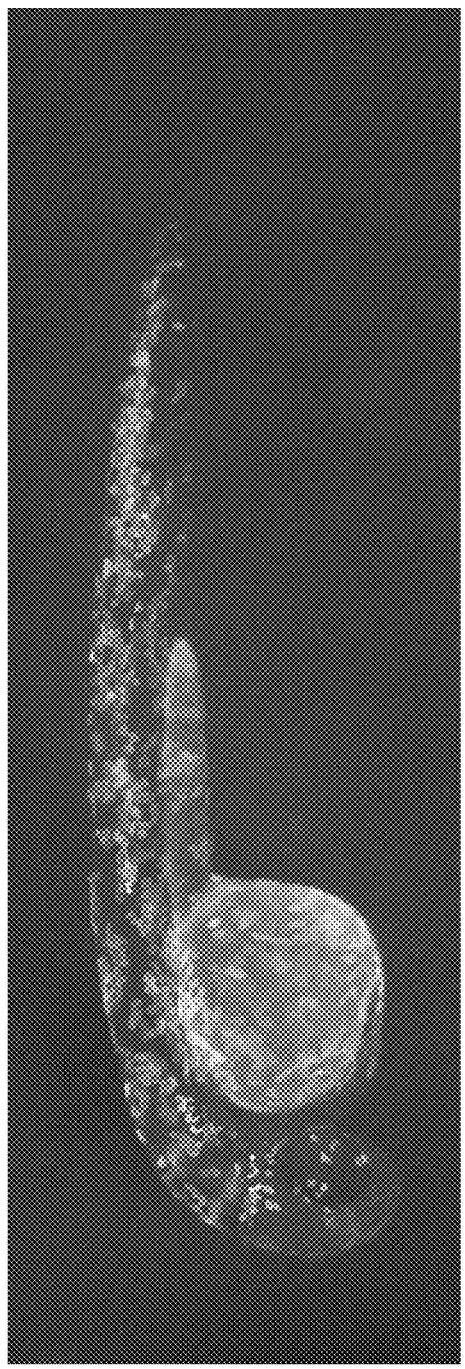
FIG. 16 depicts an image showing broad krtt1c19e-GFP expression in the epidermis of a zebrafish embryo 48 hours post-fertilization.

To test if these modified DNA donors could also improve HDR efficiency in vertebrates, the zebrafish, D. rerio, was chosen as the model system. Zebrafish embryos are highly amenable to microinjection and yet efficient editing of the fish genome with long dsDNA donors has been elusive. GFP dsDNA donors were designed to generate C-terminal fusions at keratin type1-c19e (krtt1c19e) gene (Hisano, supra) (see above). One to two cell embryos were microinjected with a mixture of Cas9 RNPs and dsDNA donors with or without terminal adaptors. Strikingly, modified DNA donors were significantly less toxic to the embryos compared to the unmodified donors (FIG. 14). 64% of the embryos injected with 2'-OMe-RNA::TEG modified donors (25 pg per embryo) had normal morphology, whereas only 14% of the embryos injected with unmodified donors (25 pg per embryo) had normal morphology (FIG. 14). Annealing PNA::NLS to 2'OMe-RNA::TEG modifications further reduced the toxicity (74% normal embryos). The embryos were then scored for rate of GFP integration and it was found that modified DNA donors (up to 75% of normal embryos) were significantly more efficient compared to the unmodified donors (33% of normal embryos) (FIG. 15). Like in *C. elegans*, donors with 2'OMe-RNA::TEG modifications performed significantly better than the unmodified donors but annealing PNA::NLS did not further improve rate of GFP integration. Furthermore, only modified DNA donors yielded embryos expressing GFP broadly throughout the tissue (FIG. 15, dark green bars and FIG. 16).

Figure 18:
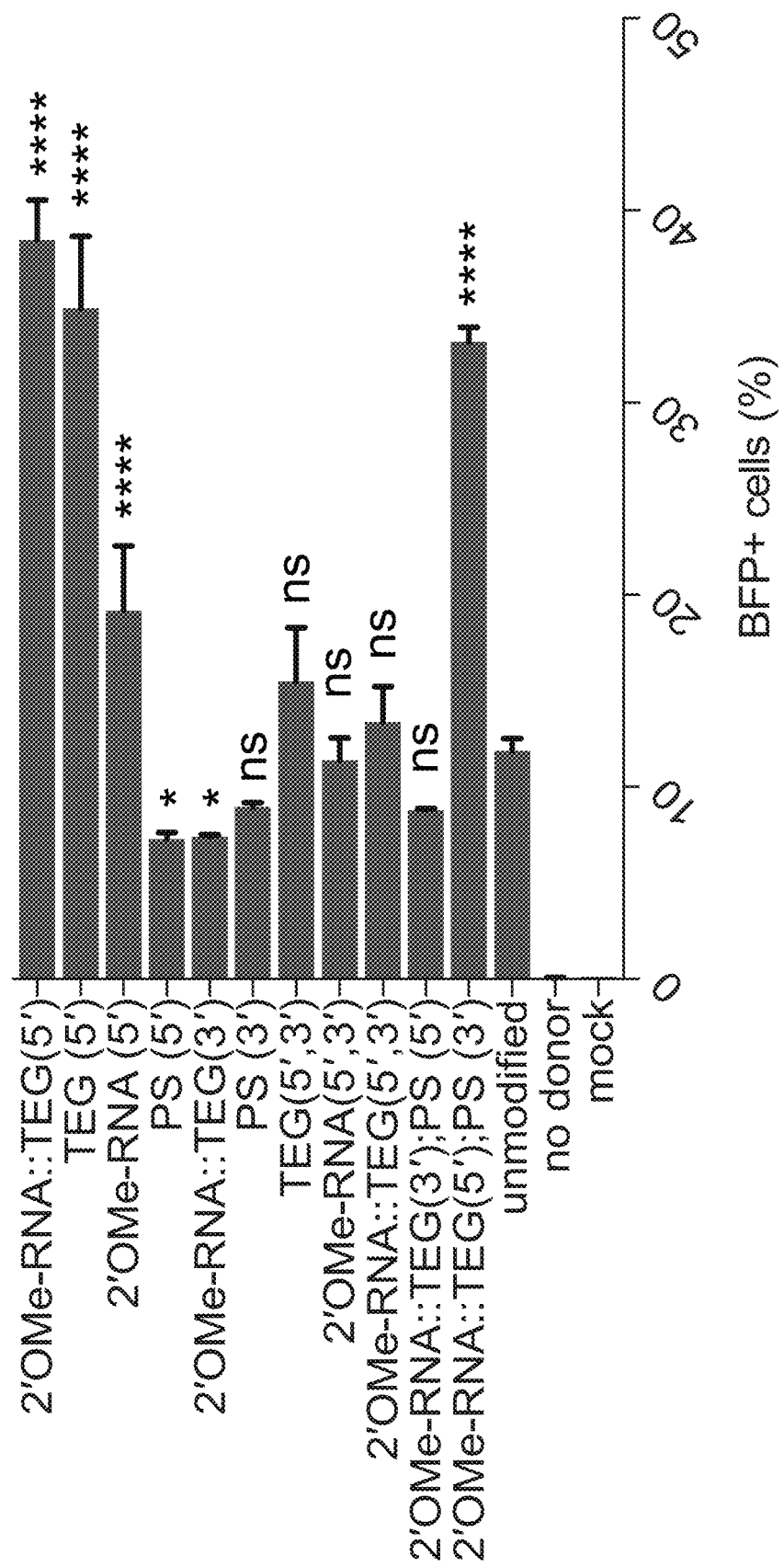
FIG. 18 depicts genome editing using the GFP-to-BFP assay in K562 cells. SpyCas9, a sgRNA targeting GFP, and a donor template that will convert the GFP coding sequence to the BFP coding sequence were delivered and percent BFP positive cells were determined by flow cytometry.
Figure 19:
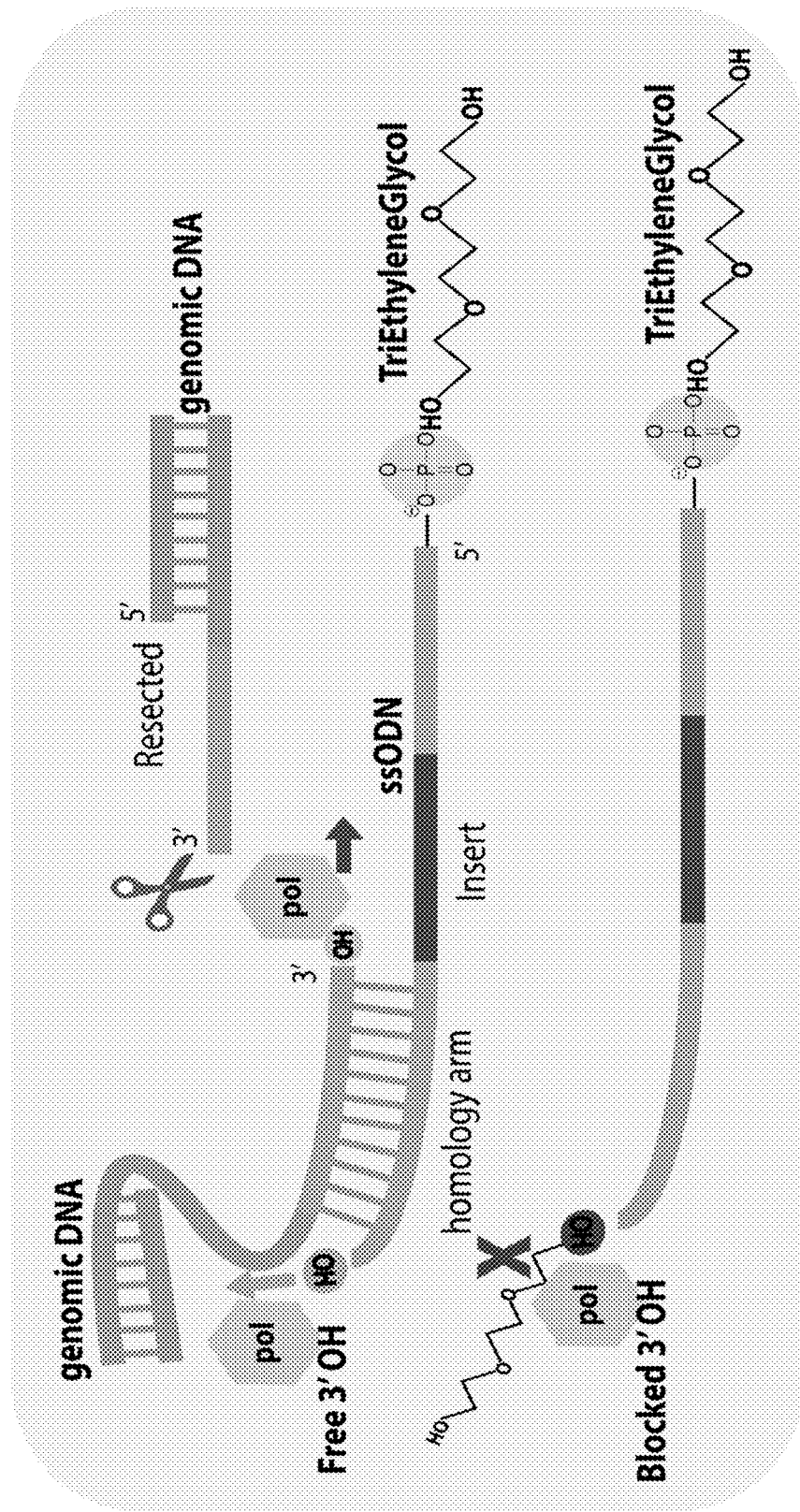
FIG. 19 depicts a schematic outlining the requirement of a 3' OH on the DNA donor template for enhancing HDR.

Example 5—3' Terminal Adaptors and Phosphorothioate Modifications on HDR Efficiency The GFP to BFP assay described above was next used to test the effect of 3' terminal adaptors and phosphorothioate modifications on HDR efficiency. A 2'-OMe-RNA::TEG, 2'OMe-RNA, TEG, or phosphorothioate (PS) modification was introduced at the 5' end, 3' end, or both (FIG. 18). It was observed that 3' terminal hydroxyl-linked modifications (2'OME-RNA or TEG) do not promote HDR at low donor amounts (0.5 pmol). Furthermore, single 5' and 3' non-terminal PS modifications are well tolerated. However, these modifications do not improve HDR efficiency at low amounts where terminal modifications such as TEG or 2'OMe-RNA have potent effects. The results indicate that HDR improvement requires availability of 3' OH for priming, ligation, or other mechanisms (FIG. 19). When a ssODN is provided as a donor to repair the double strand break in the genomic DNA, strand invasion takes place and polymerases can either extend the 3' end of the genomic DNA (using ssODN as the template) or the 3' end of the ssODN itself using the genomic DNA as the template. However, when end-modifications are added to the 3' OH group, ssODN cannot be used as a primer for extension by the polymerases thereby reducing the potency of ssODNs. Therefore, it is proposed that blocking the 5' end while leaving the 3' OH group open is key to increase the potency of the short single stranded donors (FIG. 19).

In summary, it has been surprisingly discovered that the addition chemically diverse terminal adaptors (e.g., TEG or 2'OMe-RNA) to a donor DNA template can serve to dramatically improve HDR efficiency. For example, the modifications dramatically increased the potency of dsDNA, ssDNA and ssODN donors, requiring significantly lower concentrations to achieve comparable or better editing than their unmodified counterparts. Some of the potential benefits of the modifications disclosed herein may include improved stability and nuclear retention of the end-protected donor.

Figure 20:
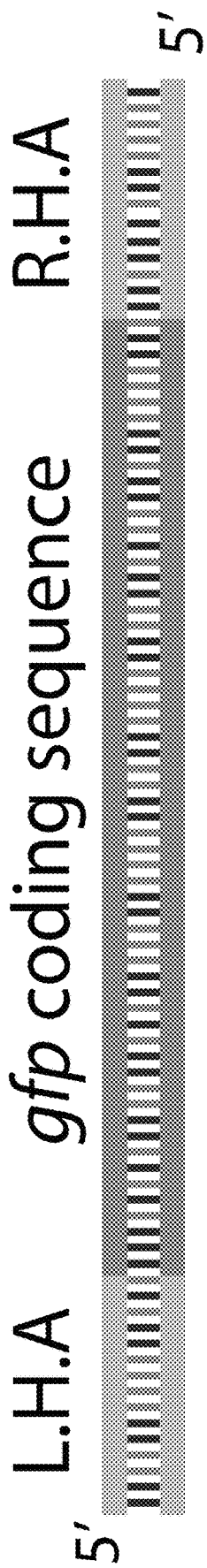
FIG. 20 depicts a schematic of a blunt-ended, PCR-generated DNA donor with a left homology arm and right homology arm that does not contain chemical modifications.

Example 6—Asymmetric DNA Donor Templates without Chemical Modifications on HDR Efficiency High rates of HDR have been reported using PCR-generated double stranded DNA (dsDNA) donors of about 1 kb with about 35 base pair homology arms (Paix et al., supra). However, these results were not reproducible using the original or optimized protocols (data not shown). PCR-generated DNA donor templates encoding GFP with different homology arm lengths were used. Extending the homology arms to 120 base pairs at both ends of the donor (blunt) resulted in low but reproducible levels of integration at the *C. elegans* wago-1 and wago-2 loci (FIG. 20 and Table 1). It was speculated that the dsDNA was interfering with Cas9 RNP activity. It was found that pre-assembling Cas9 RNPs for 10 minutes at 37° C. prior to adding donor DNA or rol-6 marker plasmid provided a consistent boost to editing efficiency. Nevertheless, a remarkable difference in efficiency between ssODN donors and longer dsDNA donors as repair templates was observed.

Figure 21:
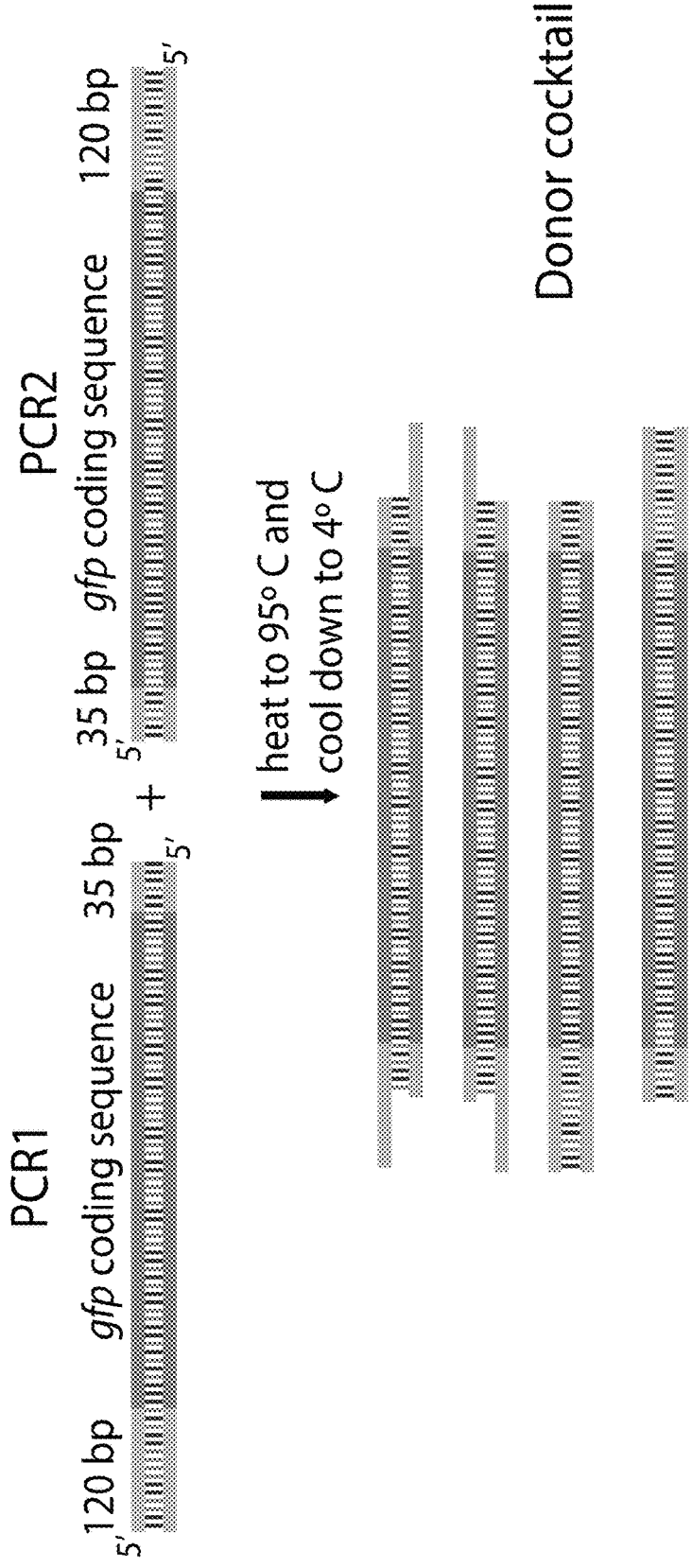
FIG. 21 depicts a schematic of PCR-generated DNA donors with 120 base pair and 35 base pair asymmetric homology arms.
Figure 22:
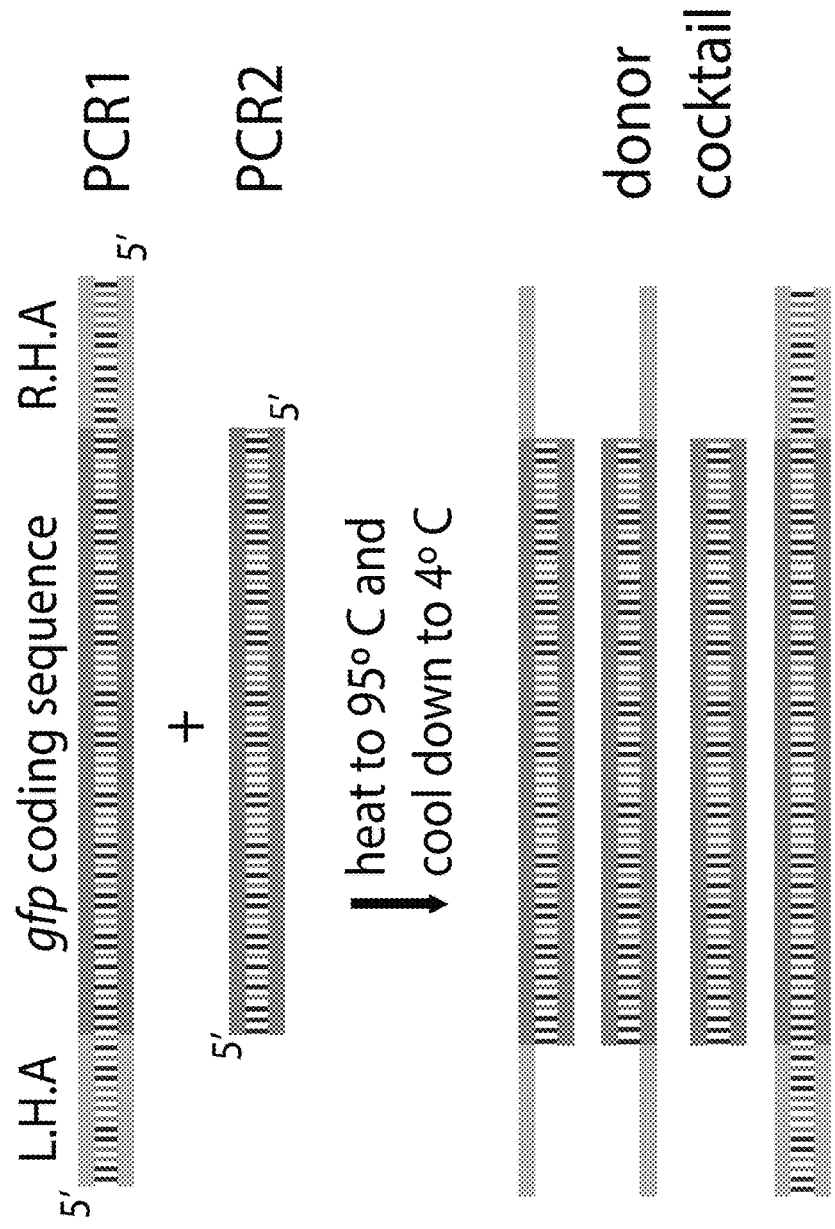
FIG. 22 depicts a schematic of PCR-generated DNA donors with 120 base pair and 0 base pair asymmetric homology arms.

A recent study proposed that ssODN donors are integrated by a highly efficient single stranded template repair (SSTR) pathway, while dsDNA donors rely on a less efficient homology directed repair (HDR) pathways. It was speculated that the improved efficiency of ssDNA could achieved by employing large PCR-based donors with single stranded overhangs. To do this, two PCR donors to target the same locus were generated: one with a 120 bp left homology arm and a 35 bp right homology arm, and the other with a 35 bp left homology arm and 120 bp right homology arm (FIG. 21). By mixing these donors at equimolar quantities, then melting and re-annealing the mixture, four different molecules were generated, two of which have either 3' or 5' single stranded overhangs (FIG. 21). Strikingly, this mixture of hybrid dsDNA donors consistently yielded higher rates of accurate GFP integration than melted and re-annealed traditional blunt donors (Table 1). The hybrid donor cocktail was tested further by editing four additional loci using GFP and mCherry donors, and consistently achieving rates comparable to ssODN donors, with about 20% of the F1 group showing the roller phenotype, as described above. Single stranded overhangs could also be achieved by annealing a symmetric PCR donor with 120 bp homology arms to a PCR product containing just the insert, without the homology arms (FIG. 22 and Table 1). It was found that this donor confirmation also dramatically boosted accurate editing with 120 bp homology arms, but the efficiency is significantly lower if 35 bp homology arms are used (Table 1).

TABLE 1

Percent HDR with various asymmetric DNA donor templates.

| Locus | Donor Type-Length of homology arms | % HDR |
|---|---|---|
| wago-1 | Blunt - 120 bp/120 bp | 10.53 |
| wago-1 | Asymmetric - 120 bp/35 bp | 12.63 |
| wago-1 | Asymmetric - 120 bp/0 bp | 20.8 |
| wago-1 | Asymmetric - 35 bp/0 bp | 6.5 |
| wago-2 | Blunt - 120 bp/120 bp | 1.8 |
| wago-2 | Asymmetric - 120 bp/35 bp | 8.33 |
| wago-2 | Asymmetric - 120 bp/0 bp | 13 |

Example 7—DNA Donor Templates on HDR Efficiency In Vivo

Figure 23:
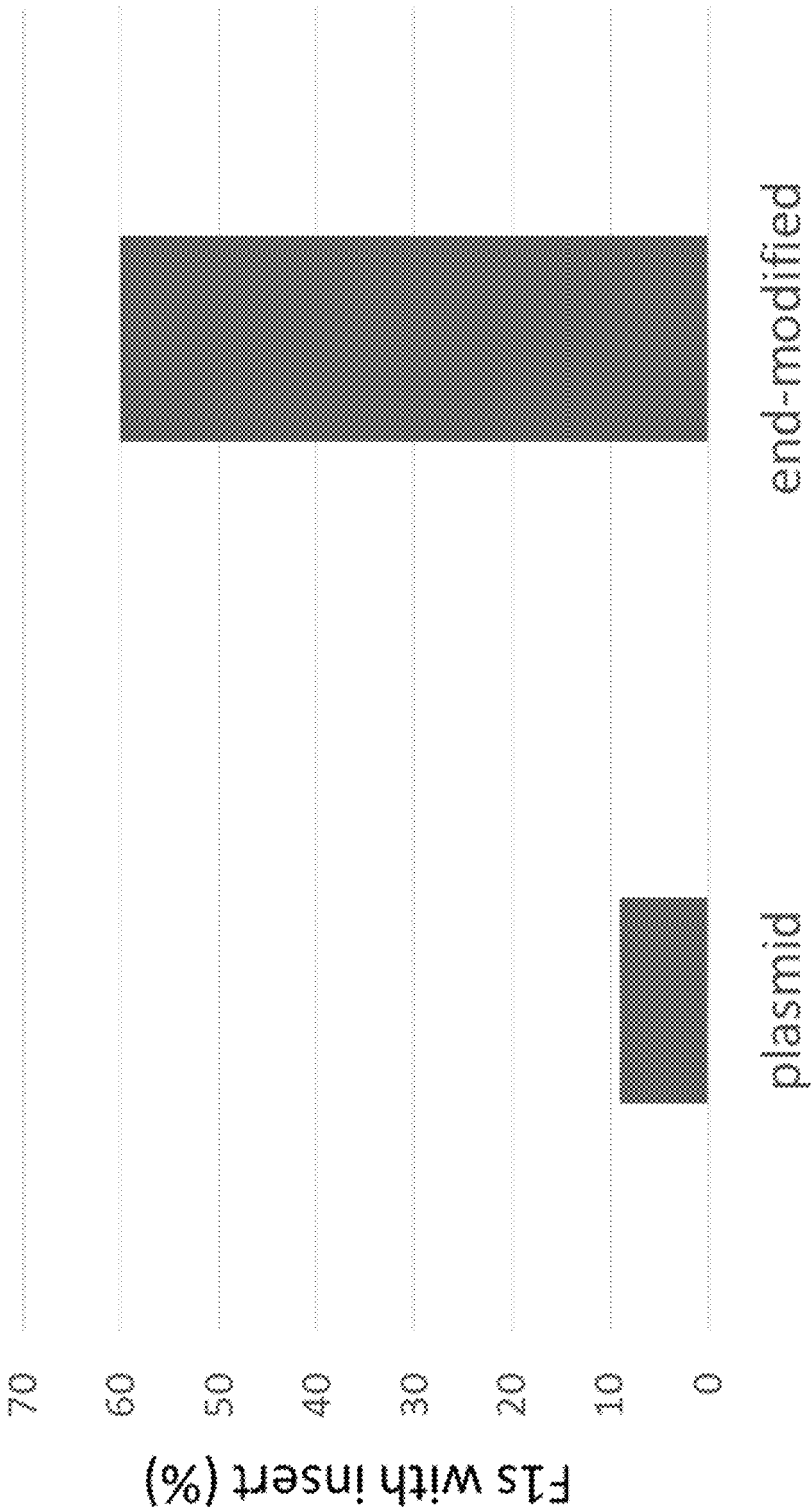
FIG. 23 depicts the efficiency of DNA donor integration between a modified DNA donor and control plasmid in vivo in a mouse model system.

A mouse model was used to test HDR efficiency of the modified DNA donor molecules in vivo. A 4.6 kb long traffic light reporter (TLR), was integrated, or knocked-in, into the ROSA-26 locus. HDR efficiency was determined using donors either as plasmid or end-modified double-stranded PCR products. Using donors with 2'-OMe-RNA-TEG 5' end-modifications, it was found that 9 out of 15 (60%) founder animals had the insert compared to 1/11 (9%) using plasmid as a donor. This result indicates that end-modifications make the donor molecules more potent even in mammalian (in vivo) settings (FIG. 23). The injection mixtures for this experiment are as follows: plasmid donor experiment—Cas9 mRNA (50.0 ng/µl), Cas9 protein (50.0 ng/µl), sgRNA (20 ng/µl), plasmid DNA donor (10 ng/µl); end-modified donor experiment—Cas9 mRNA (50.0 ng/μl), Cas9 protein (50.0 ng/μl), sgRNA (20 ng/μl), modified DNA donor (1 ng/μl).

Example 8—Off-Target Integration of DNA Donor Templates

Figure 24B:
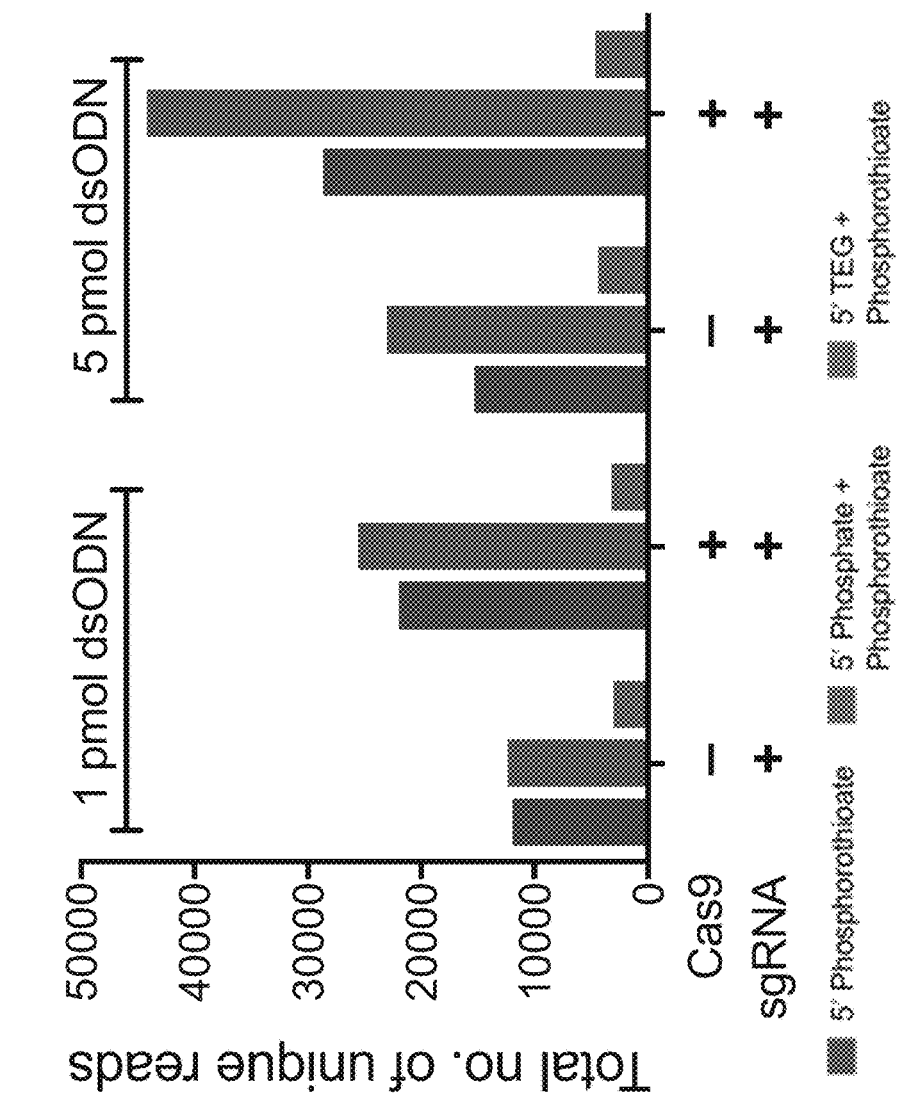
FIG. 24A-FIG. 24B depict GuideSeq results for identifying off-target DNA donor integration events.
Figure 24A:
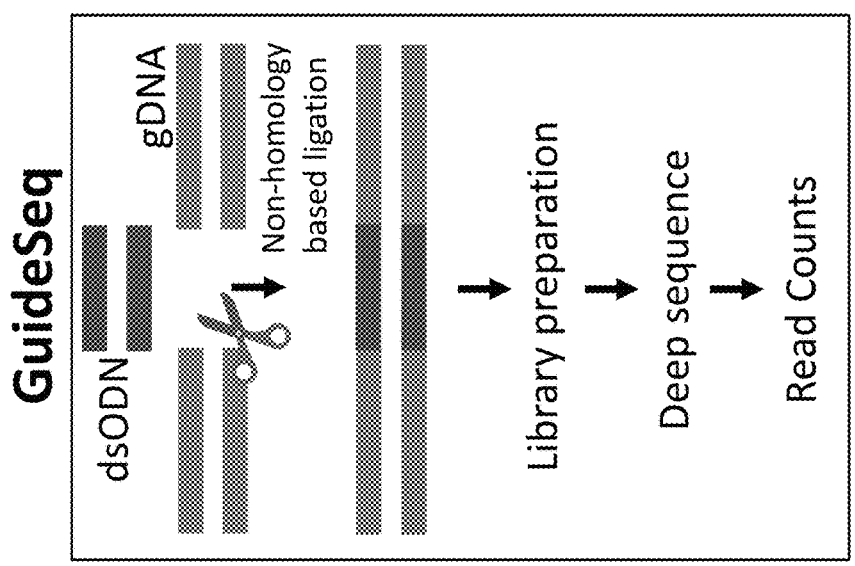
Figure 25:
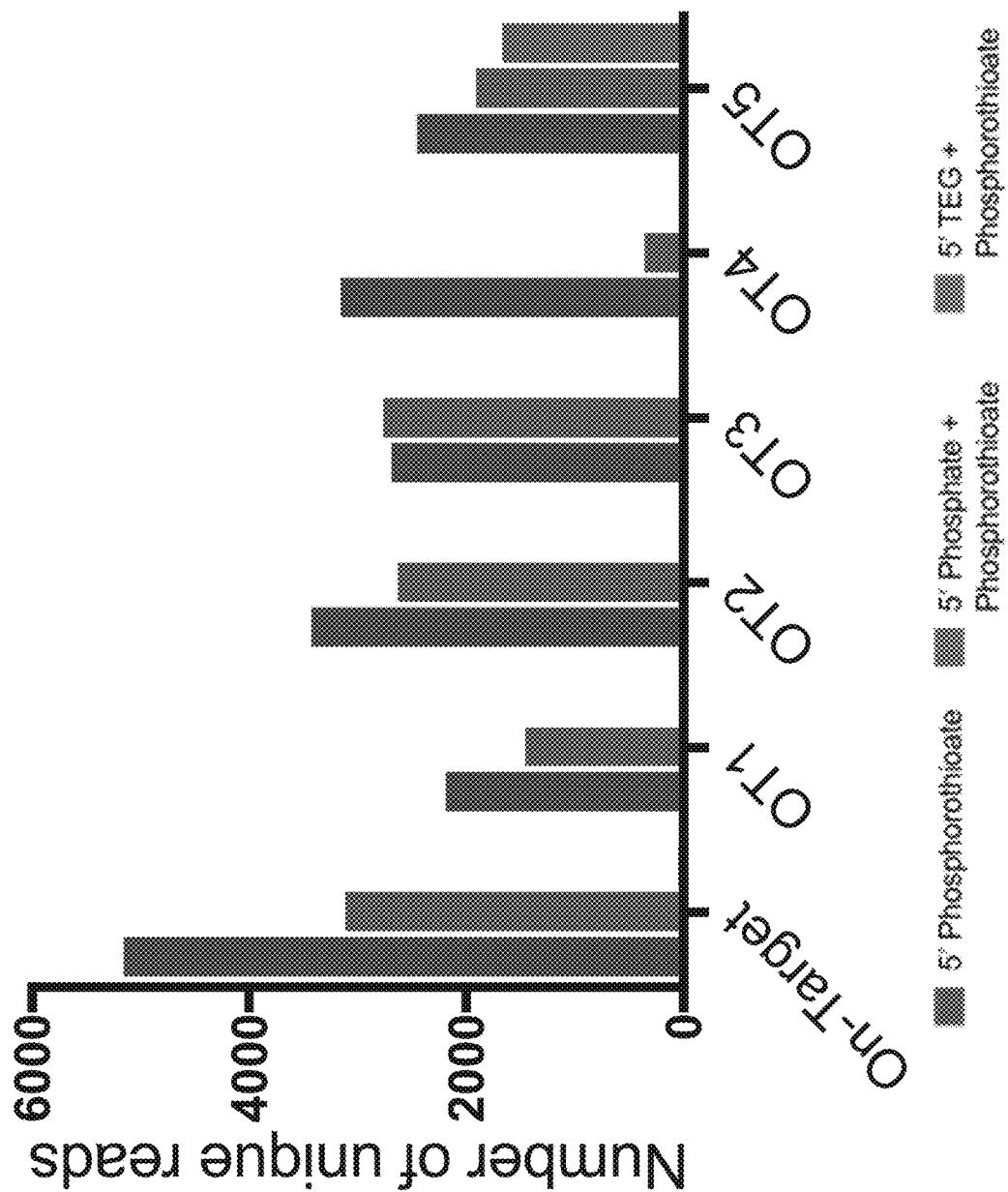
FIG. 25 depicts the frequency of direct-integration specifically at the ON-target and top-8 off-target sites of the guide RNA used.

GuideSeq was performed to test whether end-modifications prevent double stranded DNA from directly ligating into the off-target cut sites of the guide RNA (Tsai et al., Nature Biotechnology. 33" 187-197 (2015)). SpyCas9 protein and synthetic guide RNA targeting ARHGEF9 locus were used in HEK293 cells. The ARHGEF9 locus was chosen because it has been shown to have multiple off-target sites (Amrani et al., Genome Biology. 19: 214 (2018)). Three different types of DNA donors were used, each one being 34 bp in length and lacking homology arms. The three types were 1) a 5' phosphorothioate modified DNA donor, 2) a 5' phosphorothioate and phosphate modified DNA donor, and 3) a 5' TEG and phosphate DNA donor. Over-all integration of this non-homology based direct ligation is much lower when TEG is used as the end-modification (FIGS. 24A and 24B). This result indicates that end-modifications suppress direct ligation of DNA at the random off-target cut sites in the genome. It was also found that end-modifications suppress integration of double stranded DNA at the top off-target (OT) sites of the guide RNA targeting the ARHGEF9 locus. (FIG. 25).

Example 9—Spermine-Modified DNA Donor Templates on HDR Efficiency

Figure 26:
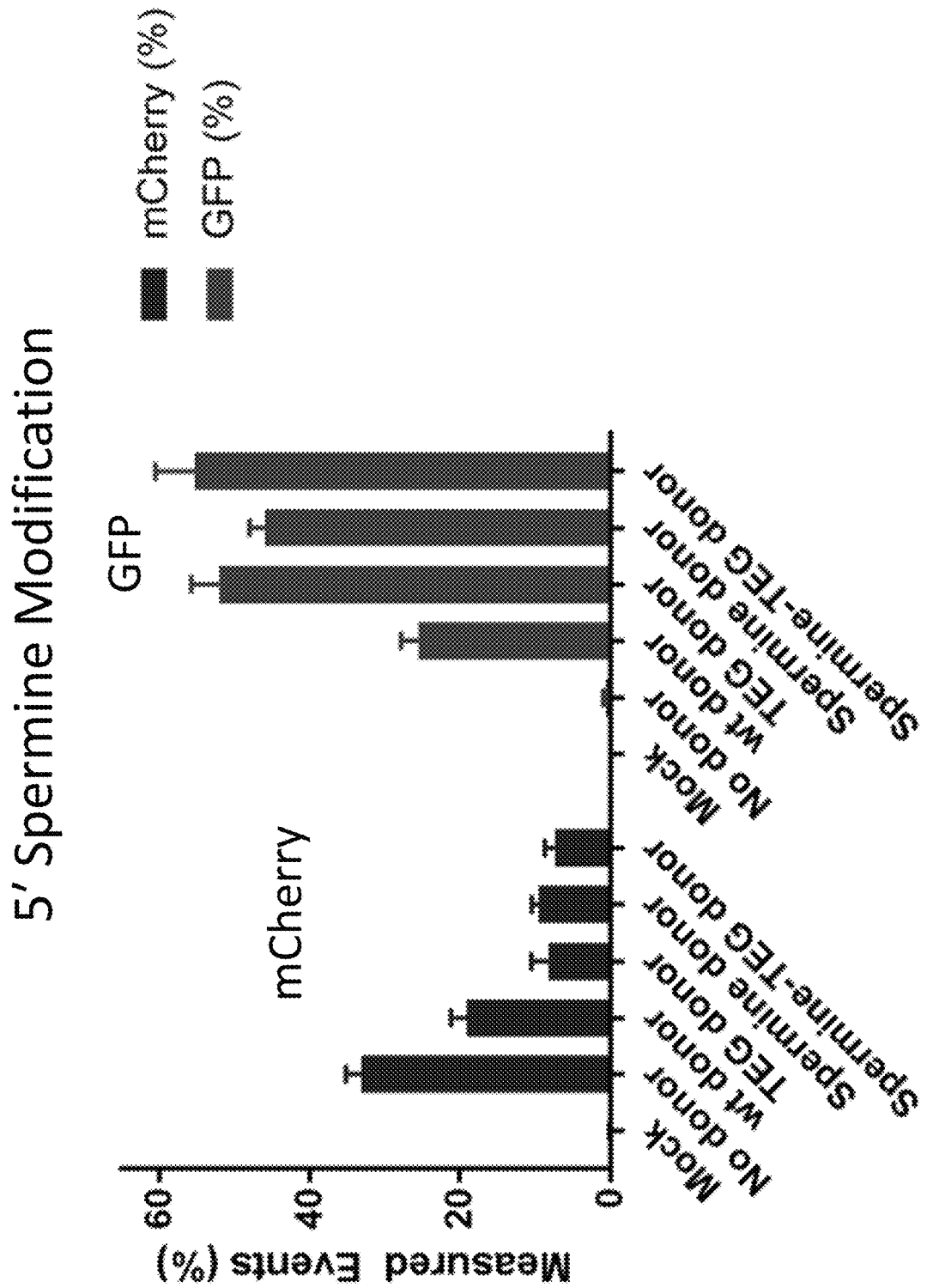
FIG. 26 depicts genome editing using the TLR system in HEK293T cells. Unmodified GFP DNA donors were compared to GFP DNA donors with a 5' TEG modification, a 5' spermine modification, or a 5' TEG and spermine modification.

Modified DNA donors with a 5' spermine modification were tested for their effect on HDR efficiency. Using the HE293 TLR assay, it was found that these spermine-modified DNA donors were more effective than unmodified DNA donors. The improvement in efficiency is comparable to that of TEG alone as well. When combining TEG and spermine modifications in the same DNA donor, there was also an increase in the HDR efficiency compared to the unmodified donors (FIG. 26).

These combined results indicate that 2'-OMe RNA, PEG, spermine, and combinations of these modifications make DNA donor molecules more potent for HDR.

What is claimed is:

1. A genome-editing system comprising:
   i) an isolated nucleic acid donor molecule comprising
      (a) a region having portions of nucleic acid homology to a target sequence; and
      (b) one or more terminal adaptors comprising an ethylene glycol or a polyethylene glycol (PEG);
      wherein the nucleic acid donor molecule length is 100 nucleotides or more,
      wherein the one or more terminal adaptors are attached to the 5' end and/or the 3' end of the nucleic acid donor molecule; and
      wherein the nucleic acid donor molecule is capable of being introduced into a target sequence by a homology-directed repair (HDR) or homology-independent targeted integration (HITI) mechanism; and
   ii) an agent that creates a double-stranded break at or near the target sequence.

2. The genome-editing system of claim 1, wherein the portions of nucleic acid homology are about 20 bases in length to about 1,000 bases in length.

3. The genome-editing system of claim 1, wherein the nucleic acid donor molecule comprises a cleavage site sequence that is also present in the target sequence.

4. The genome-editing system of claim 1, wherein the PEG is tetraethylene glycol or triethylene glycol.

5. The genome-editing system of claim 1, wherein the PEG comprises 2-100 or more ethylene glycol units.

6. The genome-editing system of claim 1, wherein the PEG comprises 2-20, 20-40, 40-60, 60-80, or 80-100 ethylene glycol units.

7. The genome-editing system of claim 1, wherein the PEG comprises 2, 3, 4, 5, 6, 7, 8, 9, 10, 11, 12, 13, 14, 15, 16, 17, 18, 19, or 20 ethylene glycol units.

8. The genome-editing system of claim 1, wherein the PEG comprises 4, 6, 9 or 12 ethylene glycol units.

9. The genome-editing system of claim 1, wherein the isolated nucleic acid donor molecule further comprises an exogenous nucleotide sequence to be inserted into the genome of a cell.

10. The genome-editing system of claim 9, wherein the exogeneous nucleotide sequence comprises a gene.

11. The genome-editing system of claim 10, wherein the gene encodes for a protein.

12. The genome-editing system of claim 11, wherein the protein is a therapeutic protein.

13. The genome-editing system of claim 11, wherein the gene is from the same species organism of the cell in which the gene is to be inserted.

14. The genome-editing system of claim 11, wherein the gene is from a different species organism of the cell in which the gene is to be inserted.

15. The genome-editing system of claim 9, wherein the exogenous sequence encodes for a non-coding RNA.

16. The genome-editing system of claim 15, wherein the noncoding RNA is selected from the group consisting of transfer RNAs (tRNAs), ribosomal RNAs (rRNAs), siRNA, miRNA, piRNA, snoRNA, snRNA, and exosomal RNA (exRNA).

17. The genome-editing system of claim 9, wherein the exogenous sequence is not capable of being expressed.

18. The genome-editing system of claim 9, wherein the exogenous sequence is a sequence that reduces or eliminates the expression of an endogenous gene in the cell.

19. The genome-editing system of claim 9, wherein the exogenous sequence is flanked by a first 5' homology arm of about 20 nucleotides in length to about 1000 nucleotides in length and second 3' homology arm of about 20 nucleotides in length to about 1000 nucleotides in length.

20. The genome-editing system of claim 1, wherein the agent is a polypeptide, or a nucleic acid sequence encoding a polypeptide, selected from the group consisting of a zinc finger nuclease (ZFN), a transcription-activator like effector nuclease (TALEN), and an RNA-guided nuclease.

21. The genome-editing system of claim 1, wherein the one or more terminal adaptors are attached to the 5' end but not the 3' end of the nucleic acid donor molecule.

22. The genome-editing system of claim 1, wherein the one or more terminal adaptors further comprise a single-stranded RNA (ssRNA) comprising one more modified nucleotides.

23. The genome-editing system of claim 22, wherein the ssRNA is about 8 bases in length to about 30 bases in length.

24. The genome-editing system of claim 22, wherein the ethylene glycol or PEG is attached to the ssRNA.

25. The genome-editing system of claim 22, wherein the ssRNA is about 1 base in length to about 50 bases in length.

26. The genome-editing system of claim 22, wherein the one or more modified nucleotides are 2'-O-methyl (2'-OMe) modified nucleotides.

27. The genome-editing system of claim 22, wherein the one or more modified nucleotides are selected from the group consisting of a 2'-O-alkyl modified nucleotide, a 2'-fluoro modified nucleotide, a nucleotide comprising a 5'-phosphorothioate group, a 2'-deoxy-modified nucleotide, a bridged nucleotide, a constrained nucleotide, a bicyclic nucleotide, an abasic nucleotide, a 2'-amino-modified nucleotide, a 2'-alkyl-modified nucleotide, a morpholino nucleotide, a phosphoramidate, a peptide nucleic acid, and a non-natural base comprising nucleotide.

28. The genome-editing system of claim 1, wherein the one or more terminal adaptors are bound to a terminal adaptor ligand having one or more functionalities.

29. The genome-editing system of claim 28, wherein the terminal adaptors can bind the terminal adaptor ligand through nucleic acid base-pairing interactions.

30. The genome-editing system of claim 28, wherein the terminal adaptor ligand comprises a peptide nucleic acid (PNA), a ssRNA, or a ssDNA.

31. The genome-editing system of claim 28, wherein the terminal adaptor ligand moiety is a nuclear localization signal (NLS).

32. The genome-editing system of claim 28, wherein the terminal adaptor ligand is attached to the terminal adaptor ligand moiety through a linker.

33. The genome-editing system of claim 1, wherein the nucleic acid donor molecule is double-stranded.

34. The genome-editing system of claim 1, wherein the nucleic acid donor molecule is single-stranded.

35. The genome-editing system of claim 34, wherein the single stranded nucleic acid is a single stranded donor oligonucleotide (ssODN).

36. A genome-editing system comprising:
  (a) an isolated nucleic acid donor molecule comprising
    (i) a first 5' homology arm of about 20 nucleotides in length to about 1000 nucleotides in length;
    (ii) an exogenous nucleotide sequence to be inserted into a genome of a cell;
    (iii) a second 3' homology arm of about 20 nucleotides in length to about 1000 nucleotides in length; and
    (iv) one or more terminal adaptors comprising a polyethylene glycol (PEG);
  wherein the first 5' and second 3' homology arms flank the exogenous nucleotide sequence;
  wherein the nucleic acid donor molecule length is 100 nucleotides or more,
  wherein the one or more terminal adaptors are attached to the 5' end and/or the 3' end of the nucleic acid donor molecule; and
  wherein the nucleic acid donor molecule is capable of being introduced into the genome of the cell by an HDR mechanism; and
  (b) an agent that creates a double-stranded break at or near a target sequence.

37. The genome-editing system of claim 36, wherein the agent is a polypeptide, or a nucleic acid sequence encoding a polypeptide, selected from the group consisting of a zinc finger nuclease (ZFN), a transcription-activator like effector nuclease (TALEN), and an RNA-guided nuclease.

38. A genome-editing system comprising:
  (a) an isolated nucleic acid donor molecule comprising
    (i) a region having portions of nucleic acid homology to a target sequence; and
    (ii) one or more terminal adaptors comprising a polyethylene glycol (PEG) attached to single-stranded nucleic acid of about 1 base in length to about 50 bases in length;
  wherein the nucleic acid donor molecule sequence length is 100 nucleotides or more, wherein the one or more terminal adaptors are attached to the 5' end but not the 3' end of the nucleic acid donor molecule; and wherein the nucleic acid donor molecule is capable of being introduced into a target sequence by an HDR or HITI mechanism; and ii) an agent that creates a double-stranded break at or near the target sequence.

39. The genome-editing system of claim 38, wherein the agent is a polypeptide, or a nucleic acid molecule encoding a polypeptide, selected from the group consisting of a zinc finger nuclease (ZFN), a transcription-activator like effector nuclease (TALEN), and an RNA-guided nuclease.

* * * * *

```
                         SEQUENCE LISTING

<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Nuclear localization signal

<400> SEQUENCE: 1

Pro Lys Lys Lys Arg Lys
1               5

<210> SEQ ID NO 2
<211> LENGTH: 23
<212> TYPE: DNA
<213> ORGANISM: Artificial Sequence
<220> FEATURE:
<223> OTHER INFORMATION: Guide sequence
<220> FEATURE:
<221> NAME/KEY: misc_feature
<222> LOCATION: (21)..(21)
<223> OTHER INFORMATION: n is a, c, g, or t

<400> SEQUENCE: 2
ctataaagac gatgacgata ngg                                        23
```